(12) United States Patent
Sund et al.

(10) Patent No.: US 7,915,295 B2
(45) Date of Patent: Mar. 29, 2011

(54) NON-NUCLEOTIDE REVERSE TRANSCRIPTASE INHIBITORS

(75) Inventors: Christian Sund, Huddinge (SE); Nathalie Roue, Huddinge (SE); Stefan Lindstrom, Huddinge (SE); Dmitry Antonov, Huddinge (SE); Christer Sahlberg, Huddinge (SE); Katarina Jansson, Huddinge (SE)

(73) Assignee: Medivir AB, Huddinge (SE)

( * ) Notice: Subject to any disclaimer, the term of this patent is extended or adjusted under 35 U.S.C. 154(b) by 868 days.

(21) Appl. No.: 10/584,933

(22) PCT Filed: Dec. 30, 2004

(86) PCT No.: PCT/SE2004/002034
§ 371 (c)(1),
(2), (4) Date: Sep. 10, 2007

(87) PCT Pub. No.: WO2005/066131
PCT Pub. Date: Jul. 21, 2005

(65) Prior Publication Data
US 2008/0070951 A1 Mar. 20, 2008

(30) Foreign Application Priority Data

Jan. 8, 2004 (SE) .................... 0400021
Mar. 9, 2004 (SE) .................... 0400585

(51) Int. Cl.
*A61K 31/453* (2006.01)
*C07D 405/12* (2006.01)

(52) U.S. Cl. ............... 514/337; 546/282.7; 546/272.4; 546/280.1; 546/281.1; 546/297

(58) Field of Classification Search ........... 546/282.7, 546/272.4, 280.1, 281.1, 297; 514/337
See application file for complete search history.

(56) References Cited

FOREIGN PATENT DOCUMENTS

| WO | WO 99/36406 A1 | 7/1999 |
|---|---|---|
| WO | WO 00/47561 A1 | 8/2000 |
| WO | WO 02/070516 A2 | 9/2002 |
| WO | WO 03/020705 A1 | 3/2003 |
| WO | WO 2004/021969 A2 | 3/2004 |

*Primary Examiner* — Bernard Dentz
(74) *Attorney, Agent, or Firm* — Birch, Stewart, Kolasch and Birch, LLP

(57) ABSTRACT

Compounds of the formula Z: where; A is CH or N; $R_1$ is a substituent to a carbon atom in the ring containing A selected from —$S(=O)_p$Ra, where Ra is —$C_1$-$C_4$ alkyl, —ORx, —NRxRx, —NHNRxRx, —NHNHC(=O)ORx, —NRxOH; —C(=O)—Rb, where Rb is —CT-C4-alkyl, ORx, —NRxRx, —NHNRxRx, —NHC$_1$-$C_3$-alkyl-C(=O) Orx —NRxRc, where Rc is H, $C_1$-$C_4$ alkyl, —NRxRx; —C(=O)Rd, —CN, S(=O)pRx, where Rd is Rd is C1-C4-alkyl, —ORx, —NRxRx $C_1$-$C_3$-alkyl-O—C1-C3-alkylC (=O)ORx, —$C_1$-$C_3$-alkyl-COORx; —$C_1$-$C_3$alkyl-OH or $C_1$-$C_4$ alkyl ethers or esters thereof (O—$C_1$-$C_3$alkyl)q-O—Rx a 5 or 6 membered aromatic ring having 1-3 hetero atoms p is 1 or 2; Rx is independently selected from H, $C_1$-$C_4$ alkyl or acetyl; or a pair of Rx can together with the adjacent N atom form a ring; L is -0-, —$S(=O)$—, or —$CH_2$—, where r is 0, 1 or 2; $R_3$-$R_7$ are substituents as defined in the specification; X is —$(CR_8R_8')$n-D-$(CR_8R_8')$m-; D is a bond, —$NR_9$—, -0-, —S—, —$S(=0)$- or —$S(=0)_2$-; and pharmaceutically acceptable salts and prodrugs thereof, have utility as HIV antivirals.

(I)

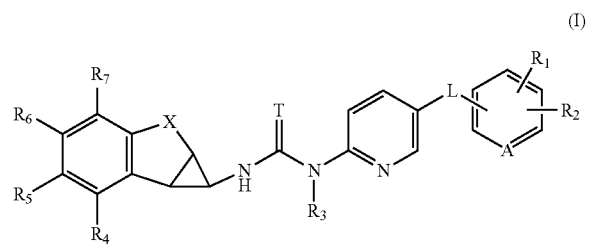

39 Claims, No Drawings

NON-NUCLEOTIDE REVERSE TRANSCRIPTASE INHIBITORS

This application is a national phase under 35 U.S.C §371 of PCT International Application No. PCT/SE2004/002034 which has an International filing date of Dec. 30, 2004, which designated the United States of America. In addition, this application claims priority to Application No.: 0400021-2 filed in Sweden, which was filed on Jan. 8, 2004 and Application No.: 0400585-6, filed in Sweden, which was filed on Mar. 9, 2004.

TECHNICAL FIELD

This invention relates to non-nucleoside reverse transcriptase inhibitors (NNRTIs) active against HIV-1 and having an improved resistance and pharmacokinetic profile. The invention further relates to novel intermediates in the synthesis of such compounds and the use of the compounds in antiviral methods and compositions.

BACKGROUND TO THE INVENTION

Our earlier filed PCT applications WO02/070516 & WO03/020705 claim novel NNRTIs of the formula I

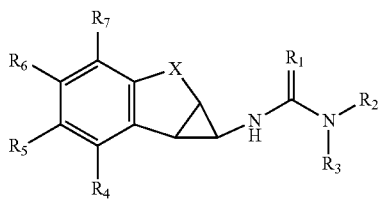

where;
$R_1$ is O, S;
$R_2$ is an optionally substituted, nitrogen-containing heterocycle, such as pyridyl;
$R_3$ is H, $C_1$-$C_3$ alkyl,
$R_4$-$R_7$ are independently selected from H, $C_1$-$C_6$ alkyl, $C_2$-$C_6$ alkenyl, $C_2$-$C_6$ alkynyl, halo$C_1$-$C_6$ alkyl, $C_1$-$C_6$ alkanoyl, halo$C_1$-$C_6$ alkanoyl, $C_1$-$C_6$ alkoxy, halo$C_1$-$C_6$ alkoxy, $C_1$-$C_6$ alkyloxy$C_1$-$C_6$ alkyl, halo$C_1$-$C_6$ alkyloxy$C_1$-$C_6$ alkyl, hydroxy$C_1$-$C_6$ alkyl, amino$C_1$-$C_6$ alkyl, carboxy$C_1$-$C_6$ alkyl, cyano$C_1$-$C_6$ alkyl, amino, carboxy, carbamoyl, cyano, halo, hydroxy, keto and the like;
X is —(CH$_2$)$_n$-D-(CH$_2$)$_m$— or X is —(CRaRb)$_c$—
D is —NR$_8$—, —O—, —S—, —S(=O)— or —S(=O)$_2$—
$R_8$ is H, $C_1$-$C_3$ alkyl
$R_a$ and $R_b$ are independently H, $C_1$-$C_3$ alkyl, OH or $R_a$ and $R_b$ together are =O
n and m are independently 0 or 1;
c is 1, 2 or 3
and pharmaceutically acceptable salts and prodrugs thereof.
Example 20 of WO 02/070516 discloses the compound

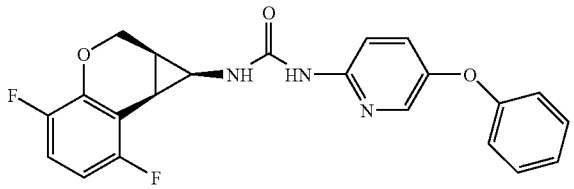

which is stated to have an ED$_{50}$ of 7 nM against wild type HIV (HIV$_{IIIB}$).

Our co-pending, but as of the priority date unpublished PCT application WO 04/021969 discloses compounds generally of the formula I above, but wherein $R^2$ is pyrid-2-yl substituted at the 5 position with a group of the formula —(CHR$_{11}$)$_p$-E-(CHR$_{11}$)$_q$—R$_{10}$ where E is E is —CH$_2$—, —CHOH—, —C=O—, —NR$_9$—, —O—, —S—, —S(=O)$_2$—;
p and q are independently 0, 1 or 2, where p+q≦2;
$R_{10}$ is a monocyclic ring which is optionally substituted with halo, cyano, morpholinomethyl- or morpholinoketo-; and
$R_{11}$ is independently H, $C_1$-$C_3$ alkyl, halo substituted $C_1$-$C_3$alkyl or hydroxy.

Although the urea and thiourea NNRTIs disclosed in the above documents are exquisitely active against reverse transcriptase, especially that of HIV-1, the nature of the HIV virus with its extreme lack of replicative fidelity and consequent tendency to rapid resistance development prompts a demand for further antiretroviral agents with enhanced antiviral performance against problematic drug escape mutants, notably at the RT 100, 103 and/or 181 positions.

BRIEF DESCRIPTION OF THE INVENTION

In accordance with a first aspect of the invention there are provided compounds of the formula Z:

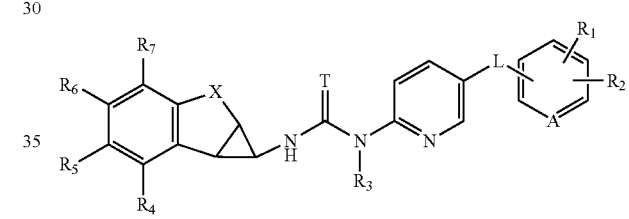

where;
A is CH or N;
$R_1$ is a substituent to a carbon atom in the ring containing A selected from
—S(=O)$_p$Ra,
where Ra is —$C_1$-$C_4$ alkyl, —ORx, —NRxRx, —NHNRxRx, —NHNHC(=O)ORx, —NRxOH;
—C(=O)—Rb,
where Rb is —$C_1$-$C_4$-alkyl, ORx, —NRxRx, —NRxN-RxRx, —NHC$_1$-$C_3$-alkyl-C(=O)ORx;
—NRxRc,
where Rc is H, $C_1$-$C_4$ alkyl, —NRxRx; —C(=O)Rd, —CN,
S(=O)$_p$Rx
where Rd is Rd is $C_1$-$C_4$-alkyl, —ORx, —NRxRx —$C_1$-$C_3$-alkyl-O—$C_1$-$C_3$alkylC(=O)ORx;
—$C_1$-$C_3$-alkyl-COORx;
—$C_1$-$C_3$alkyl-OH or $C_1$-$C_4$ alkyl ethers or esters thereof;
—(O—$C_1$-$C_3$alkyl)$_q$-O—Rx;
a 5 or 6 membered aromatic ring having 1-3 hetero atoms;
p and q are independently selected from 1 or 2;
Rx is independently selected from H, $C_1$-$C_4$ alkyl, or acetyl;
or a pair of Rx can together with the adjacent N atom form a pyrrolidine, piperidine, piperazine or morpholine ring;
$R_2$ is a substituent to a carbon atom in the ring containing A and is H, halo, cyano, $C_1$-$C_4$-alkyl, halo$C_1$-$C_4$-alkyl;
L is —O—, —S(=O)$_r$— or —CH$_2$—, where r is 0, 1 or 2;
$R_3$ is H, $C_1$-$C_3$ alkyl;

$R_4$-$R_7$ are independently selected from H, $C_1$-$C_6$ alkyl, $C_2$-$C_6$ alkenyl, $C_2$-$C_6$ alkynyl, halo$C_1$-$C_6$ alkyl, $C_1$-$C_6$ alkanoyl, halo$C_1$-$C_6$ alkanoyl, $C_1$-$C_6$ alkoxy, halo$C_1$-$C_6$ alkoxy, $C_1$-$C_6$ alkyloxy$C_1$-$C_6$ alkyl, halo$C_1$-$C_6$ alkyloxy$C_1$-$C_6$ alkyl, hydroxy$C_1$-$C_6$ alkyl, amino$C_1$-$C_6$ alkyl, carboxy$C_1$-$C_6$ alkyl, cyano$C_1$-$C_6$ alkyl, amino, carboxy, carbamoyl, cyano, halo, hydroxy, keto;

X is —$(CR_8R_8')_n$-D-$(CR_8R_8')_m$—;

T is O or S;

D is a bond, —$NR_9$—, —O—, —S—, —S(=O)— or —S(=O)$_2$—;

n and m are independently 0, 1 or 2, provided that they are not both 0 when D is a bond;

$R_8$ and $R_8'$ are independently H, $C_1$-$C_3$ alkyl, halo$C_1$-$C_3$alkyl, hydroxy, or $R_8$ and $R_8'$ together with their adjacent C atom is —C(=O)—

$R_9$ is independently H, $C_1$-$C_3$ alkyl;

and pharmaceutically acceptable salts and prodrugs thereof, with the proviso that $R_1$ as —C(=O)Rb is not morpholinoketo.

The currently preferred value for T is O, that is a urea derivative, although T as S (ie a thiourea derivative) is also highly potent.

The currently preferred value for $R_3$ is H.

Preferably $R_4$ is hydrogen, halo, halo$C_1$-$C_3$alkyl, or hydroxy, especially fluoro.

Preferably $R_5$ is halo, $C_{1-3}$ alkylcarbonyl, halo$C_1$-$C_3$alkyl, $C_{1-3}$alkyloxy or H, especially fluoro and most preferably H.

Preferably $R_6$ is hydrogen, halo, halo$C_1$-$C_3$alkyl, $C_1$-$C_3$alkyloxy, C1-3alkylcarbonyl, cyano or ethynyl, especially methoxy or fluoro and most preferably H.

Preferably $R_7$ is hydrogen, halo$C_1$-$C_3$alkyl, halo, $C_{1-3}$alkyloxy, or $C_{1-3}$alkylcarbonyl, most preferably fluoro.

Preferably $R_5$ and $R_6$ are H and $R_4$ and $R_7$ are halo, most preferably both are fluoro. Alternative preferred configurations include those wherein $R_5$ and $R_6$ are H, $R_4$ is fluoro and $R_7$ is acetyl or cyano.

A convenient value for at least one of $R_4$-$R_7$ is halo$C_1$-$C_3$alkyl, such as —$CF_2H$, —$CFH_2$, —$CH_2CF_3$ or —$CF_2CF_3$, and especially —$CF_3$.

Favoured —S(=O)$_p$Ra groups for $R^1$ include those wherein p is 2 or especially 1, and wherein Ra is alkyl, such as cyclopropyl, methylcyclopropyl, and most preferably methyl. Preferred groups thus include methylsulphonyl or methylsulphinyl Additional favoured —S(=O)$_p$NRxRx groups include those wherein Rx are each H or Me or wherein one is H and the other is Me, cyclopropyl or methylcyclopropyl, most preferably $NH_2$. Preferred groups thus include sulphonamide.

Favoured —C(=O)—Rb groups for $R_1$ include those where Rb is NRxRx or NHNRxRx, especially N-methylcarboxamide, hydrazinocarbonyl and —C(=O)NHNHC(=O)Me. Additional preferred —C(=O)—Rb groups include —C(=O)NRx'-N-morpholine, —C(=O)N Rx'-N-piperidine, —C(=O)NRx'-N-pyrrolidine, —C(=O)NRx'-N-piperazine, where Rx is methyl, acetyl or preferably H.

Favoured —NRxRc groups for $R_1$ include those wherein Rx is H or Me and those wherein Rc is —C(=O)Rd, where Rd is alkyl and S(=O)$_p$Rx, especially cyclopropylamide and acetamide.

Favoured —$C_1$-$C_3$-alkyl-COORx groups for $R_1$ include carboxyethyl and $C_1$-$C_2$ alkyl esters thereof.

Favoured —$C_1$-$C_3$alkyl-ORx groups for $R_1$ include hydroxyethyl and $C_1$-$C_2$ alkyl ethers and esters thereof.

Favoured —(O—$C_1$-$C_3$alkyl)$_q$-O—Rx groups for $R_1$ include ethoxy containing species especially 2-(methoxyethoxy)ethoxy.

Exemplary heteroatomic rings for $R_1$ include furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, thiazolyl, thiazolidinyl, isothiazolyl, isothiazolidinyl, especially 5 membered rings such as thiazolyl, thiadiazolyl, pyrazolyl, diazolyl and most preferably triazolyl.

The currently preferred value for L is —O—.

The compounds of formula Z may be administered as a racemic mixture, but preferably the cyclopropyl moiety intermediate the (thio)urea function, X and the phenyl ring (denoted Y below) is at least 75% such as around 90% enantiomerically pure with respect to the conformation:

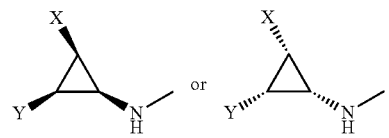

Preferred optical isomers of the compounds of formula I show a negative optical rotation value. Such isomers, for example when X is —O—$CH_2$—, tend to elute less rapidly from a chiral chromatogram, for example chiral AGP 150×10 mm, 5 μm; Crom Tech LTD Column, flow rate 4 ml/min, mobile phase 89 vol % 10 mM HOAc/$NH_4$OAc in acetonitrile. On the basis of preliminary x-ray crystallography analysis a presently favoured absolute configuration appears to be:

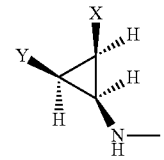

The currently preferred value for D is —O—. Convenient values for n and m include 1:0 and 1:1. Preferred values of n:m include 0:2 and especially 0:1, that is a chroman derivative. Conveniently each $R_8$ and $R_8'$ is H. Alternatively, in the case where n is 0 and m is 1, $R_8$ is advantageously H and $R_8'$ is OH.

Particularly preferred compounds have stereochemistry corresponding (1S,1aR,7bR)-1,1a,2,7b-tetrahydrocyclopropa[c]chromen-1-yl. For the sake of clarity, it is noted that the structure:

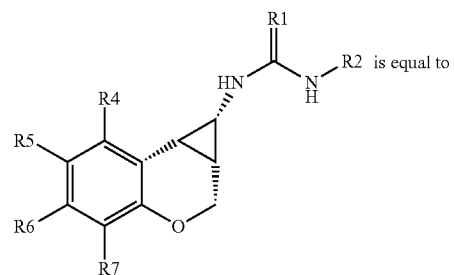

is equal to

-continued

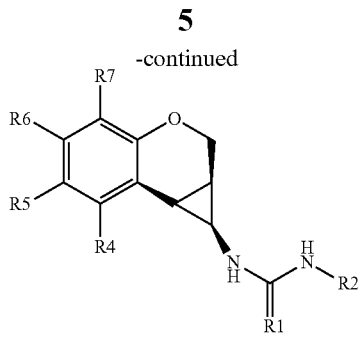

The expression $C_1$-$C_n$ alkyl where n is 3 or 4 or lower alkyl includes such groups as methyl, ethyl, n-propyl, isopropyl, cyclopropyl, n-butyl, s-butyl, t-butyl, cyclopropyl, methylcyclopropyl and the like. The term halo refers to chloro, bromo, fluoro and iodo, especially fluoro. $C_1$-$C_n$ alkoxy refers to groups such as methoxy, ethoxy, propoxy, cyclopropoxy, t-butoxy and the like. $C_2$-$C_n$ alkenyl refers to groups such as vinyl, 1-propen-2-yl, 1-buten-4-yl, 1-penten-5-yl, 1-buten-1-yl and the like. $C_1$-$C_n$ alkylthio includes methylthio, ethylthio, t-butylthio and the like. $C_1$-$C_n$ alkanoyloxy includes acetoxy, propionoxy, formyloxy, butyryloxy and the like. $C_2$-$C_n$ alkenoxy includes ethenyloxy, propenyloxy, iso-butoxyethenyl and the like. Halo$C_1$-$C_n$ alkyl (including complex substituents comprising this moiety such as halo$C_1$-$C_n$ alkyloxy) includes alkyls as defined herein substituted 1 to 3 times by a halogen including trifluoromethyl, 2-dichloroethyl, 3,3-difluoropropyl and the like. The term amine includes groups such as $NH_2$, NHMe, $N(Me)_2$ which may optionally be substituted with halogen, $C_1$-$C_7$ acyloxy, $C_1$-$C_6$ alkyl, $C_1$-$C_6$ alkoxy, nitro, carboxy, carbamoyl, carbamoyloxy, cyano, methylsulphonylamino and the like. Carboxy, carboxymethyl and carbamoyl include the corresponding pharmaceutically acceptable $C_1$-$C_6$ alkyl and aryl esters.

Prodrugs of the compounds of formula I are those compounds which following administration to a patient release a compound of the formula I in vivo. Typical prodrugs are pharmaceutically acceptable ethers and especially esters (including phosphate esters) when any of $R_4$-$R_7$ or $R^1R^2$ represent an hydroxy function, pharmaceutically acceptable amides or carbamates when any of the $R^1$ substituent or $R_4$-$R_7$ represent an amine function or pharmaceutically acceptable esters when the $R^1$, $R_2$ substituent or $R_4$-$R_7$ represent a carboxy function. Pharmaceutically acceptable esters include alkyl esters, including acetyl, ethanoyl, butyryl, t-butyryl, and pivaloyl, phosphate esters and sulphonic esters (ie those derived from $RSO_2OH$, where R is lower alkyl or aryl). Pharmaceutically acceptable esters include lower alkyl ethers and the ethers disclosed in WO00/47561, especially methoxyaminoacyl and ethoxyaminoacyl.

The compounds of formula Z can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Hydroxy protecting group as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, fo acetate, propionate, benzoate and the like.

Similarly, N-protecting group as used herein refers to those conventional N-protecting groups disclosed in Greene, "Protective Groups in Organic Synthesis", John Wiley & Sons New York 1981.

The invention further provides pharmaceutical compositions comprising the compounds of the invention and pharmaceutically acceptable carriers or diluents therefor. Additional aspects of the invention provide methods for the inhibition of HIV comprising administering a compound of the formula Z to a subject afflicted with or exposed to HIV-1. The HIV-1 may comprise a drug escape mutant, such as HIV strain comprising the mutations at the 100, 103 and/or 181 mutations, especially the K103N and/or L100I mutants.

The invention also extends to the use of the compounds of formula Z in therapy, such as in the preparation of a medicament for the treatment of HIV infections.

In treating conditions caused by HIV, the compounds of formula Z are preferably administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500-750 mg, in one to four dosage units per day. As with all pharmaceuticals, dosage rates will vary with the size and metabolic condition of the patient as well as the severity of the infection and may need to be adjusted for concomitant medications.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, DAPD, alovudine, abacavir, adefovir, adefovir dipivoxil, xbis-POC-PMPA, GW420 867X, foscarnet, hydroxyurea, Hoechst-Bayer HBY 097, efavirenz, trovirdine, MIV-150, capravirine, nevirapine, delaviridine, tipranavir, emtricitabine, PFA, H2G (omaciclovir), MIV-606 (valomaciclovir stearate), TMC-126, TMC-125, TMC-120, efavirenz, DMP-450, loviride, ritonavir, (including kaletra), lopinavir, saquinavir, lasinavir, indinavir, amprenavir, amprenavir phosphate, nelfinavir and the like, typically at molar ratios reflecting their respective activities and bioavailabilities. Generally such ratio will be of the order of 25:1 to 1:25, relative to the compound of formula I, but may be lower, for instance in the case of cytochrome p450 antagonists such as ritonavir.

Compounds of the invention are typically prepared as follows:

Scheme 1

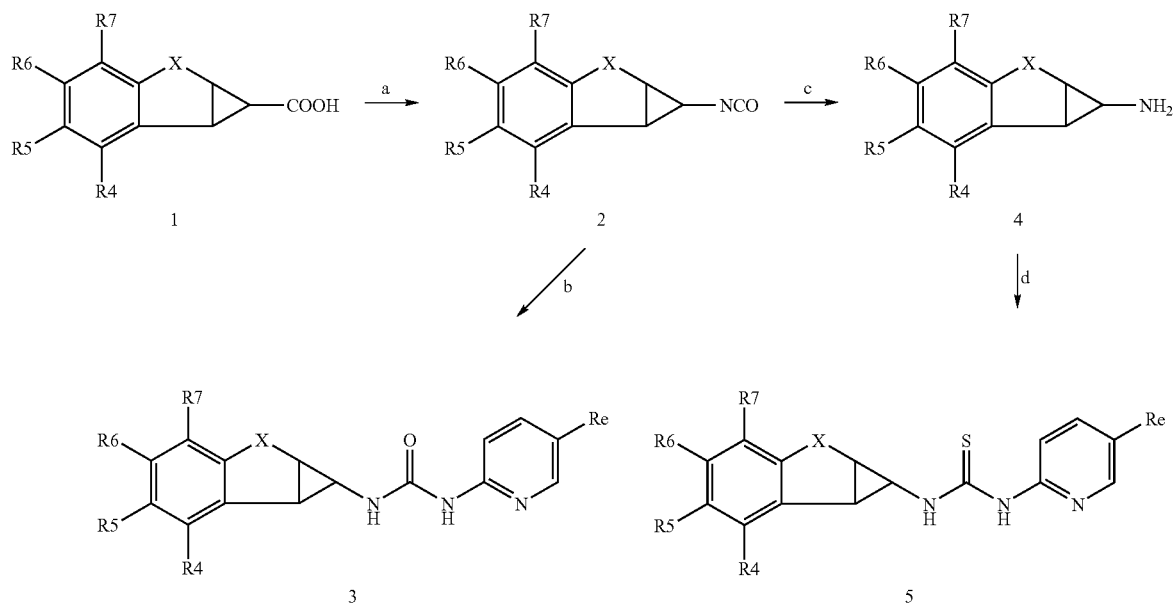

(a) DPPA, Et$_3$N, toluene; (b) substituted 2-aminopyridine; (c) aqueous HCl, dioxane; (d) substituted 2-pyridyl isothiocyanate.

Compounds of the general formula (I), wherein T is O (urea) or S (thiourea), Re is the (substituted) oxyphenyl or oxypyridyl moiety, or the thio, sulphine, sulphone or methylene analogue of such ethers and $R_3$ is H, are prepared by methods shown in Scheme 1. The cyclopropanecarboxylic acid 1-Scheme-1 is converted to the acyl azide and heated to 120° C. to induce Curtius rearrangement and provide the isocyanate 2-Scheme-1. The urea 3-Scheme-1 is obtained by coupling of the isocyanate with the relevantly substituted 2-aminopyridine. Hydrolysis of the isocyanate as in step (c) which results in the cyclopropylamine 4-Scheme-1, followed by reaction with a 2-pyridyl isothiocyanate provides the thiourea 5-Scheme-1. The isothiocyanate may be prepared from the optionally ring substituted 2-aminopyridine by known methods, such as treatment with thiophosgene or thiocarbonyldiimidazole. $R_3$ variants of formula I are prepared correspondingly using the appropriately amine-substituted aminopyridine ie 2-(N-methylamino)pyridine for $R_3$ as methyl. Many 2-aminopyridines are commercially available and others are described in literature or readily derivable therefrom, for example those shown in Scheme 2. T=S compounds can alternatively be prepared from the isothiocyanate corresponding to 2-Scheme 2A or from amine 3,3a-Scheme 2 and amino-$R_2$ in conjunction with an RC(=S)R' both as described in WO 9303022.

Scheme 2A

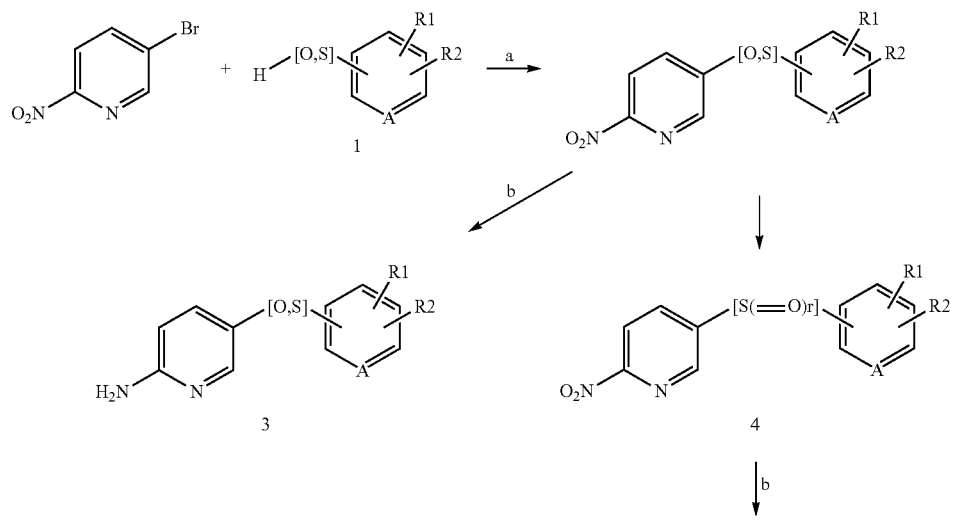

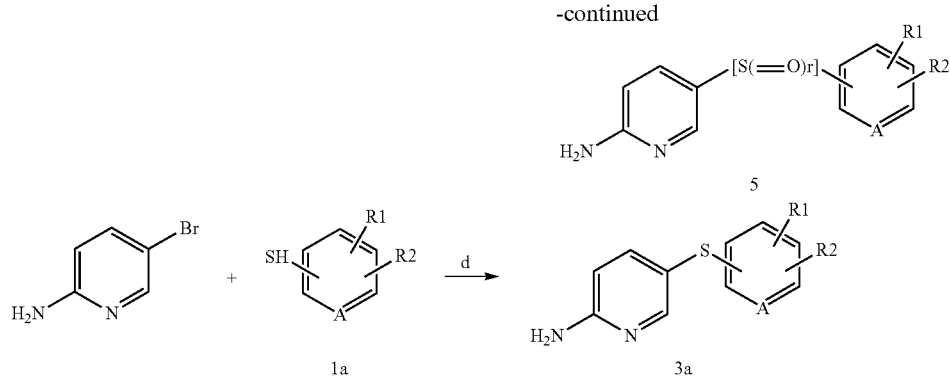

(a) base, DMF, heat; (b) reduction; (c) oxidation; (d) base, Cu catalyst, heat

The preparation of suitable 5-O— or 5-S-substituted-2-aminopyridines are outlined in Scheme 2A. 1-Scheme-2A with appropriate $R^1$ and $R^2$ substituents, or precursors (synthons) to these substituents, is reacted in step (a) with 5-bromo-2-nitropyridine and a base, such as NaH or $Cs_2CO_3$, to afford replacement of the bromine and give the nitro compound 2-Scheme-2A. The nitro group is then reduced to the amine in step (b), typically by hydrogenation at atmospheric pressure in the presence of catalysts such as Pd or Raney nickel. Transformation of precursors to the desired $R^1$, $R^2$ substituents can be done on the nitro compound 2-Scheme-2A before the reduction step (b). In the case of the sulfanyl 2-Scheme-2A, different oxidizing agents, for example hydrogen peroxide, convert the sulfide group to $S=(O)_r$ in step (c), followed by reduction of the nitro group to give 5-Scheme-2A. The thio compounds 3a-Scheme-2A may also be prepared directly as in step (d) by coupling 2-amino-5-bromopyridine with the thiol 1a-Scheme-2A in the presence of copper catalysts, for example by heating at 150° C. with Cu or CuI in DMF with a base such as $K_2CO_3$.

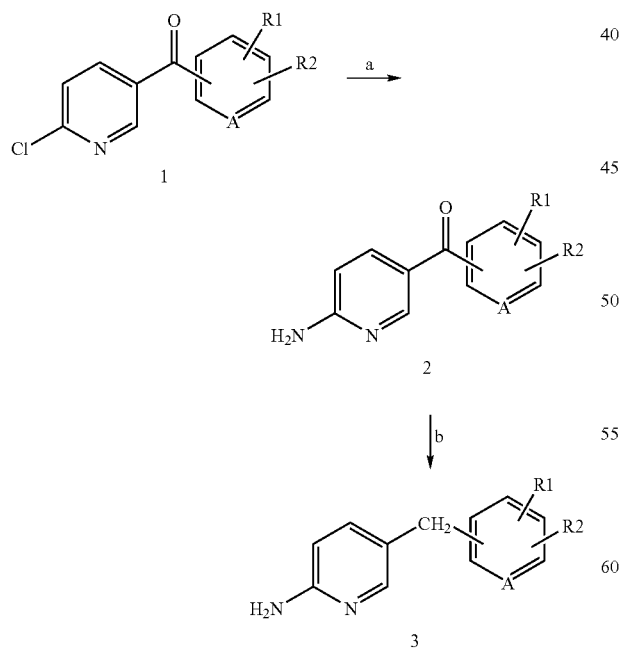

(a) $NH_3$, EtOH, heat; (b) $Et_3SiH$, TFA, $H_2SO_4$

The preparation of suitable 5-substituted methyl-2-aminopyridines are outlined in Scheme 2B. The methanone 1-Scheme-2B with appropriate $R^1$ and $R^2$ substituents, or precursors (synthons) to these substituents, is reacted in step (a) with ammonia to afford replacement of the chlorine and give the amino compound 2-Scheme-2B. The keto group is then reduced to $CH_2$ in step (b) to give 3-Scheme-2B.

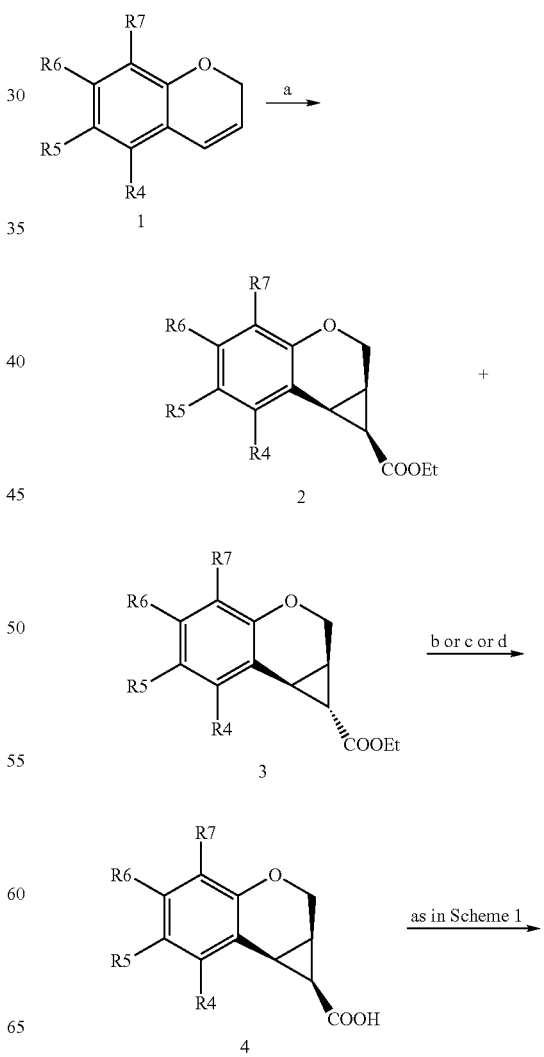

-continued

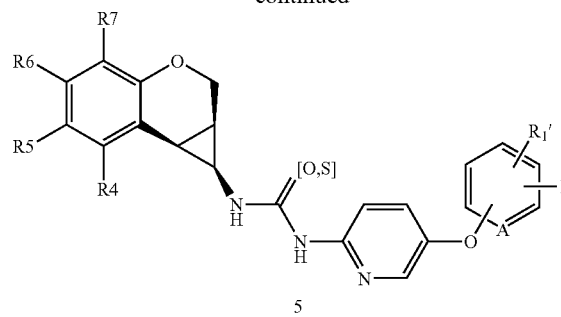

5

(a) ethyl diazoacetate, catalyst, CH₂Cl₂;
(b) chromatography and then reflux with LiOH, H₂O, MeOH;
(c) reflux with LiOH, H₂O, MeOH and then chromatography;
(d) rt, NaOH, H₂O, MeOH and then reflux with LiOH, H₂O, MeOH Compounds of the general formula (I), wherein T is O (urea) or S (thiourea), $R^{1'}$, and $R^{2'}$, are $R^1$ and $R^2$, protected as necessary with conventional hydroxyl, carboxy of amino protecting groups, or conventional synthons for $R^1/R^2$, $R^3$ is H, X is -D-CH₂, and wherein the cyclopropyl moiety has the relative configuration

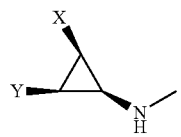

are prepared by methods shown in Scheme 3. Cyclopropanation of the double bond in the chromene 1-Scheme-3 with ethyl diazoacetate is catalyzed by cuprous or rhodium(II) salts such as CuI, (CuOTf)₂-benzene, and Rh₂(OAc)₄ in solvents such as dichloromethane, 1,2-dichloroethane, or chloroform. The reaction provides a diastereomeric mixture of the cyclopropanecarboxylic acid ethyl esters 2-Scheme-3, with the all cis relative configuration, and its trans isomer 3-Scheme-3. Separation by column chromatography of the cis and trans diastereomers may be accomplished at this stage, followed by hydrolysis of the isolated 2-Scheme-3, such as by refluxing in aqueous methanolic LiOH, to yield a racemic mixture of the all cis cyclopropanecarboxylic acid 4-Scheme-3, as described in step (b). Alternatively, the diastereomeric mixture of ethyl esters may be subjected to hydrolysis, and separation conducted on the mixture of cyclopropanecarboxylic acids to provide the isolated all cis isomer, as in step (c). Step (d) involves isolation of the cis ethyl ester 2-Scheme-3 which may also be done by selective hydrolysis of the trans 3-Scheme-3 at lower temperatures, such as treatment with aqueous methanolic NaOH at ambient temperature. The isolated cis ethyl ester may then be hydrolyzed in the usual manner to the cyclopropanecarboxylic acid 4-Scheme-3. The cyclopropanecarboxylic acid is subjected to the methods outlined in Scheme 1 to obtain the urea or thiourea 5-Scheme-3. The chromenes 1-Scheme-3 are prepared by methods shown in Schemes 4, 5, and 6.

Although this scheme 3 has been illustrated with a D=O variant it will be apparent that corresponding manipulations will be available to the D=S, S=O; S(=O)₂ and D=NR₈ variants. When R₈ is H, the nitrogen is typically protected with a conventional secondary amine protecting group, such as those described in Greene & Wuts Protective Groups in Organic Synthesis 2$^{nd}$ ed, Wiley NY 1991).

Scheme 4

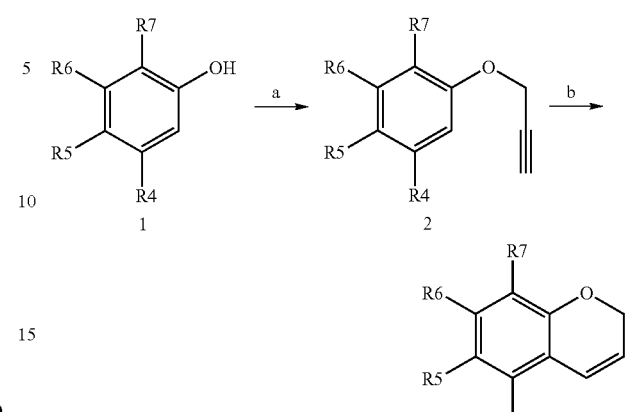

(a) 3-bromopropyne, K₂CO₃, acetone; (b) N,N-diethylaniline or PEG-200, 225° C.

Scheme 4 describes the preparation of chromenes, including many from commercially available disubstituted phenols, such as those wherein the substitution pattern in the benzene ring is as follows: $R^4$ and $R^7$ are halo; $R^4$ and $R^6$ are halo; $R^5$ and $R^7$ are halo; $R^4$ is halo and $R^7$ is $C_{1-3}$ alkylcarbonyl; and $R^4$ is hydroxy while $R^5$ is $C_{1-3}$ alkylcarbonyl. Reaction of the available disubstituted phenol 1-Scheme-4 with 3-bromopropyne in the presence of a base, such as K₂CO₃ in acetone or NaH in DMF, results in nucleophilic substitution of the halide to provide the ether 2-Scheme-4. Ring closure may be accomplished by heating the ether in N,N-dimethylaniline or polyethylene glycol to yield the chromene 3-Scheme-4.

Scheme 5

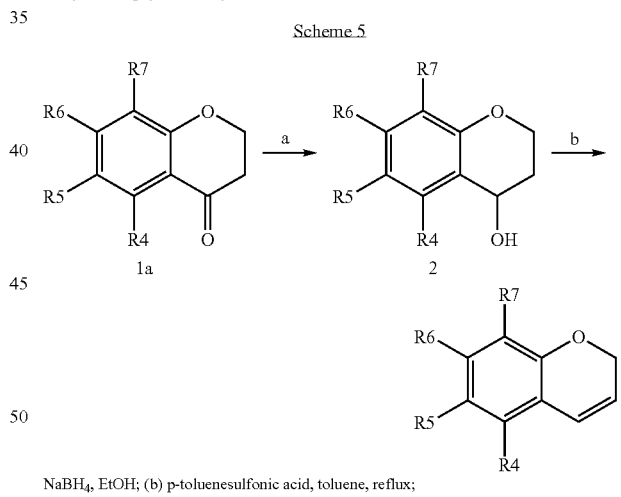

NaBH₄, EtOH; (b) p-toluenesulfonic acid, toluene, reflux;

Scheme 5 describes the preparation of chromenes, used as starting material in Scheme 3, from the appropriately substituted chromanones, which are readily accessed from commercially available chromanones, for example those wherein one of the positions in R₄ to R₇ is substituted with halo or $C_{1-3}$ alkoxy. Conversion of the carbonyl group in 4-chromanone 1a-Scheme-5 and to the corresponding alcohol by a suitable reducing agent such sodium borohydride in ethanol provides 2-Scheme-5. Refluxing the alcohol with small amounts of acid, such as p-TsOH in toluene, causes dehydration of 2-Scheme-5 to the desired chromene 1-Scheme-3. Corresponding manipulations will be available for other D variants. For example the corresponding 2H-1-benzothiopyran is readily prepared from commercially available (substituted) thiochroman-4-ones by reaction with a reductant such as a metal hydride for example lithium aluminium hydride in an organic solvent such as ether, followed by dehydration such as refluxing with an acid for example potassium acid sulphate or the like.

Pd(0) catalyzed coupling of the triflate 1-Scheme-7 leads to the replacement of the trifluoromethanesulfonyloxy group and the introduction of other substitutents at $R_6$. Thus, Scheme 7 provides the preparation of synthesis intermediates for use in scheme 3 to give the urea or thiourea 5-Scheme-3 wherein $R_6$ is cyano, ethynyl, or $C_{1-3}$ alkylcarbonyl.

Scheme 6

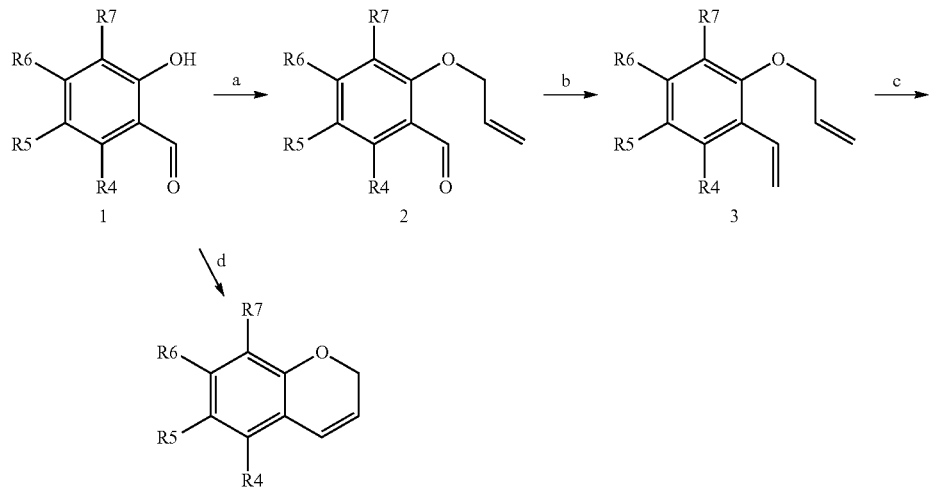

(a) allyl bromide, $K_2CO_3$, acetone; (b) $Ph_3PCH_3Br$, NaH, THF; (c) $Cl_2[Pcy_3]_2Ru=CHPh$, $CH_2Cl_2$ (d) $Ph_3P^+CH=CH_2Br^-$, DBU Chromenes, for use as starting material in Scheme 3, are prepared from substituted o-hydroxybenzaldehydes as shown by methods outlined in Scheme 6. Reaction of 1-Scheme-6 with allyl bromide in the presence of a base, such as $K_2CO_3$ in acetone, results in nucleophilic substitution of the halide to provide the ether 2-Scheme-6. Witting reaction transforms the aldehydic group into the olefin and provides 3-Scheme-6. The pair of terminal double bonds may undergo metathesis intramolecularly by treatment with a catalyst such as the ruthenium complex Grubb's catalyst in step (c) to produce the chromene. Alternatively 1-Scheme-6 can be cyclised directly as shown in step d) in the legend above.

Scheme 7

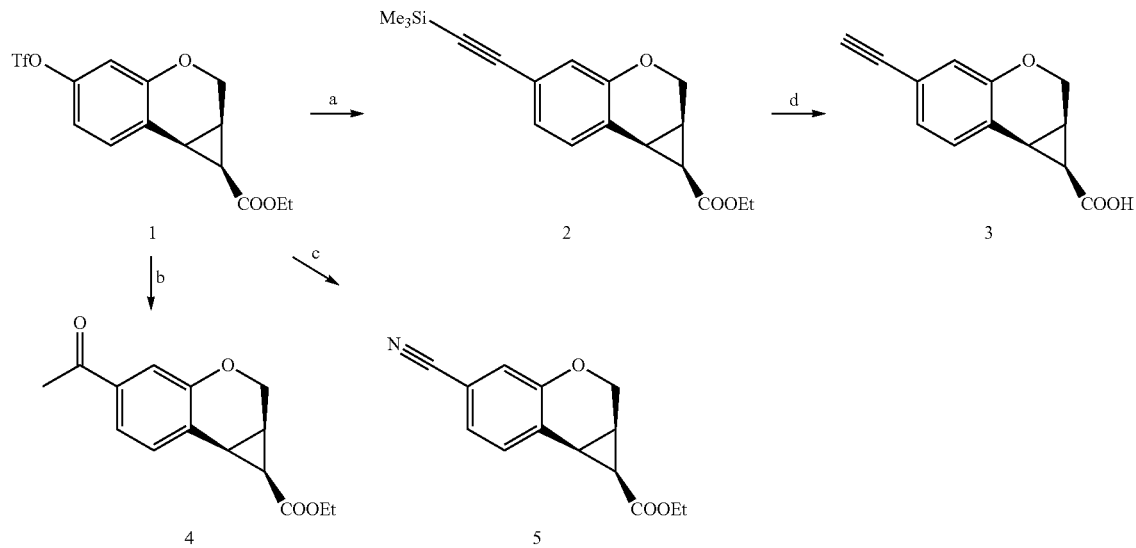

(a) Pd(0), DPPP, $Et_3N$, $(CH_3)_3SiC=CH$; (b) Pd(0), butyl vinyl ether, DMF; (c) Pd(0), $Zn(CN)_2$, DMF; (d) NaOH, $H_2O$, MeOH

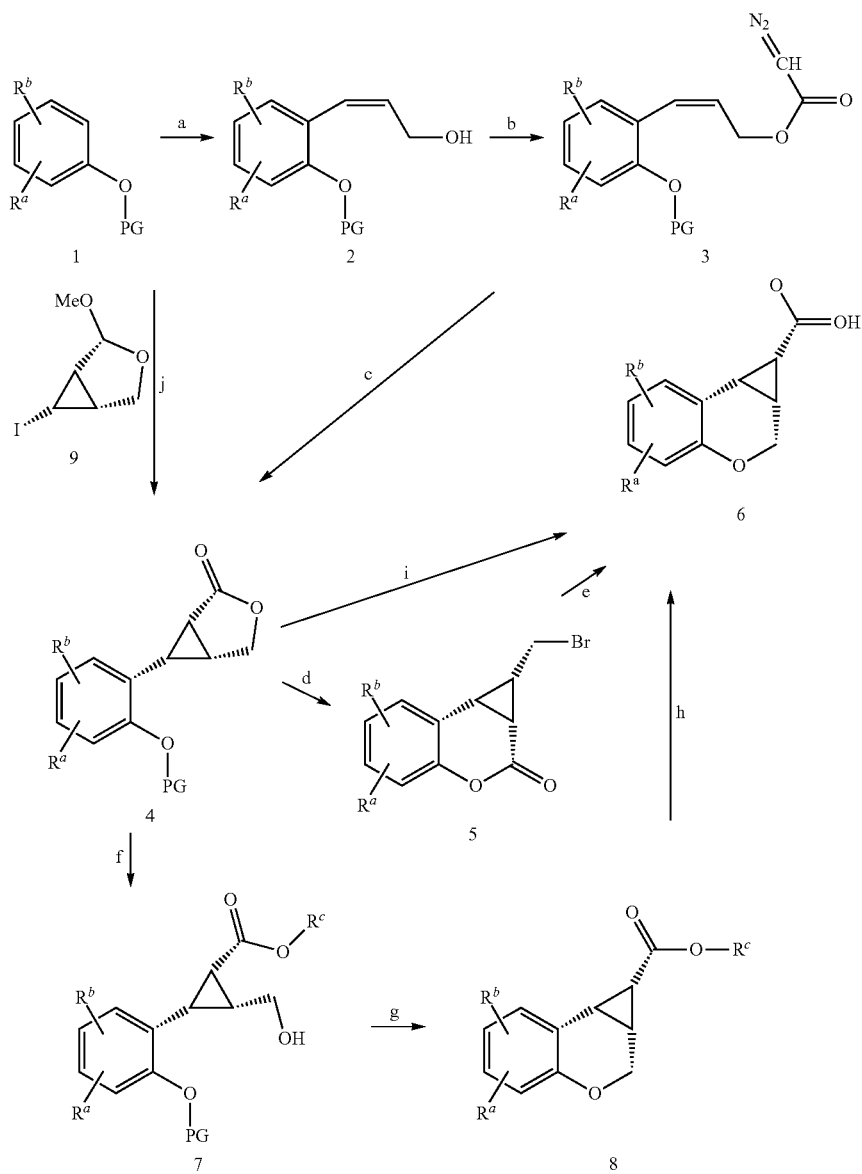

(a) BuLi/ZnCl₂, THF; Pd(OAc)₂, BrCH=CHCOOEt; DIBAL
(b) TsNHN=CHCOCl; PhNMe₂, NEt₃, CH₂Cl₂
(c) Rh₂(5-R-MEPY)₄, abs degassed dichloromethane
(d) 30% HBr, AcOH
(e) NaOH, H₂O
(f) NaOH; CO₂; I-PrI/DMSO
(g) IPrOH, HCl; DEAD, PPh₃, THF
(h) NaOH, MeOH:H₂O
(i) 1. BBr₃, CH₂Cl₂ 2. CH₃CN 3. NaOH, water
(j) 1. BuLi/ZnCl₂, THF; Pd(OAc) 2. cpd 9-Scheme-8 3. Jones reagent (chromic acid, sulfuric acid in acetone)

Convenient routes to compounds wherein X is —CH₂—O— are depicted in Scheme 8, where $R^a$ and $R^b$ are optional substituents $R_4$-$R_7$, which are suitably protected with conventional protecting groups as necessary and $R^c$ is a lower alkyl ester. Optionally substituted phenol 1-Scheme-8 which is hydroxy-protected with a protecting group such as methyl, MOM and the like is reacted with a base such as BuLi or the like in a solvent such as THF or the like and transformed to zinc salt by adding zinc chloride or the like. A catalyst such as Pd(OAc)₂ or the like is added along with an activated acrylate such as lower alkyl-cis-3-haloacrylate, for example BrCH=CHCOOEt or the like. The reaction mixture is cooled and a reducing agent such as DIBAL or the like is added portionwise and quenched to yield 2-Scheme-8. A hydrazone such as the p-toluenesulfonylhydrazone of glyoxylic acid chloride or the like and a base such as N,N-dimethylaniline or the like is added in a solvent such as CH₂Cl₂ or the like followed by the addition of another base such as Et₃N or the like to yield 3-Scheme-8. The reaction product is dissolved in a solvent such as dichloromethane or the like which is preferably degassed. A chiral Doyle's catalyst such as Rh₂(5-R-MEPy)₄ (U.S. Pat. No. 5,175,311, available from Aldrich or Johnson Matthey), or the like is added to yield 4-Scheme-8 in a high enantiomeric excess such as greater than 80, preferably greater than 90% ee. Preferably, this compound is first reacted with BBr₃ in dichloromethane followed by the addition of acetonitrile the reaction mixture and finally sodium hydroxide is added to give 6-Scheme-8. Alternatively, this product (4-Scheme-8) is ring-opened with an electrophile preferably HBr or the like under in conjunction with an acid such as AcOH or the like. Under acid conditions a spontaneous ring closure takes place to form chromenone 5-Scheme-8. When subjected to basic conditions such as NaOH or the like, the chromenone rearranges to form the chromen cyclopropyl carboxylic acid 6-Scheme-8. Alternatively, 4-Scheme-8, for instance when the phenolic protecting group is MOM, can be subjected to basic conditions such as NaOH, carbon dioxide and a lower alkyl halide such as iPrI in a solvent such as DMSO to open the lactone and yield the alkyl ester 7-Scheme-8. Displacement of the hydroxy protecting group and ring closure with the free hydroxymethyl moiety occurs in acidic conditions such as iPrOH/HCl or the like followed by DEAD; PPH₃ in an organic solvent such as THF or the like. Alternatively, in a convergent approach, compound 1-Scheme-8 is reacted with BuLi and transformed to a zinc salt. This salt reacted with the cyclopropyliodide, 9-Scheme-8, in a palladium-catalyzed reaction to give after reaction with Jone's reagent compound 4-Scheme-8. This carboxylic acid is in turn converted to the isocyanate as shown in Scheme 1 and subsequently to the heteroarylurea or heteroarylthiourea of the Formula Z.

$R_3$ variants of formula Z are prepared correspondingly using the appropriately amine-substituted (substituted) pyridoxy or phenyloxypyridine ie 5-substituted-2-(N-methylamino)pyridine derivatives for $R_3$ as methyl.

Compounds wherein X is an optionally substituted alkylene are conveniently prepared by scheme 9:

Scheme 9

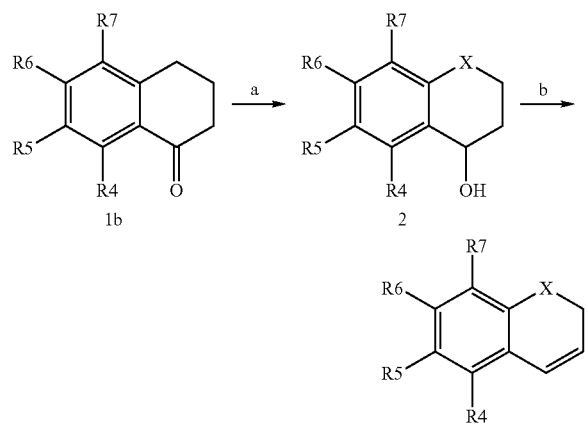

(a) NaBH₄, EtOH; (b) p-toluenesulfonic acid, toluene, reflux;

Scheme 9 describes the preparation of tetralins, indanes and homologues, used as starting material in the schemes above from known monosubstituted tetralones etc, wherein positions $R_4$ to $R_7$ is/are substituted, for example with halo or $C_{1-3}$ alkoxy. Conversion of the carbonyl group in 1-tetralone 1b-Scheme-9 to the corresponding alcohol by a suitable reducing agent such sodium borohydride in ethanol provides 2-Scheme-9. Refluxing the alcohol with small amounts of acid, such as p-TsOH in toluene, causes dehydration of 2-Scheme-9 to the desired tetralin 1-Scheme-9. Corresponding reactions are applicable to n=1 or 3.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula Z or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

DETAILED DESCRIPTION

Various aspects of the invention will now be illustrated by way of example only with reference to the following non-limiting examples.

Example 1

N-[(1S,1aR,7bR)-4,7-difluoro-1,1a,2,7b-tetrahydro-cyclopropa[c]chromen-1-yl]-N'-[5-(4-(sulfonamido)phenoxy)-2-pyridinyl]urea a) 5-(4-(N-t-butylsulfonamido)phenoxy)-2-nitropyridine

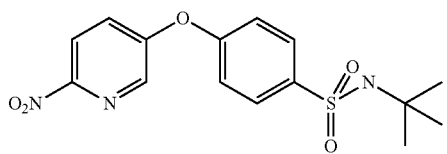

To a solution of 4-hydroxy-(N-t-butyl)benzenesulfonamide (3.01 g, 13.2 mmol) in DMF (48 ml), cesium carbonate (5.67 g, 17.4 mmol) was added, followed by addition of 5-bromo-2-nitro pyridine (2.36 g, 11.6 mmol) and the mixture was stirred at 50° C. for 12 hours. The suspension was filtered and the solvent evaporated and then the residue extracted between sat. aq. NaHCO$_3$ and methylene chloride. The organic phase was dried over sodium sulfate and evaporated. The resulting mixture was purified by column chromatography on silica gel (0-½-1% EtOH/methylene chloride gradient) to give 3.47 g material of which about 70% was the title compound (LC-MS, API-ES$^+$: 352.4; Calc. 351.38) and about 30% was 2-(4-(N-t-butylsulfonamido)phenoxy)-5-bromopyridine (LC-MS, API-ES$^+$: 386.3; Calc. 385.24) as a side product.

$^1$H-NMR (CDCl$_3$): 8.37 (d, 1H), 8.31 (d, 1H), 7.98 (d, 2H), 7.54 (dd, 1H), 7.20 (d, 2H), 4.51 (s 1H), 1.28 (s, 9H).

b) 5-(4-(N-t-butylsulfonamido)phenoxy)-2-pyridinamine

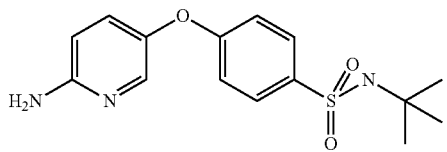

The product mixture obtained in Example 1a (3.47 g) was dissolved in ethanol (70 ml) and ethyl acetate (18 ml). Then 10% palladium on charcoal (680 mg) was added and the black suspension was hydrogenated with stirring under normal hydrogen pressure for 1½ hours. The catalyst was filtered off and the filtrate was evaporated. The resulting residue was purified by column chromatography on silica gel (0-10% EtOH/methylene chloride gradient) to give 2.42 g of title compound (57% yield over two steps) (LC-MS, API-ES$^+$: 322.0; Calc. 320.41)

$^1$H-NMR (d$_6$-DMSO): 7.77 (d, 1H), 7.73 (d, 2H), 7.20 (dd, 1H), 7.39 (s, 1H), 7.25 (dd, 1H), 6.99 (d, 2H), 6.50 (d, 1H), 5.97 (br, s 1H), 1.06 (s, 9H).

c) N-[(1S,1aR,7bR)-4,7-difluoro-1,1a,2,7b-tetrahydrocyclopropa[c]chromen-1-yl]-N'-[5-(4-(N-t-butylsulfonamido)phenoxy)-2-pyridinyl]urea

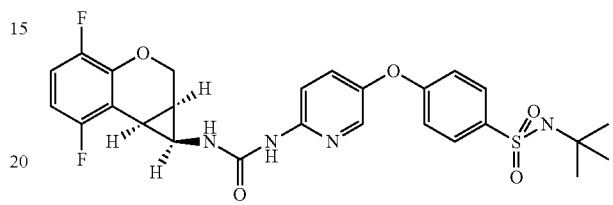

(1S,1aR,7bS)-4,7-difluoro-1,1a,2,7b-tetrahydrocyclopropa[c]chromene-1-carboxylic acid, prepared as shown in WO02/705163 (68 mg, 0.301 mmol), 5-(4-(N-t-butylsulfonamido)phenoxy)-2-pyridinamine (109 mg, 0.0.341 mmol) and triethylamine (47 µl, 0.341 mmol) were mixed together in dry toluene (2 ml) and argon atmosphere was introduced. Then DPPA (74 µl, 0.341 mmol) was added and the reaction solution was stirred at 110° C. for 3 hours. The reaction mixture was worked up by extractions between methylene chloride and 5% citric acid followed by sat. aq. NaHCO$_3$. Silica gel column chromatography (1-2% EtOH/methylene chloride gradient) gave 143 mg of material which was further purified by preparative TLC chromatography (10% MeOH/CHCl$_3$) to finally give 100 mg of pure product as a white powder (61% yield). (LC-MS, API-ES$^+$: 545.0; Calc. 544.48).

$^1$H-NMR (CDCl$_3$): 9.29 (br s, 1H), 7.85 (d, 2H), 7.64 (d, 1H), 7.62 (s, 1H), 7.29 (dd, 1H), 6.96 (d, 2H), 6.79 (d tr, 1H), 6.70 (d, 1H), 6.59 (d tr, 1H), 4.52 (s, 1H), 4.47 (dd, 1H), 4.33 (dd, 1H), 3.79 (q, 1H), 2.62 (tr, 1H), 1.98 (m, 1H), 1.26 (s, 9H).

d) N-[(1S,1aR,7bR)-4,7-difluoro-1,1a,2,7b-tetrahydrocyclopropa[c]chromen-1-yl]-N'-[5-(4-(sulfonamido)phenoxy)-2-pyridinyl]urea

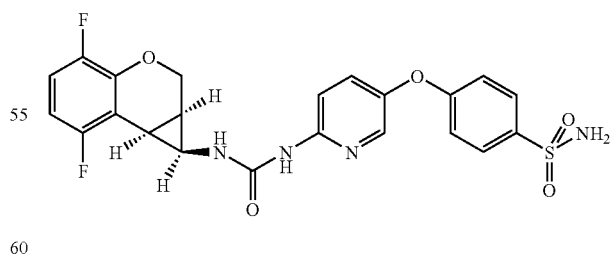

Dried N-[(1S,1aR,7bR)-4,7-difluoro-1,1a,2,7b-tetrahydrocyclopropa[c]chromen-1-yl]-N'-[5-(4-(N-t-butylsulfonamido)phenoxy)-2-pyridinyl]urea (36 mg, 0.066 mmol) was dissolved in 1% triflic acid/acetonitrile solution (5.8 ml) and the reaction solution was stirred for 30 minutes at room temperature. The reaction was quenched with a small amount of pyridine and the acetonitrile was removed by evaporation.

The residue was worked up by extractions between methylene chloride and sat. aq. NaHCO₃. The organic phase was dried through sodium sulfate was evaporated. Silica gel column chromatography (1-4% EtOH/methylene chloride gradient) gave 26 mg of pure product as white powder (71% yield).

¹H-NMR (d₆-DMSO): 9.41 (s, 1H), 8.06 (br, s 1H), 7.77 (d, 2H), 7.73 (d, 1H), 7.52 (dd, 1H), 7.32 (d, 1H), 7.29 (s, 1H), 7.05 (d, 2H), 6.79 (d tr, 1H), 7.02 (d tr, 1H), 4.32 (dd, 1H), 4.28 (dd, 1H), 3.51 (q, 1H), 2.47 (tr, 1H), 2.00 (m, 1H).

Example 2

N-[(1S,1aR,7bR)-4,7-difluoro-1,1a,2,7b-tetrahydro-cyclopropa[c]chromen-1-yl]-N'-[5-(4-(N-methylcarboxyamido)phenoxy)-2-pyridinyl]urea a) 5-(4-(N-methylcarboxyamido)phenoxy)-2-nitropyridine

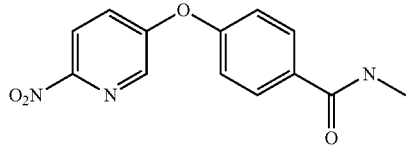

Potassium tert-butoxide (191 mg, 1.70 mmol) was added to a solution of 4-hydroxy-N-methylbenzamide (257 mg, 1.70 mmol) in DMF (2.5 ml) and the mixture was stirred for 1 hour at room temperature. Then the mixture was heated to 65° C. and 5-bromo-2-nitro pyridine (305 mg, 1.50 mmol) was added and the mixture was stirred at 65° C. for 12 hours. Then the solvent was evaporated and the residue extracted between water and methylene chloride. The organic phase was dried over sodium sulfate and evaporated. The resulting mixture was purified by column chromatography on silica gel (0-1½% EtOH/methylene chloride gradient) to give 358 mg of material of which about 60% was the title compound (LC-MS, API-ES⁺: 273.9; Calc. 273.25) and about 40% was 2-(4-(N-methylcarboxamido)phenoxy)-5-bromopyridine (LC-MS, API-ES⁺: 307.8, 308.8; Calc. 307.15) as a side product.

¹H-NMR (d₆-DMSO): 8.46 (br q, 1H), 8.45 (d, 1H), 8.34 (d, 1H), 7.93 (d, 2H), 7.71 (dd, 1H), 7.28 (d, 2H), 2.78, 2.77 (2×s, 3H).

b) 5-(4-(N-methylcarboxyamido)phenoxy)-2-pyridinamine

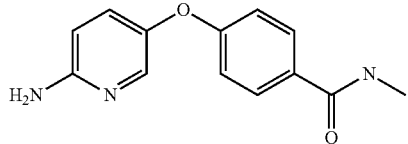

The product mixture obtained in step a) (358 mg) was dissolved in ethanol (10 ml). Then 10% palladium on charcoal (110 mg) was added and the black suspension was hydrogenated with stirring under normal hydrogen pressure for 1½ hours. The catalyst was filtered off and the filtrate was evaporated. The resulting residue was purified by column chromatography on silica gel (2-6% EtOH/methylene chloride gradient) to give 118 mg of title compound (32% yield over two steps) (LC-MS, API-ES⁺: 244.4; Calc. 243.27)

¹H-NMR (CDCl₃): 7.93 (d, 1H), 7.71 (d, 2H), 7.21 (dd, 1H), 7.25 (dd, 1H), 6.94 (d, 2H), 6.55 (d, 1H), 6.01 (br, s 1H), 4.41 (br s, 2H), 3.01 (2×s, 3H).

c) N-[(1S,1aR,7bR)-4,7-difluoro-1,1a,2,7b-tetrahydrocyclopropa[c]chromen-1-yl]-N'-[5-(4-(N-methylcarboxyamido)phenoxy)-2-pyridinyl]urea

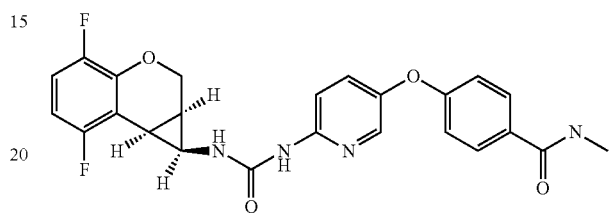

The title compound was synthesized analogously to Example 1 from 5-(4-(N-methyl carboxyamido)phenoxy)-2-pyridinamine (37 mg, 0.15 mmol). Silica gel column chromatography (0-2% EtOH/methylene chloride gradient) gave 41 mg of pure product as white powder (65% yield). (LC-MS, API-ES⁺: 467.1; Calc. 466.45).

¹H-NMR (CDCl₃): 9.33 (br s, 1H), 7.99 (s, 1H), 7.75 (d, 2H), 7.61 (d, 1H), 7.28 (dd, 1H), 6.93 (d, 2H), 6.78 (d tr, 1H), 6.72 (d, 1H), 6.57 (d tr, 1H), 6.07 (br q, 1H), 4.45 (dd, 1H), 4.33 (dd, 1H), 3.78 (q, 1H), 3.03 (d, 3H), 3.66 (tr, 2H), 2.61 (tr, 1H), 2.01-1.95 (m, 1H).

Example 3

N-[(1S,1aR,7bR)-4,7-difluoro-1,1a,2,7b-tetrahydrocyclopropa[c]chromen-1-yl]-N'-[5-(4-(N-methylsulfonamido)phenoxy)-2-pyridinyl]urea a) 5-(4-(N-methylsulfonamido)phenoxy)-2-nitropyridine

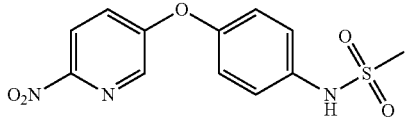

The title compound was synthesized analogously to Example 1a from N-(4-hydroxy phenyl)methanesulfonamide (150 mg, 0.802 mmol). Silica gel column chromatography (0-0.75% EtOH/methylene chloride gradient) gave 63 mg of material of which >90% was the title compound (LC-MS, API-ES⁺: 308.0; Calc. 307.25). (2-(4-(N-methylsulfonamido)phenoxy)-5-bromopyridine (LC-MS, API-ES⁺: 307.8, 308.8; Calc. 307.15) was formed as a side product).

¹H-NMR (d₆-DMSO): 8.52 (d, 1H), 8.36 (d, 1H), 7.85 (d, 2H), 7.83 (dd, 1H), 7.48 (q, 1H), 7.40 (d, 2H), 2.43, 2.42 (2×s, 3H).

b) 5-(4-(N-methylsulfonamido)phenoxy)-2-pyridinamine

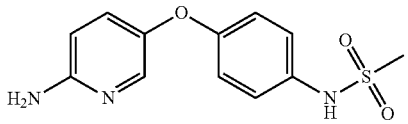

The title compound was synthesized analogously to Example 2b) from (5-(4-(N-methylsulfonamido)phenoxy)-2-nitropyridine (63 mg, 0.204 mmol). Filtration and evaporation gave 73 mg of crude product. (LC-MS, API-ES$^+$: 280.0; Calc. 279.34).

$^1$H-NMR (d$_6$-DMSO): 7.78 (d, 1H), 7.70 (d, 2H), 7.25 (dd, 1H), 7.02 (d, 2H), 6.50 (dd, 1H), 5.97 (s 1H), 2.37, 2.36 (2×s, 3H).

c) N-[(1S,1aR,7bR)-4,7-difluoro-1,1a,2,7b-tetrahydrocyclopropa[c]chromen-1-yl]-N'-[5-(4-(N-methylsulfonamido)phenoxy)-2-pyridinyl]urea

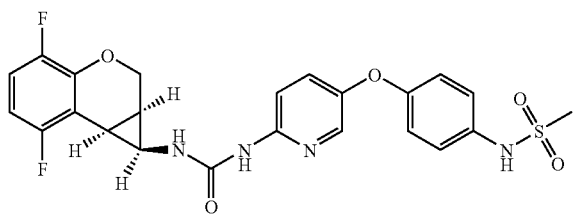

The title compound was synthesized analogously to Example 1c) from 5-(4-(N-methyl sulfonamido)phenoxy)-2-pyridinamine (76 mg, 0.204 mmol). Silica gel column chromatography (1-2½% EtOH/methylene chloride gradient) gave pure fractions containing 36 mg of pure product as white powder (40% yield). (LC-MS, API-ES$^+$: 503.0; Calc. 502.32).

$^1$H-NMR (CDCl$_3$): 9.47 (br s, 1H), 8.68 (s, 1H), 7.85 (s, 1H), 7.57 (d, 1H), 7.30-7.24 (m, 3H), 6.83-6.77 (m, 2H), 6.56 (d tr, 1H), 4.45 (dd, 1H), 4.32 (dd, 1H), 3.81 (q, 1H), 3.02 (s, 3H), 2.60 (tr, 1H), 1.99-1.93 (m, 1H).

Example 4

N-[(1S,1aR,7bR)-4,7-difluoro-1,1a,2,7b-tetrahydrocyclopropa[c]chromen-1-yl]-N'-[5-(4-aminophenoxy)-2-pyridinyl]urea a) 5-(4-(N-t-butoxycarbonylamino)phenoxy)-2-nitropyridine

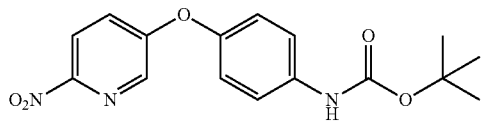

The title compound was synthesized analogously to Example 1a) from 4-(N-t-butoxy-carbonylamino)phenol (581 mg, 2.78 mmol). Silica gel column chromatography (0-2% EtOH/methylene chloride gradient) gave 704 mg of material of which about 50% was the title compound (LC-MS, API-ES$^+$: 332.0; Calc. 331.25). The other half consisted of (2-(4-(N-t-butoxycarbonylamino)phenoxy)-5-bromopyridine (LC-MS, API-ES$^+$: 364.9, 366.0; Calc. 363.15), which was formed as a side product.

$^1$H-NMR (d$_6$-DMSO): 9.47 (br s, 1H), 8.35 (d, 1H), 8.29 (d, 1H), 7.55 (d, 2H), 7.51 (dd, 1H), 7.15 (d, 2H), 1.47 (s, 9H).

b) 5-(4-(N-t-butoxycarbonylamino)phenoxy)-2-pyridinamine

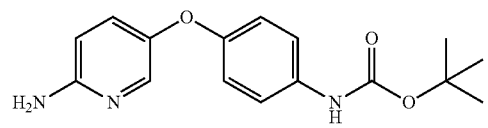

The title compound was synthesized analogously to Example 2b) from the mixture obtained from step a), containing (5-(4-(N-t-butoxycarbonylamino)phenoxy)-2-nitropyridine (total 704 mg). After the reaction, the resulting residue after filtration and evaporation was purified by column chromatography on silica gel (2-10% EtOH/methylene chloride gradient) to give 418 mg of title compound (57% yield over two steps) (LC-MS, API-ES$^+$: 302.0; Calc. 301.35)

$^1$H-NMR (CDCl$_3$): 7.69 (d, 1H), 7.32 (d, 2H), 7.31 (d, 1H), 6.90 (d, 2H), 6.68 (d, 1H), 6.47 (br, s 1H), 4.98 (br s, 2H), 1.51 (s, 9H).

c) N-[(1S,1aR,7bR)-4,7-difluoro-1,1a,2,7b-tetrahydrocyclopropa[c]chromen-1-yl]-N'-[5-(4-(N-t-butoxycarbonylamino)phenoxy)-2-pyridinyl]urea

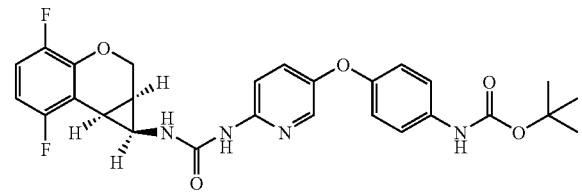

The title compound was synthesized analogously to Example 1c) from 5-(4-(N-t-butoxycarbonylamino)phenoxy)-2-pyridinamine (418 mg, 1.39 mmol). Silica gel column chromatography (1-4% EtOH/methylene chloride gradient) gave 479 mg of product as white powder (74% yield). (LC-MS, API-ES$^+$: 525.1; Calc. 524.30).

$^1$H-NMR (CDCl$_3$): 9.32 (br s, 1H), 7.34 (d, 2H), 7.20 (dd, 1H), 6.88 (d, 2H), 6.79 (d tr, 1H), 6.58 (d tr, 1H), 6.45 (s, 1H), 4.41 (dd, 1H), 4.34 (dd, 1H), 3.75 (q, 1H), 2.59 (tr, 1H), 1.98-1.93 (m, 1H), 1.52 (s, 9H).

d) N-[(1S,1aR,7bR)-4,7-difluoro-1,1a,2,7b-tetrahydrocyclopropa[c]chromen-1-yl]-N'-[5-(4-aminophenoxy)-2-pyridinyl]urea

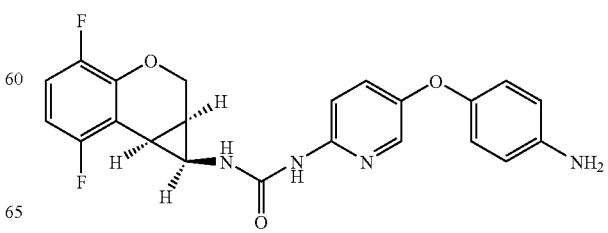

Dried N-[(1S,1aR,7bR)-4,7-difluoro-1,1a,2,7b-tetrahydrocyclopropa[c]chromen-1-yl]-N'-[5-(4-(N-t-butoxycarbonylamino)phenoxy)-2-pyridinyl]urea (242 mg, 0.46 mmol) was dissolved in methylene chloride (2 ml) and then 1M HCl/AcOH (4.6 ml) was added and the reaction solution was stirred for 60 minutes at room temperature. The volatile matters were removed by evaporation. The residue was worked up by extractions between methylene chloride and sat. aq. NaHCO$_3$. The organic phase was dried through sodium sulfate and evaporated. Silica gel column chromatography (1-3% EtOH/methylene chloride gradient) gave 139 mg of pure product as white powder (71% yield).

$^1$H-NMR (CDCl$_3$): 9.33 (br s, 1H), 7.44 (d, 1H), 7.24 (s, 1H), 7.17 (dd, 1H), 6.79 (d, 2H), 6.77 (d tr, 1H), 6.68 (d, 2H), 6.60-6.54 (m, 2H), 4.40 (dd, 1H), 4.35 (dd, 1H), 3.73 (q, 1H), 3.61 (br s, 2H), 2.57 (tr, 1H), 1.98-1.92 (m, 1H).

Example 5

N-[(1S,1aR,7bR)-4,7-difluoro-1,1a,2,7b-tetrahydrocyclopropa[c]chromen-1-yl]-N'-[5-(4-(methylsulfon)phenoxy)-2-pyridinyl]urea a) 5-(4-(methylsulfon)phenoxy)-2-nitropyridine

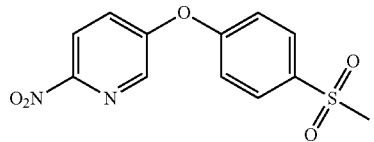

The title compound was synthesized analogously to Example 1a) from 4-hydroxyphenyl methyl sulfone (288 mg, 1.67 mmol). Silica gel column chromatography (0-2% EtOH/methylene chloride gradient) gave 300 mg of material with more than 90% of the title compound (LC-MS, API-ES$^-$: 353.0 (m+AcO$^-$); Calc. 294.29). A few percent of contaminating 2-(4-(methylsulfon)phenoxy)-5-bromopyridine (LC-MS, API-ES$^+$: 327.9, 330.0; Calc. 328.19) was present.

$^1$H-NMR (CDCl$_3$): 8.41 (d, 1H), 8.33 (d, 1H), 8.04 (d, 2H), 7.58 (dd, 1H), 7.27 (d, 2H), 3.10 (s, 3H).

b) 5-(4-(methylsulfon)phenoxy)-2-pyridinamine

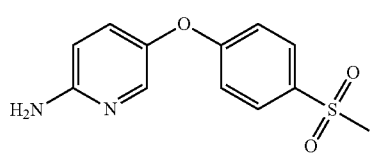

The title compound was synthesized analogously to Example 2b) from the mixture obtained from step a), containing (5-(4-(methylsulfon)phenoxy)-2-nitropyridine (300 mg). This material was dissolved with heating in a mixture of ethyl acetate (10 ml), isopropanol (3 ml) and methanol (3 ml). After the reaction, which was continued at room temperature, the resulting residue after filtration and evaporation was purified by column chromatography on silica gel (2-4% EtOH/methylene chloride gradient) to give a pure fraction containing 160 mg of title compound (LC-MS, API-ES$^+$: 265.0; Calc. 264.31).

c) N-[(1S,1aR,7bR)-4,7-difluoro-1,1a,2,7b-tetrahydrocyclopropa[c]chromen-1-yl]-N'-[5-(4-(methylsulfon)phenoxy)-2-pyridinyl]urea

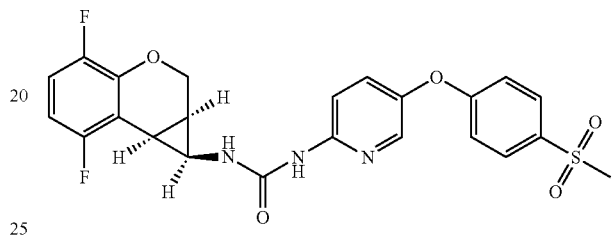

The title compound was synthesized analogously to Example 1c) from 5-(4-(methyl-sulfon)phenoxy)-2-pyridinamine (31 mg, 0.118 mmol). Silica gel column chromatography (1-3% EtOH/methylene chloride gradient) followed by preparative TLC (10% MeOH/CHCl$_3$) gave 10.7 mg of pure product as white powder (19% yield). (LC-MS, API-ES$^+$: 488.0; Calc. 487.48).

$^1$H-NMR (CDCl$_3$): 9.41 (br s, 1H), 8.99 (s, 1H), 7.91 (d, 2H), 7.68 (d, 1H), 7.31 (dd, 1H), 7.04 (d, 2H), 6.87 (d, 1H), 6.80 (d tr, 1H), 6.58 (d tr 1H), 4.48 (dd, 1H), 4.32 (dd, 1H), 3.82 (q, 1H), 2.62 (tr, 1H), 2.01-1.95 (m, 1H).

Example 6

N-[(1S,1aR,7bR)-4,7-difluoro-1.1a,2,7b-tetrahydrocyclopropa[c]chromen-1-yl]-N'-[5-(4-(2-hydroxyethyl)phenoxy)-2-pyridinyl]urea a) 5-(4-(2-hydroxyethyl)phenoxy)-2-nitropyridine

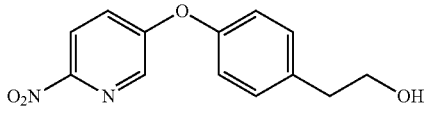

The title compound was synthesized analogously to Example 2a from 2-(4-hydroxy phenyl)ethylalcohol (234 mg, 1.70 mmol). Silica gel column chromatography (0-2% EtOH/methylene chloride gradient) gave 237 mg of material with more than 80% of the title compound (LC-MS, API-ES$^{31}$ : 319.0 (m+AcO$^-$); Calc. 260.25). About 10-15% of contaminating 2-(4-(2-hydroxyethyl)phenoxy)-5-bromopyridine (LC-MS, API-ES+: 294.0, 296.0; Calc. 295.25) was present.

b) 5-(4-(2-hydroxyethyl)phenoxy)-2-pyridinamine

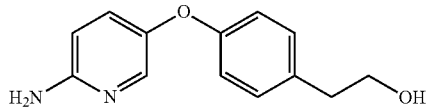

The title compound was synthesized analogously to Example 2b from the mixture obtained from step a), containing (5-(4-(2-hydroxyethyl)phenoxy)-2-nitropyridine (197 mg). The resulting residue after filtration and evaporation was purified by column chromatography on silica gel (2-10% EtOH/methylene chloride gradient) to give a pure fraction containing 65 mg of title compound (LC-MS, API-ES+: 231.1; Calc. 230.27).

c) N-[(1S,1aR,7bR)-4,7-difluoro-1,1a,2,7b-tetrahydrocyclopropa[c]chromen-1-yl]-N'-[5-(4-(2-hydroxyethyl)phenoxy)-2-pyridinyl]urea

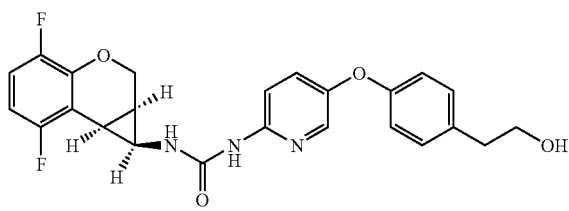

The title compound was synthesized analogously to Example 1c) from 5-(4-(2-hydroxyethyl)phenoxy)-2-pyridinamine (62 mg, 0.282 mmol). Silica gel column chromatography (0-4% EtOH/methylene chloride gradient) gave fractions, from which 8 mg of pure product as white powder was obtained, and additionally some mixed fractions (LC-MS, API-ES+: 454.2; Calc. 453.45).

¹H-NMR (CDCl₃): 9.38 (br s, 1H), 8.28 (s, 1H), 7.54 (d, 1H), 7.24 (dd, 1H), 7.20 (d, 2H), 6.88 (d, 2H), 6.77 (d tr, 1H), 6.71 (d, 1H), 6.56 (d tr, 1H), 4.43 (dd, 1H), 4.34 (dd, 1H), 3.87 (t, 2H), 3.77 (q, 1H), 2.86 (t, 2H), 2.59 (tr, 1H), 1.98-1.93 (m, 1H), 1.51 (br, 1H).

Example 7

N-[(1S,1aR,7bR)-4,7-difluoro-1,1a,2,7b-tetrahydrocyclopropa[c]chromen-1-yl]-N'-[5-(4-(2-(2-methoxyethoxy)ethoxy)phenoxy)-2-pyridinyl]urea a) 5-(4-(2-(2-methoxyethoxy)ethoxy)phenoxy)-2-nitropyridine

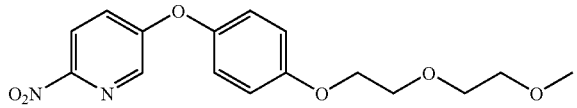

The title compound was synthesized analogously to Example 2a) from 4-(2-(2-methoxy-ethoxy)ethoxy)phenol (300 mg, 1.42 mmol). Silica gel column chromatography (0-½% EtOH/methylene chloride gradient) gave 173 mg of material with more than 70% of the title compound (LC-MS, API-ES+: 335.1; Calc. 334.33). About 20-30% of contaminating 2-(4-(2-(2-methoxyethoxy)ethoxy)phenoxy)-5-bromopyridine (LC-MS, API-ES+: 368.0, 370.0; Calc. 369.33) was present.

b) 5-(4-(2-(2-methoxyethoxy)ethoxy)phenoxy)-2-pyridinamine

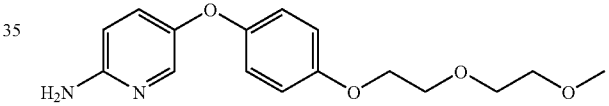

The title compound was synthesized analogously to Example 2b) from the mixture obtained from Example 22, containing 5-(4-(2-(2-methoxyethoxy)ethoxy)phenoxy)-2-nitro pyridine (173 mg). The resulting residue after filtration and evaporation was purified by column chromatography on silica gel (0-6% EtOH/methylene chloride gradient) to give a pure fraction containing 92 mg (60% yield) of title compound (LC-MS, API-ES+: 305.1; Calc. 304.35).

¹H-NMR (CDCl₃): 7.85 (d, 1H), 7.16 (dd, 1H), 6.90-6.85 (m, 4H), 6.68 (d, 1H), 6.50 (d, 1H), 4.40 (br, 2H), 4.11 (t, 2H), 3.85 (t, 2H), 3.72 (t, 2H), 3.58 (t, 2H), 3.39 (s, 3H).

c) N-[(1S,1aR,7bR)-4,7-difluoro-1,1a,2,7b-tetrahydrocyclopropa[c]chromen-1-yl]-N'-[5-(4-(2-(2-methoxyethoxy)ethoxy)phenoxy)-2-pyridinyl]urea

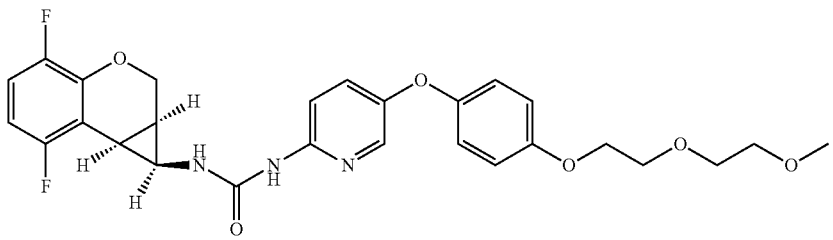

The title compound was synthesized analogously to Example 1c) from 5-(4-(2-(2-methoxyethoxy)ethoxy)phenoxy)-2-pyridinamine (46 mg, 0.15 mmol). Silica gel column chromatography (0-1½% EtOH/methylene chloride gradient) gave fractions, from which 14 mg of pure product as white powder was obtained, and additionally some mixed fractions (~40 mg) (LC-MS, API-ES+: 528.1; Calc. 527.53).

$^1$H-NMR (CDCl$_3$): 9.35 (br s, 1H), 7.82 (s, 1H), 7.48 (d, 1H), 7.18 (d, 1H), 6.89 (m, 4H), 6.77 (d tr, 1H), 6.63 (d, 1H), 6.57 (d tr 1H), 4.42 (dd, 1H), 4.35 (dd, 1H), 4.14 (t, 2H), 3.87 (t, 1H), 3.75 (q, 1H), 3.74 (t, 2H), 3.59 (t, 2H), 3.40 (s, 3H), 2.58 (tr, 1H), 1.98-1.92 (m, 1H).

Example 8

5-({6-[({[(1S,1aR,7bR)-4,7-difluoro-1,1a,2,7b-tetrahydrocyclopropa[c]chromen-1-yl]amino}carbonyl)amino]-3-pyridinyl}oxy)-N-methyl-2-pyridinecarboxamide a) N-methyl-5-[(6-nitro-3-pyridinyl)oxy]-2-pyridinecarboxamide

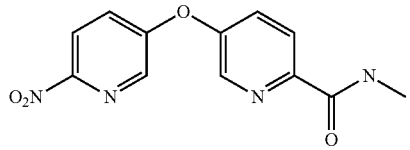

5-[(6-nitro-3-pyridinyl)oxy]-2-pyridinecarboxylic acid (260 mg, 1 mmol) was refluxed in thionyl chloride (10 ml) over-night. The excess thionyl chloride was evaporated and the crude acid chloride was quenched with aqueous methyl amine to give pure N-methyl-5-[(6-nitro-3-pyridinyl)oxy]-2-pyridinecarboxamide (190 mg, 70%)

$^1$H NMR (CDCl$_3$+MeOD): 8.4 (d, 1H), 8.32 (d, 1H), 8.31 (d, 1H), 7.42 (br s, 1H), 7.55 (m, 2H).

b) 5-({6-[({[(1S,1aR,7bR)-4,7-difluoro-1,1a,2,7b-tetrahydrocyclopropa[c]chromen-1-yl]amino}carbonyl)amino]-3-pyridinyl}oxy)-N-methyl-2-pyridinecarboxamide

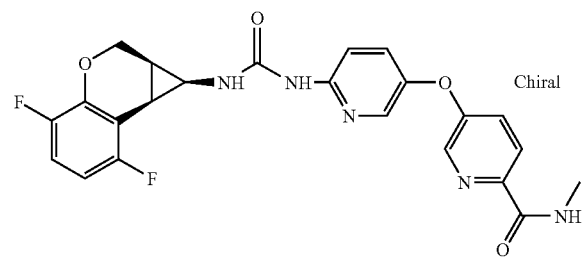

N-methyl-5-[(6-nitro-3-pyridinyl)oxy]-2-pyridinecarboxamide (190 mg, 0.7 mmol) was dissolved in Methanol (20 ml). The mixture was hydrogenated using Ra/Ni under hydrogen atmosphere. When the starting material was consumed according to TLC (ether), the mixture was filtrated through celite and concentrated under reduced pressure.

To the crude product was added (1S,1aR,7bS)-4,7-difluoro-1,1a,2,7b-tetrahydrocyclopropa[c]chromene-1-carboxylic acid (0.170 mg, 0.76 mmol) and the mixture was co-evaporated with Toluene (10 ml) to half the volume. Diphenylphosphoryl azide (179 µl, 0.76 mmol), and triethyl amine (106 µl, 0.76 mmol) was added. The mixture was then refluxed for 4 h under argon atmosphere. The solvent was then removed under reduced pressure and the crude product was dissolved in ethyl acetate and washed with small portions of aqueous hydrochloric acid (0.01M), saturated sodium hydrogen carbonate and water. Purification by flash chromatography (1% methanol in ether) gave the desired compound (158 mg, 48%).

$^1$H NMR (CDCl$_3$): 9.27 (br s, 1H), 8.25 (d, 1H), 8.17 (d, 1H), 8.16-8.10 (br s, 1H), 7.88-7.82 (m, 1H), 7.67 (d, 1H), 7.31 (dd, 1H), 7.26 (dd, 1H), 6.83-6.75 (m, 2H), 6.61-6.55 (m, 1H), 4.48 (dd, 1H), 4.32 (dd, 1H), 3.81 (q, 1H), 3.02 (d, 3H), 2.62 (t, 1H), 2.02-1.94 (m, 1H).

Example 9

4-({6-[({[(1S,1aR,7bR)-4,7-difluoro-1,1a,2,7b-tetrahydrocyclopropa[c]chromen-1-yl]amino}carbonyl)amino]-3-pyridinyl}oxy)benzamide a) 4-[(6-nitro-3-pyridinyl)oxy]benzamide

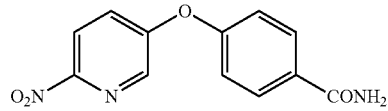

4-hydroxybenzamide (150 mg, 1.1 mmol) and caesium carbonate (394 mg, 1.21 mmol) was dissolved in dimethylformamide (7 ml). 5-bromo-2-nitropyridine (244 mg, 1.21 mmol) was then added. The mixture was left at 50 degrees until the starting material was consumed according to TLC (1% methanol in ether). Purification by flash chromatography yielded 4-[(6-nitro-3-pyridinyl)oxy]benzamide (110 mg, 38%)

$^1$H NMR (CDCl$_3$): 8.37 (d, 1H), 8.29 (d, 1H), 7.94 (m, 2H), 7.51 (dd, 1H), 7.18 (m, 2H).

b) 4-({6-[({[(1S,1aR,7bR)-4,7-difluoro-1,1a,2,7b-tetrahydrocyclopropa[c]chromen-1-yl]amino}carbonyl)amino]-3-pyridinyl}oxy)benzamide

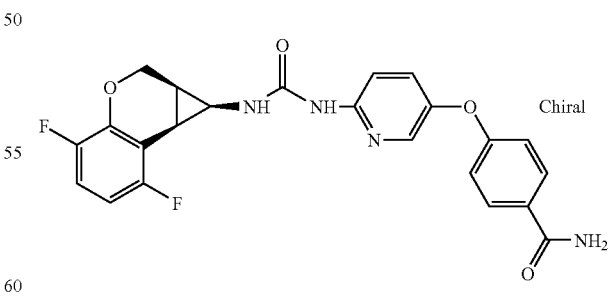

This compound was prepared essentially by the same procedure as described for Example 8, starting from 4-[(6-nitro-3-pyridinyl)oxy]benzamide (100 mg, 0.38 mmol) and (1S,1aR,7bS)-4,7-difluoro-1,1a,2,7b-tetrahydrocyclopropa[c]chromene-1-carboxylic acid (65 mg, 0.29 mmol) to give pure title compound 20 mg (12%).

1H NMR (CDCl3+MeOD): 7.82 (m, 2H), 7.63 (d, 1H), 7.30 (dd, 1H), 6.96 (d, 2H), 6.90-6.76 (m, 2H), 6.62-5.59 (m, 1H), 4.45 (dd, 1H), 4.35 (dd, 1H), 2.6 (t, 1H), 2.0-1.92 (m, 1H)

Example 10

5-({6-[({[(1S,1aR,7bR)-4,7-difluoro-1,1a,2,7b-tetrahydrocyclopropa[c]chromen-1-yl]amino}carbonyl)amino]-3-pyridinyl}oxy)-2-pyridinecarboxamide a) 5-[(6-nitro-3-pyridinyl)oxy]-2-pyridinecarboxamide

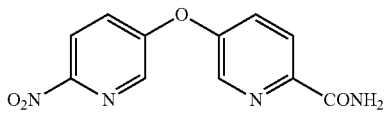

5-[(6-nitro-3-pyridinyl)oxy]-2-pyridinecarboxylic acid (100 mg, 1 mmol) was refluxed in thionyl chloride (5 ml) over-night. The excess thionyl chloride was evaporated and the crude acid chloride was quenched with aqueous methyl amine to give pure 5-[(6-nitro-3-pyridinyl)oxy]-2-pyridinecarboxamide (60 mg, 60%

$^1$H NMR (DMSO): 8.60 (d, 1H), 8.57 (d, 1H), 8.13 (s, 1H), 8.11 (br s, 1H), 7.67 (br s, 1H).

b) 5-({6-[({[(1S,1aR,7bR)-4,7-difluoro-1,1a,2,7b-tetrahydrocyclopropa[c]chromen-1-yl]amino}carbonyl)amino]-3-pyridinyl}oxy)-2-pyridinecarboxamide

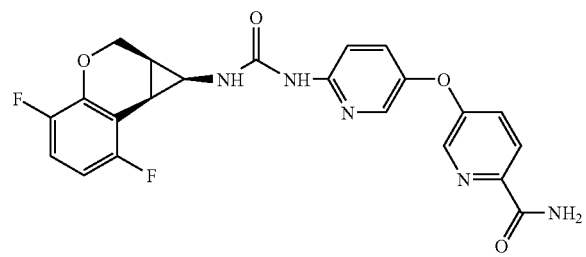

This compound was prepared essentially by the same procedure as described for Example 8, starting from 5-[(6-nitro-3-pyridinyl)oxy]-2-pyridinecarboxamide (60 mg, 0.38 mmol) and (1S,1aR,7bS)-4,7-difluoro-1,1a,2,7b-tetrahydrocyclopropa[c]chromene-1-carboxylic acid (65 mg, 0.29 mmol) to give pure title compound (18 mg (18%).

1H NMR (CDCl$_3$+MeOD): 9.35 (br s, 1H), 8.28 (d, 1H), 8.17 (d, 1H), 7.75 (br s, 1H), 7.69 (d, 1H), 7.33 (dd, 1H), 7.27 (dd, 1H), 6.96 (d, 1H), 6.8 (m, 1H), 6.58 (m, 1H), 4.48 (dd, 1H), 4.32 (dd, 1H), 3.80 (q, 1H), 2.62 (t, 1H), 2.02-1.96 (m, 1H).

Example 11

N-[(1S,1aS,7bS)-4,7-difluoro-1,1a,2,7b-tetrahydrocyclopropa[c]chromen-1-yl]-N'-{5-[4-(hydrazinocarbonyl)phenoxy]-2-pyridinyl}urea a) tert-butyl 2-[4-(benzyloxy)benzoyl]hydrazinecarboxylate

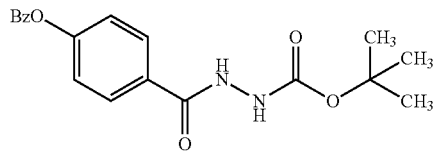

A mixture of 4-benzyloxybenzoic acid (0.780 g, 3.42 mmol), tert-butyl carbazate (0.443 g, 3.35 mmol), Et$_3$N (0.5 mL), 1-(3-dimethylaminopropyl)-3-ethylcarbodiimide hydrochloride (1.05 g, 5.47 mmol) and 1-hydroxybenzotriazole hydrate (0.778 g, 5.76 mmol) in N,N-dimethylformamide (27 mL) was stirred at room temperature for 2 days. The reaction was concentrated and diluted in dichloromethane. The organic phase was washed twice with water, dried with MgSO$_4$ and concentrated. The residue was purified on column chromatography (silica gel, 5% MeOH in CH$_2$Cl$_2$) and tert-butyl 2-[4-(benzyloxy)benzoyl]hydrazine carboxylate (0.998 g, yield: 85%) was identified by NMR spectroscopy.

$^1$H-NMR (CDCl$_3$): 8.21 (s, 1H), 7.76 (d, 2H), 7.37 (m, 5H), 6.95 (d, 2H), 6.76, (s, 1H), 5.08 (s, 2H), 1.48 (s, 9H).

b) tert-butyl 2-(4-hydroxybenzoyl)hydrazinecarboxylate

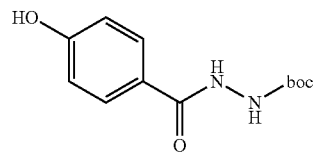

A solution of tert-butyl 2-[4-(benzyloxy)benzoyl]hydrazinecarboxylate (975 mg, 2.85 mmol) in presence of catalytic amount of Pd—C 10% in ethanol (40 mL) is hydrogenated for 3 hours. After filtration on celite, the residue is purified on column chromatography (silica gel, 10% MeOH in CH$_2$Cl$_2$) and tert-butyl 2-(4-hydroxybenzoyl)hydrazine carboxylate (0.688 g, yield: 96%) was identified by NMR spectroscopy.

$^1$H-NMR (CD$_3$OD): 7.73 (d, 2H), 6.82 (d, 2H), 4.84 (s, 2H), 1.48 (s, 9H)

c) tert-butyl 2-{4-[(6-nitro-3-pyridinyl)oxy]benzoyl}hydrazinecarboxylate

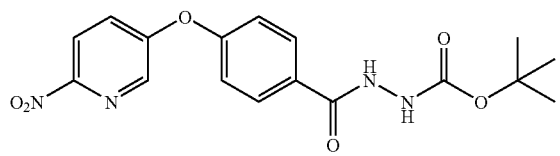

To a mixture of tert-butyl 2-(4-hydroxybenzoyl)hydrazinecarboxylate (0.688 g, 2.73 mmol) and 5-bromo-2-nitropyridine (0.554 mg, 2.73 mmol) and caesium carbonate (1.33 g, 4.08 mmol) in N,N-dimethylformamide (7 mL) was stirred overnight at 80° C. The solution was concentrated and the residue was taken with dichloromethane and water. The organic phase was dried on MgSO$_4$ and concentrated. The crude product was purified by column chromatography (silica gel, 5% MeOH in CH$_2$Cl$_2$), to give 736 mg of the mixture nitropyridine and bromopyridine.

d) tert-butyl 2-{4-[(6-amino-3-pyridinyl)oxy]benzoyl}hydrazinecarboxylate

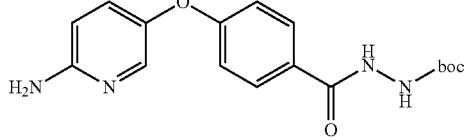

The mixture of the nitropyridine and bromopyridine (0.700 g) in presence of catalytic amount of Pd—C 10% in ethanol (20 mL) and EtOAc (20 mL) was hydrogenated for 1 hour. After filtration on celite, the residue was purified on column chromatography (silica gel, 5% MeOH in CH$_2$Cl$_2$) and tert-butyl 2-{4-[(6-amino-3-pyridinyl)oxy]benzoyl}hydrazinecarboxylate (0.326 g, yield: 35%) was identified by NMR spectroscopy.

$^1$H-NMR (CD$_3$OD): 7.73 (d, 2H), 6.64 (d, 1H), 7.17 (dd, 1H), 6.86 (dd, 2H), 6.55 (d, 1H), 4.74 (s, 4H), 1.39 (s, 9H).

e) tert-butyl 2-[4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)benzoyl]hydrazine carboxylate

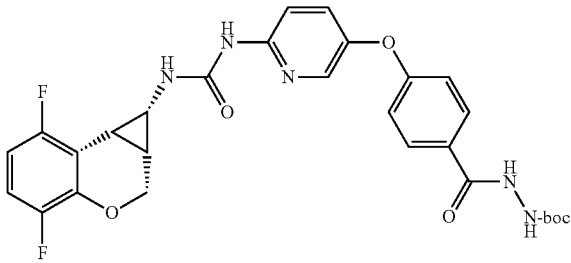

A mixture of the chiral acid (155 mg, 0.687 mmol), tert-butyl 2-{4-[(6-amino-3-pyridinyl)oxy]benzoyl}hydrazinecarboxylate (267 mg, 0.776 mmol), diphenylphosphoryl azide 0.162 mL, 0.756 mmol) and Et$_3$N (0.105 mL, 0.756 mmol) in toluene (10 mL) was refluxed for 4 hours. The solution was reduced and the residue was diluted in dichloromethane and washed once with HCl (0.001N) and brine. The organic phase was dried with MgSO$_4$ and evaporated. The residue was purified on column chromatography (silica gel, 5% MeOH in CH$_2$Cl$_2$) to give the title compound (0.227 g, yield: 52%).

$^1$H-NMR (CDCl$_3$): 9.36 (s, 1H), 9.05 (s, 1H), 8.99 (s, 1H), 7.80 (d, 2H), 7.62 (d, 1H), 7.28 (s, 1H), 7.25 (d, 1H), 6.89 (d, 1H), 6.86 (d, 2H), 6.78 (m, 1H), 6.55 (m, 1H), 4.43 (dd, 1H), 4.30 (dd, 1H), 3.76 (m, 1H), 2.59 (m, 1H), 1.95 (m, 1H), 1.46 (s, 1H).

f) N-[(1S,1aS,7bS)-4,7-difluoro-1,1a,2,7b-tetrahydrocyclopropa[c]chromen-1-yl]-N'-{5-[4-(hydrazinocarbonyl)phenoxy]-2-pyridinyl}urea

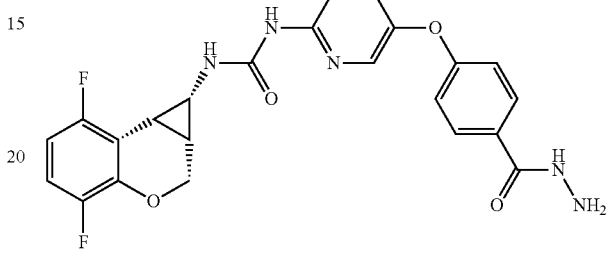

The tert-butyl 2-[4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)benzoyl]hydrazine carboxylate (49 mg, 0.089 mmol) in a mixture of dichloromethane (0.5 mL) and trifluoroacetic (0.5 mL) was stirred at room temperature for 30 min. The reaction was concentrated and purified on column chromatography (silica gel, 2% MeOH in CH$_2$Cl$_2$) to give the compound N-[(1S,1aS,7bS)-4,7-difluoro-1,1a,2,7b-tetrahydrocyclopropa[c]chromen-1-yl]-N'-{5-[4-(hydrazinocarbonyl)phenoxy]-2-pyridinyl}urea (17.6 mg, yield: 42%).

$^1$H-NMR (CD$_3$OD): 7.80 (d, 2H), 7.62 (d, 1H), 7.39 (dd, 1H), 6.97 (d, 3H), 6.83 (m, 1H), 6.62 (m, 1H), 4.41 (m, 1H), 4.29 (dd, 1H), 3.61 (m, 1H), 2.59 (t, 1H), 2.02 (m, 1H).

Example 12

4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)-N-cyclopropylbenzamide a) 4-(benzyloxy)-N-cyclopropylbenzamide

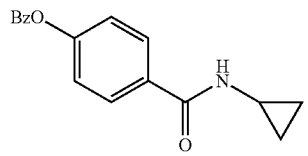

4-(benzyloxy)-N-cyclopropylbenzamide (0.774 g, 83%) was synthesized analogously to Example 11a from 4-benzyloxybenzoic acid (0.759 g).

$^1$H-NMR (CDCl$_3$): 7.70 (d, 2H), 7.38 (m, 5H), 6.97 (d, 2H), 6.17 (s, 1H), 5.10 (s, 2H), 2.88 (m, 1H), 0.85 (m, 2H), 0.6 (m, 2H).

b) N-cyclopropyl-4-hydroxybenzamide

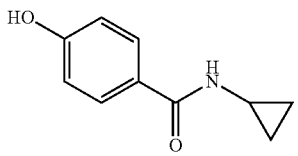

N-cyclopropyl-4-hydroxybenzamide (0.332 g, 68%) was synthesized analogously to Example 11b from 4-(benzyloxy)-N-cyclopropylbenzamide (0.774 g).

$^1$H-NMR (CD$_3$OD): 8.26 (s, 1H), 7.67 (d, 2H), 6.80 (d, 2H), 4.88 (s, 1H), 2.79 (m, 1H), 0.75 (m, 2H), 0.60 (m, 2H).

c) N-cyclopropyl-4-[(6-nitro-3-pyridinyl)oxy]benzamide

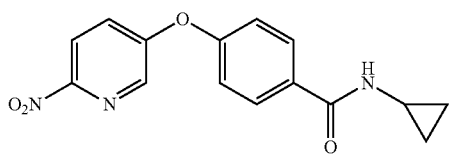

The mixture nitropyridine and bromopyridine was synthesized analogously to Example 11c from N-cyclopropyl-4-hydroxybenzamide (0.330 g).

$^1$H-NMR (CD$_3$OD): 8.33 (d, 1H), 8.32 (d, 1H), 7.92 (d, 2H), 7.66 (dd, 1H), 7.24 (d, 2H), 2.85 (m, 1H), 0.81 (m, 2H), 0.64 (m, 2H).

d) 4-[(6-amino-3-pyridinyl)oxy]-N-cyclopropylbenzamide

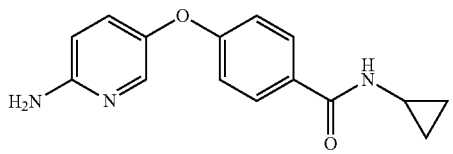

4-[(6-amino-3-pyridinyl)oxy]-N-cyclopropylbenzamide (0.128 g, 25%) was synthesized analogously to Example 11d from the mixture nitropyridine and bromopyridine.

$^1$H-NMR (CDCl$_3$): 7.92 (s, 1H), 7.68 (d, 2H), 7.20 (d, 1H), 6.92 (d, 2H), 6.54 (d, 1H), 6.12 (s, 1H), 4.41 (s, 2H), 2.89 (m, 1H), 0.81 (m, 2H), 0.64 (m, 2H).

e) 4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)-N-cyclopropylbenzamide

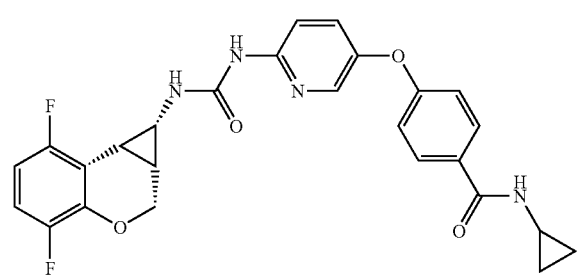

4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)-N-cyclopropylbenzamide (0.090 g, 38%) was synthesized analogously to Example 11e from 4-[(6-amino-3-pyridinyl)oxy]-N-cyclopropylbenzamide (0.128).

$^1$H-NMR (CDCl$_3$): 9.36 (s, 1H), 8.56 (s, 1H), 7.73 (d, 2H), 7.62 (d, 1H), 7.27 (dd, 1H), 6.91 (m, 3H), 6.78 (m, 1H), 6.57 (m, 1H), 6.23 (s, 1H), 4.45 (dd, 1H), 4.33 (dd, 1H), 3.72 (m, 1H), 2.90 (m, 1H), 2.60 (t, 1H), 1.97 (m, 1H), 0.87 (m, 2H), 0.63 (m, 2H).

Example 13

N-[4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)phenyl]acetamide a) N-{4-[(6-nitro-3-pyridinyl)oxy]phenyl}acetamide

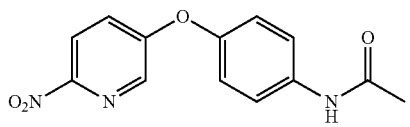

The title compound was synthesized analogously to Example 11c from N-(4-hydroxyphenyl)acetamide.

$^1$H-NMR (DMSO-d$_6$): 10.05 (s, 1H), 8.36 (d, 1H), 8.29 (d, 1H), 7.67 (d, 2H), 7.54 (dd, 1H), 7.18 (d, 2H), 2.03 (s, 3H).

b) N-{4-[(6-amino-3-pyridinyl)oxy]phenyl}acetamide

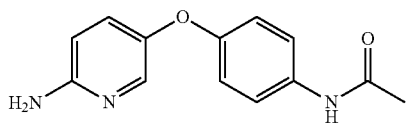

The title compound was synthesized analogously to Example 11d from N-{4-[(6-nitro-3-pyridinyl)oxy]phenyl}acetamide.

$^1$H-NMR (CDCl$_3$): 7.87 (d, 1H), 7.41 (d, 2H), 7.29 (s, 1H), 7.17 (dd, 1H), 6.89 (d, 2H), 6.51 (d, 1H), 4.47 (s, 2H), 2.14 (s, 3H).

d) N-[4-({6-[({[(1S,1aS,7bS)-4,7-difluoro-1,1a,2,7b-tetrahydrocyclopropa[c]chromen-1-yl]amino}carbonyl)amino]-3-pyridinyl}oxy)phenyl]acetamide

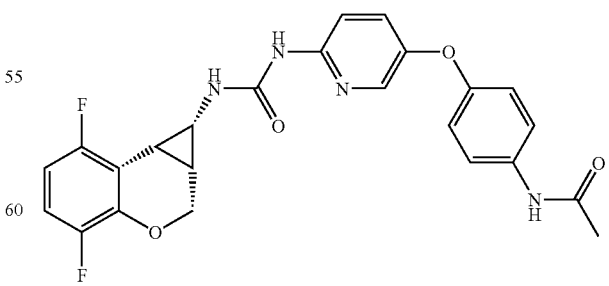

The title compound was synthesized analogously to Example 11e from N-{4-[(6-amino-3-pyridinyl)oxy]phenyl}acetamide.

$^1$H-NMR (CDCl$_3$): 9.39 (s, 1H), 8.82 (s, 1H), 7.54 (m, 3H), 7.47 (d, 2H), 7.20 (dd, 1H), 6.88 (d, 2H), 6.79 (m, 2H), 6.55 (m, 1H), 4.42 (dd, 1H), 4.32 (dd, 1H), 3.76 (m, 1H), 2.57 (t, 1H), 2.04 (m, 1H).

Example 14

N-[(1S,1aR,7bR)-4,7-difluoro-1,1a,2,7b-tetrahydro-cyclopropa[c]chromen-1-yl]-N'-{5-[4-(1H-1,2,4-triazol-1-yl)phenoxy]pyridin-2-yl}urea a) 2-nitro-5-[4-(1H-1,2,4-triazol-1-yl)phenoxy]pyridine Cesium carbonate (1.3 g, 4.03 mmol) was mixed with 3 ml of dry dimethylformamide, 4-(1H-1,2,4-triazol-1-yl)phenol (0.5 g, 3.1 mmol) and 5-bromo-2-nitropyridine (0.63 g, 3.1 mmol) and the reaction mixture was heated at stirring at 70° C. in a closed vial. The reaction mixture was then mixed with 40 ml of water and extracted into methylene chloride (3×20 ml). Organic extract was washed with water and brine, dried over magnesium sulfate and concentrated by rotary evaporation. The resulting greenish-brown solid was washed thoroughfully with methylene chloride to give 280 mg of desired compound (32% yield).

$^1$H-NMR (DMSO-d$_6$): 9.3 (s, 1H), 8.47 (d, 1H), 8.35 (d, 1H), 8.24 (s, 1H), 7.98 (d, 2H), 7.71 (dd, 1H), 7.45 (d, 2H).

b) 5-[4-(1H-1,2,4-triazol-1-yl)phenoxy]pyridin-2-amine

2-Nitro-5-[4-(1H-1,2,4-triazol-1-yl)phenoxy]pyridine (100 mg, 0.35 mmol) was mixed with 15-20 ml of ethanol and bubbled with argon. About 20 mg of Pd/C was added to the reaction mixture and hydrogen gas was applied at normal pressure and ambient temperature for 3-12 h. The reaction was monitored by TLC. After the reaction was complete, the reaction mixture was bubbled with argon, filtered through Celite and the solution obtained was concentrated by rotary evaporation to give 42 mg of desired aminopyridine after purification by column chromatography on silica (EtOAc/EtOH 100:1). Yield 47%.

$^1$H-NMR (CDCl$_3$): 8.4 (s, 1H), 8.01 (s, 1H), 7.85 (d, ~1H), 7.50 (d, 2H), 7.35 (s, 1H), 6.96 (d, 2H), 6.48 (d, 1H), 4.55 (br s, 2H).

c) N-[(1S,1aR,7bR)-4,7-difluoro-1,1a,2,7b-tetrahydrocyclopropa[c]chromen-1-yl]-N'-{5-[4-(1H-1,2,4-triazol-1-yl)phenoxy]pyridin-2-yl}urea

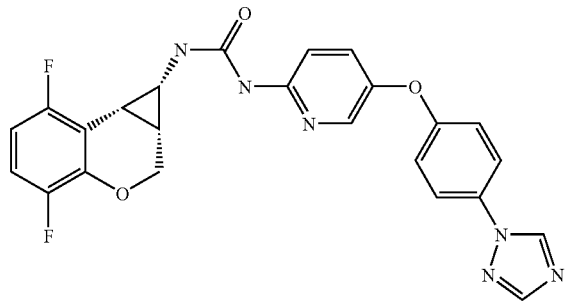

(1S,1aR,7bS)-4,7-difluoro-1,1a,2,7b-tetrahydrocyclopropa[c]chromene-1-carboxylic acid (33 mg, 0.15 mmol, ~95% ee) was mixed with toluene (1.5 ml), triethylamine (1.1 eq), 5-(3-fluorophenyl)-2-aminopyridine (1.1 eq), DPPA (1.1 eq) and bubbled with argon for about 5 min. The reaction mixture was then heated at stirring at 110° C. for 3 h under in a closed vial. The reaction mixture was concentrated by rotary evaporation and purified by column chromatography on silica (30 g of YMC silica, ethylacetate/hexane 1:1). Desired product was obtained as beige-white powder (40 mg, yield 57.5%).

$^1$H-NMR (CDCl$_3$): 9.42 (br s, 1H), 9.35 (br s, 1H), 8.52 (s, 1H), 8.10 (s, 1H), 7.65 (m, 3H), 7.30 (dd, 1H), 7.03 (d, 2H), 6.87 (d, 1H), 6.80 (m, 1H), 6.65 (d tr, 1H), 4.45 (dd, 1H), 4.33 (dd, 1H), 3.80 (q, 1H), 2.60 (br tr, 1H), 1.94-2.00 (m, 1H).

Additional Left Wings.

The following left wings are coupled to any of the above novel right hand wings analogously to Examples 1 to 14.

Example 15 a) ±cis-1,1a,2,7b-Tetrahydro-cyclopropa[c]chromene-1-carboxylic acid ethyl ester

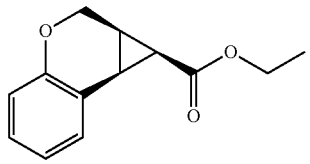

To a mixture of 2H-chromene (4.89 g, 37 mmol) and (CuOTf)$_2$-benzene (186 mg, 0.37 mmol) in 1,2-dichloroethane (80 mL) at 20° C., was added dropwise (3 h) a solution of ethyl diazoacetate (8.44 g, 74 mmol) in 1,2-dichloroethane (20 mL). After 15 min at 20° C., the reaction mixture was washed with H$_2$O (100 mL). The H$_2$O phase was washed with CH$_2$Cl$_2$ (50 mL) and the solvent of the combined organic phases was removed under reduced pressure. The crude product was column chromatographed (silica gel, 20→50% EtOAc in hexane), to give 1.96 g (24%) of ±cis-1,1a,2,7b-tetrahydro-cyclopropa[c]chromene-1-carboxylic acid ethyl ester and 3.87 g (48%) of ±-trans-1,1a,2,7b-tetrahydro-cyclopropa[c]chromene-1-carboxylic acid ethyl ester as a byproduct.

$^1$H-NMR (CDCl$_3$): 7.26 (d, 1H), 7.10 (dd, 1H), 6.90 (dd, 1H), 6.78 (d, 1H), 4.49 (dd, 1H), 4.20 (dd, 1H), 3.97 (q, 2H), 2.44 (dd, 1H), 2.14 (dd, 1H), 2.07-1.95 (m, 1H), 1.02 (t, 3H).

b) (±)-cis-1,1a,2,7b-Tetrahydro-cyclopropa[c]chromene-1-carboxylic acid

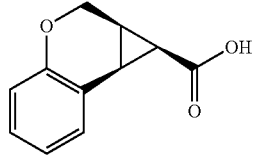

A mixture of (±)-cis-1,1a,2,7b-tetrahydro-cyclopropa[c]chromene-1-carboxylic acid ethyl ester (1.96 g, 9.0 mmol), LiOH (539 mg, 22.5 mmol), H$_2$O (10 mL) and MeOH (20 mL) was heated to reflux for 2 h. The reaction mixture was concentrated to about 10 mL, 4N HCl was added dropwise giving a white precipitate. The reaction mixture was extracted with CH$_2$Cl$_2$ (3×15 mL) and the solvent of the combined organic phases was removed under reduced pressure. The crude product was crystallized from EtOAc/hexane, to give 435 mg (25%) of (±)-cis-1,1a,2,7b-tetrahydro-cyclopropa[c]chromene-1-carboxylic acid as a white solid.

¹H-NMR (CDCl₃): 9.80 (br s, 1H), 7.22 (d, 1H), 7.10 (dd, 1H), 6.89 (dd, 1H), 6.77 (d, 1H), 4.45 (dd, 1H), 4.22 (dd, 1H), 2.45 (dd, 1H), 2.14-1.98 (m, 2H).

Example 16 a) (±)-cis-1,1a,3,7b-Tetrahydro-2-oxa-cyclopropa[a]naphthalene-1-carboxylic acid ethyl ester

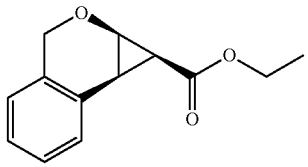

(±)-cis-1,1a,3,7b-Tetrahydro-2-oxa-cyclopropa[a]naphthalene-1-carboxylic acid ethyl ester was synthesized analogously to Example 15a from 1H-isochromene (3.57 g, 27 mmol), to give 910 mg (15%) of (±)-cis-1,1a,3,7b-tetrahydro-2-oxa-cyclopropa[a]naphthalene-1-carboxylic acid ethyl ester.

¹H-NMR (CDCl₃): 7.34 (d, 1H), 7.25 (dd, 1H), 7.18 (dd, 1H), 7.03 (d, 1H), 4.81 (d, 1H), 4.51 (d, 1H), 4.28 (dd, 1H), 3.95 (q, 2H), 2.43 (dd, 1H), 2.05 (dd, 1H), 1.04 (t, 3H).

b) (±)-cis-1,1a,3,7b-Tetrahydro-2-oxa-cyclopropa[a]naphthalene-1-carboxylic acid

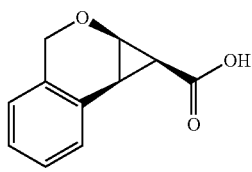

(±)-cis-1,1a,3,7b-Tetrahydro-2-oxa-cyclopropa[a]naphthalene-1-carboxylic acid was synthesized analogously to Example 15b from (±)-cis-1,1a,3,7b-tetrahydro-2-oxa-cyclopropa[a]naphthalene-1-carboxylic acid ethyl ester (436 mg, 2 mmol), to give 86 mg (22%) of (±)-cis-1,1a,3,7b-tetrahydro-2-oxa-cyclopropa[a]-naphthalene-1-carboxylic acid as a white solid. The crude product was column chromatographed (silica gel, 1→5% MeOH in CH₂Cl₂).

¹H-NMR (CDCl₃): 8.50 (br s, 1H), 7.39 (d, 1H), 7.30 (dd, 1H), 7.21 (dd, 1H), 7.07 (d, 1H), 4.87 (d, 1H), 4.57 (d, 1H), 4.38 (dd, 1H), 2.59 (dd, 1H), 2.15 (dd, 1H).
The product of step b

Example 17

(±)-cis-1-(5-Cyano-pyridin-2-yl)-3-(7-hydroxy-6-propionyl-1,1a,2,7b-tetrahydro-cyclopropa[c]chromen-1-yl)-urea a) 1-(2-Hydroxy-4-prop-2-ynyloxy-phenyl)-propan-1-one

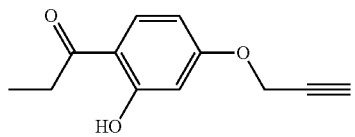

A mixture of 2',4'-dihydroxy-propiophenone (24.9 g, 0.15 mol), 3-bromo-propyne (24.2 g, 0.20 mol) and K₂CO₃ (20.7 g, 0.15 mol) in acetone (500 mL) was refluxed for 12 h. The reaction mixture was allowed assume room temperature and the precipitate was removed by filtration. The filtrate was concentrated under reduced pressure. The crude product was purified by column chromatography (silica gel, 0→2% MeOH in H₂O), to give 26.2 g (85%) of 1-(2-hydroxy-4-prop-2-ynyloxy-phenyl)-propan-1-one.

¹H-NMR (CDCl₃): 12.80 (s, 1H), 7.69 (d, 1H), 6.52 (m, 2H), 4.72 (d, 2H), 2.96 (q, 2H), 2.56 (t, 1H), 1.23 (t, 3H).

3b) 1-(5-Hydroxy-2H-chromen-6-yl)-propan-1-one

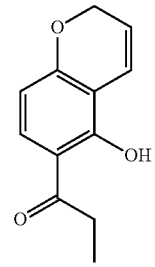

A mixture of 1-(2-hydroxy-4-prop-2-ynyloxy-phenyl)-propan-1-one (19.8 g, 97 mmol) and N,N-diethylaniline (100 mL) was heated to reflux for 3 h. The reaction mixture was concentrated under reduced pressure. The crude product was purified by column chromatography (silica gel, 5→10% EtOAc in Hexane) and thereafter recrystallized from EtOAc/Hexane, to give 8.91 g (45%) of 1-(5-hydroxy-2H-chromen-6-yl)-propan-1-one.

¹H-NMR (CDCl₃): 13.00 (s, 1H), 7.49 (d, 1H), 6.75 (dt, 1H), 6.27 (d, 1H), 5.67 (dt, 1H), 4.86 (dd, 2H), 2.90 (q, 2H), 1.19 (t, 3H).

3c) 7-Hydroxy-6-propionyl-1,1a,2,7b-tetrahydrocyclopropa[c]chromene-1-carboxylic acid ethyl ester

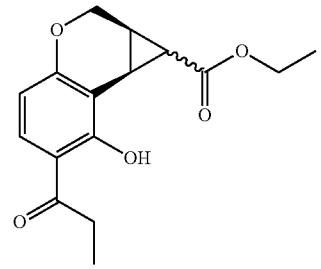

To a mixture of 1-(5-hydroxy-2H-chromen-6-yl)-propan-1-one (511 mg, 2.5 mmol) and (Rh(II)Ac₂)₂ (11 mg, 0.025 mmol) in 1,2-dichloroethane (8 mL) at 20° C., was added dropwise (3 h) a solution of ethyl diazoacetate (571 mg, 5 mmol) in 1,2-dichloroethane (2 mL). After 15 min at 20° C., the reaction mixture was washed with H₂O (10 mL). The H₂O phase was washed with CH₂Cl₂ (10 mL) and the solvent of the combined organic phases was removed under reduced pressure. The crude product was purified by column chromatography (silica gel, 1→5% MeOH in CH₂Cl₂), to give 300 mg (41%) of 7-hydroxy-6-propionyl-1,1a,2,7b-tetrahydro-cyclopropa[c]chromene-1-carboxylic acid ethyl ester (a 33/64 mixture of cis and trans isomers).

¹H-NMR (CDCl₃): 13.13-13.07 (m, 1H), 7.57-7.49 (m, 1H), 6.41-6.38 (m, 1H), 4.65-3.92 (m, 4H), 3.01-1.95 (m, 5H), 1.29-1.08 (m, 6H).

3d) (±)-cis-7-Hydroxy-6-propionyl-1,1a,2,7b-tetrahydro-cyclopropa[c]chromene-1-carboxylic acid

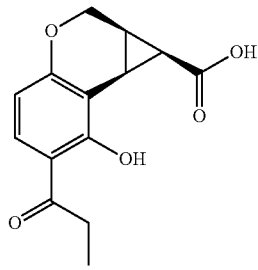

(±)cis-7-Hydroxy-6-propionyl-1,1a,2,7b-tetrahydro-cyclopropa[c]chromene-1-carboxylic acid was synthesized analogously to Example 16b from 7-hydroxy-6-propionyl-1,1a,2,7b-tetrahydro-cyclopropa[c]chromene-1-carboxylic acid ethyl ester (299 mg, 1.03 mmol, a 33/64 mixture of cis and trans isomers), to give 39.3 mg (15%) of (±)-cis-7-hydroxy-6-propionyl-1,1a,2,7b-tetrahydro-cyclopropa[c]chromene-1-carboxylic acid as a white solid and (±)-trans-7-hydroxy-6-propionyl-1,1a,2,7b-tetrahydro-cyclopropa[c]chromene-1-carboxylic acid as a byproduct. The crude product was purified by column chromatography (silica gel, 1→5% MeOH in CH₂Cl₂).
¹H-NMR (DMSO-d₆): 7.67 (d, 1H), 6.35 (d, 1H), 4.57 (dd, 1H), 4.36 (dd, 1H), 2.98 (q, 2H), 2.55-2.46 (m, 1H), 2.18-2.00 (m, 2H), 1.10 (t, 3H).

Example 18 a) 1-(2-Hydroxy-4-prop-2-ynyloxy-phenyl)-ethanone

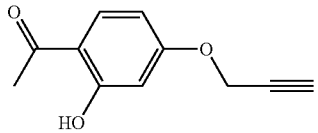

1-(2-Hydroxy-4-prop-2-ynyloxy-phenyl)-ethanone was synthesized analogously to Example 17a from 1-(2,4-dihydroxy-phenyl)-ethanone (20 g, 131 mmol), to give 22 g (88%) of 1-(2-hydroxy-4-prop-2-ynyloxy-phenyl)-ethanone.
¹H-NMR (CDCl₃): 12.70 (s, 1H), 7.66 (d, 1H), 6.52 (m, 2H), 4.72 (d, 2H), 2.58-2.55 (m, 4H).

b) 1-(5-Hydroxy-2H-chromen-6-yl)-ethanone

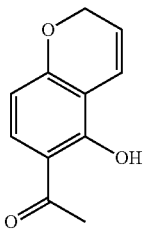

1-(5-Hydroxy-2H-chromen-6-yl)-ethanone was synthesized analogously to Example 46b from 1-(2-hydroxy-4-prop-2-ynyloxy-phenyl)-ethanone (17 g, 89 mmol), to give 6.0 g (35%) of 1-(5-hydroxy-2H-chromen-6-yl)-ethanone.

¹H-NMR (CDCl₃): 12.92 (s, 1H), 7.51 (d, 1H), 6.79 (dt, 1H), 6.32 (d, 1H), 5.71 (dt, 1H), 4.89 (dd, 2H), 2.55 (s, 3H).

c) 6-Acetyl-7-hydroxy-1,1a,2,7b-tetrahydro-cyclopropa[c]chromene-1-carboxylic acid ethyl ester

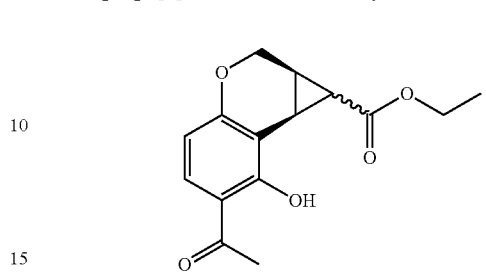

6-Acetyl-7-hydroxy-1,1a,2,7b-tetrahydro-cyclopropa[c]chromene-1-carboxylic acid ethyl ester (a 40/60 mixture of cis and trans isomers) was synthesized analogously to Example 17c from 1-(5-hydroxy-2H-chromen-6-yl)-ethanone.
¹H-NMR (CDCl₃): 13.05-12.97 (m, 1H), 7.54-7.47 (m, 1H), 6.43-6.33 (m, 1H), 4.63-3.94 (m, 4H), 3.02-1.96 (m, 6H), 1.31-1.08 (m, 3H).

d) 6-Acetyl-7-hydroxy-1,1a,2,7b-tetrahydro-cyclopropa[c]chromene-1-carboxylic acid

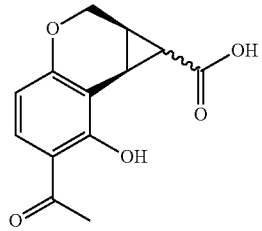

6-Acetyl-7-hydroxy-1,1a,2,7b-tetrahydro-cyclopropa[c]chromene-1-carboxylic acid was synthesized analogously to Example 15b from 6-acetyl-7-hydroxy-1,1a,2,7b-tetrahydro-cyclopropa[c]chromene-1-carboxylic acid ethyl ester (2 g, 8.1 mmol, a 40/60 mixture of cis and trans isomers), to give 300 mg (17%) of 6-acetyl-7-hydroxy-1,1a,2,7b-tetrahydro-cyclopropa[c]chromene-1-carboxylic acid (a 40/60 mixture of cis and trans isomers). The crude product was purified by column chromatography (silica gel, 1→5% MeOH in CH₂Cl₂)
¹H-NMR (CDCl₃): 7.55-7.45 (m, 1H), 6.45-6.30 (m, 1H), 4.65-4.00 (m, 2H), 3.05-1.95 (m, 6H).

Example 19

5a) 1-(4-Fluoro-2-prop-2-ynyloxy-phenyl)-propan-1-one

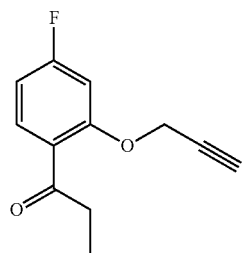

To a mixture of NaH (95%, 278 mg, 11 mmol) in DMF (20 mL) at 0° C., was added 1-(4-fluoro-2-hydroxy-phenyl)-propan-1-one (1.68 g, 10 mmol) in DMF (5 mL). After 15 min at 0° C., was 3-bromo-propyne (3.02 g, 20 mmol) added to the reaction mixture. After 1 h at 0° C., was the reaction mixture allowed to assume room temperature. The reaction mixture was extracted with H₂O (100 mL). The H₂O phase was washed with Et₂O (3×100 mL) and the solvent of the combined organic phases was removed under reduced pressure. The crude product was purified by column chromatography (silica gel, CH₂Cl₂), to give 1.40 g (68%) of 1-(4-fluoro-2-prop-2-ynyloxy-phenyl)-propan-1-one.

¹H-NMR (CDCl₃): 7.64 (dd, 1H), 6.69 (dd, 1H), 6.60 (ddd, 1H), 4.68 (d, 2H), 2.85 (q, 2H), 2.58 (t, 1H), 1.03 (t, 3H).

b) 1-(5-Fluoro-2H-chromen-8-yl)-propan-1-one

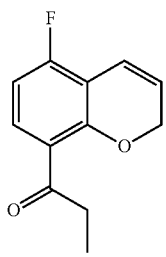

1-(5-Fluoro-2H-chromen-8-yl)-propan-1-one was synthesized analogously to Example 17b from 1-(4-fluoro-2-prop-2-ynyloxy-phenyl)-propan-1-one (1.34 g, 6.5 mmol), to give 619 mg (46%) of 1-(5-fluoro-2H-chromen-8-yl)-propan-1-one.

¹H-NMR (CDCl₃): 7.60 (dd, 1H), 6.67-6.58 (m, 2H), 5.86 (dt, 1H), 4.76 (dd, 2H), 2.93 (q, 2H), 1.23 (t, 3H).

c) (±)-cis-7-Fluoro-4-propionyl-1,1a,2,7b-tetrahydro-cyclopropa[c]chromene-1-carboxylic acid ethyl ester

(±)-cis-7-Fluoro-4-propionyl-1,1a,2,7b-tetrahydro-cyclopropa[c]chromene-1-carboxylic acid ethyl ester was synthesized according to method 17c from 1-(5-fluoro-2H-chromen-8-yl)-propan-1-one (619 mg, 3 mmol), to give 142 mg (16%) of (±)-cis-7-fluoro-4-propionyl-1,1a,2,7b-tetrahydro-cyclopropa[c]chromene-1-carboxylic acid ethyl ester and (±)-trans-7-fluoro-4-propionyl-1,1a,2,7b-tetrahydro-cyclopropa[c]chromene-1-carboxylic acid ethyl ester as a byproduct.

¹H-NMR (CDCl₃): 7.59 (dd, 1H), 6.65 (m, 1H), 4.50-4.46 (m, 2H), 3.95 (q, 2H); 2.89 (q, 2H), 2.57 (dd, 1H), 2.20 (dd, 1H), 1.13-1.03 (m, 1H), 1.12-1.01 (m, 6H).

d) (±)-cis-7-Fluoro-4-propionyl-1,1a,2,7b-tetrahydro-cyclopropa[c]chromene-1-carboxylic acid

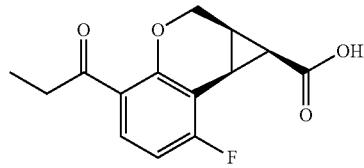

(±)-cis-7-Fluoro-4-propionyl-1,1a,2,7b-tetrahydro-cyclopropa[c]chromene-1-carboxylic acid was synthesized analogously to Example 15b from (±)-cis-7-fluoro-4-propionyl-1,1a,2,7b-tetrahydro-cyclopropa[c]chromene-1-carboxylic acid ethyl ester (140.3 mg, 0.48 mmol), to give 83 mg (65%) of (±)-cis-7-fluoro-4-propionyl-1,1a,2,7b-tetrahydro-cyclopropa[c]chromene-1-carboxylic acid as a white solid. The crude product was purified by column chromatography (silica gel, 1→5% MeOH in CH₂Cl₂).

¹H-NMR (DMSO-d₆): 12.15 (br s, 1H), 7.46 (dd, 1H), 6.78 (dd, 1H), 4.57 (dd, 1H), 4.43 (dd, 1H), 2.93-2.80 (m, 2H), 2.55 (dd, 1H), 2.24 (dd, 1H), 2.20-2.10 (m, 1H), 1.02 (t, 3H).

Example 20 a) 6-Fluoro-2-hydroxy-3-methoxy-benzaldehyde 1M boron trichloride in dichloromethane (25 ml; 25 mmol) was added to a solution of 6-fluoro-2,3-dimethoxy-benzaldehyde [Cantrell, Amanda S.; Engelhardt, Per; Hoegberg, Marita; Jaskunas, S. Richard; Johansson, Nils Gunnar; et al.; J. Med. Chem.; 39; 21; 1996; 4261-4274] (4.26 g; 23 mmol) in dichloromethane (30 ml) keeping the reaction temperature at −70° C. The reaction mixture stirred at room temperature overnight and hydrolyzed with water. The organic phase was separated, washed with water and evaporated in vacuo. The residue was chromatographed (silica gel, EA:Hex, 5:1) to give 3.72 g (94%) of 6-fluoro-2-hydroxy-3-methoxy-benzaldehyde as yellow crystals.

¹H-NMR (CDCl₃): 11.61 (s, 1H), 10.23 (s, 1H), 7.02 (dd, 1H), 6.55 (app. t, 1H), 3.87 (s, 3H).

b) 5-Fluoro-8-methoxy-2H-chromene

6-Fluoro-2-hydroxy-3-methoxy-benzaldehyde (3.32 g, 19 mmol) was dissolved in acetonitrile (20 ml) and DBU (2.97 ml, 19 mmol) was added followed by vinyltriphenylphosphine bromide (7.2 g, 19 mmol). The reaction mixture was heated under reflux for 48 h, diluted with water and extracted with ether (3×50 ml). The organic phase was washed with water, 10% sodium hydroxide, water and brine and evaporated in vacuo. The residue was submitted to column chromatography (silica gel, EA:Hex, 1:20) yielding 1.2 g of 5-fluoro-8-methoxy-2H-chromene (34%).

¹H-NMR (CDCl₃): 6.65 (m, 2H), 6.54 (t, 1H), 5.83 (dt, 1H), 4.88 (dd, 2H), 3.83 (s, 3H).

c) (±)-cis-7-Fluoro-4-methoxy-1,1a,2,7b-tetrahydro-cyclopropa[c]chromene-1-carboxylic acid ethyl ester The title compound was synthesized analogously to example 17c from 5-fluoro-8-methoxy-2H-chromene.

¹H-NMR (CDCl₃): 6.7-6.5 (m, 2H), 4.48 (m, 2H), 3.99 (m, 2H), 3.80 (s, 3H), 2.57 (app. t, 1H), 2.20 (app. t, 1H), 2.05 (m, 1H), 1.08 (t, 3H).

d) (±)-cis-7-Fluoro-4-methoxy-1,1a,2,7b-tetrahydro-cyclopropa[c]chromene-1-carboxylic acid The title compound was synthesized analogously to example 15b from (±)-cis-7-fluoro-4-methoxy-1,1a,2,7b-tetrahydro-cyclopropa[c]chromene-1-carboxylic acid ethyl ester.

¹H-NMR (CDCl₃): 6.7-6.5 (m, 2H), 4.48 (m, 2H), 3.80 (s, 3H), 2.61 (app. t, 1H), 2.17 (app. t, 1H), 2.06 (m, 1H).

e) (±)-cis-1-(5-Cyano-pyridin-2-yl)-3-(7-fluoro-4-methoxy-1,1a,2,7b-tetrahydro-cyclopropa[c]chromen-1-yl)-urea The title compound was synthesized analogously to Example 15c from (±)-cis-7-fluoro-4-methoxy-1,1a,2,7b-tetrahydro-cyclopropa[c]chromene-1-carboxylic acid (62 mg, 0.17 mmol). Yield 38 mg (40%).

$^1$H-NMR (CDCl$_3$): 10.06 (br. s, 1H), 9.40 (br. d, 1H), 8.11 (d, 1H), 7.70 (dd, 1H), 6.91 (d, 1H), 6.68 (m, 2H), 4.48 (dd, 1H), 4.28 (dd, 1H), 3.90-3.72 (m, 4H), 2.64 (app. T, 1H), 1.96 (m, 1H).

Example 21 a) 1-Chloro-4-fluoro-2-prop-2-ynyloxy-benzene

The title compound was synthesized analogously to example 15a) from 2-chloro-5-fluorophenol (2.5 g). Yield 2.8 g (90%).

$^1$H-NMR (CDCl$_3$): 7.32 (dd, 1H), 6.85 (dd, 1H), 6.68 (m, 1H), 4.77 (d, 2H), 2.58 (t, 1H).

b) 5-Fluoro-8-chloro-2H-chromene

The title compound was synthesized analogously to Example 15b) from 1-chloro-4-fluoro-2-prop-2-ynyloxy-benzene (2.8 g). Yield 0.97 g (35%).

$^1$H-NMR (CDCl$_3$): 7.09 (dd, 1H), 6.63 (dt, 1H), 6.56 (t, 1H), 5.84 (dt, 1H), 4.95 (dd, 2H).

c) (±) cis-7-Fluoro-4-chloro-1,1a,2,7b-tetrahydro-cyclopropa[c]chromene-1-carboxylic acid ethyl ester The title compound was synthesized analogously to Example 15c) from 5-Fluoro-8-chloro-2H-chromene.

$^1$H-NMR (CDCl$_3$): 7.14 (dd, 1H), 6.60 (t, 1H), 4.51 (m, 2H), 4.01 (m, 2H), 2.60 (app. t, 1H), 2.23 (t, 1H), 2.09 (m, 1H), 1.08 (t, 3H).

d) (±)-cis-7-Fluoro-4-chloro-1,1a,2,7b-tetrahydro-cyclopropa[c]chromene-1-carboxylic acid The title compound was synthesized analogously to example 15d) from (±)-cis-7-fluoro-4-chloro-1,1a,2,7b-tetrahydro-cyclopropa[c]chromene-1-carboxylic acid ethyl ester 850 mg). Yield 43 mg (96%).

$^1$H-NMR (CDCl$_3$): 8.86 (br. s, 1H), 7.13 (dd, 1H), 6.59 (t, 1H), 4.50 (m, 2H), 2.63 (t, 1H), 2.23-2.05 (m, 2H).

Example 22 a) Trifluoro-methanesulfonic acid 4-formyl-3-hydroxy-phenyl ester

A solution of triflic anhydride (1.77 ml, 10.5 mmol) in dichloromethane 10 ml) was added to a mixture of ~2,4-dihydroxybenzaldehyde (1.38 g, 10 mmol) and pyridine (0.85 ml, 10.5 mmol) in dichloromethane (30 ml) at −70 C. Dry ice bath was removed and the reaction mixture was stirred for 2 h at room temperature. The reaction mixture was diluted with dichloromethane, washed with water, brine and evaporated in vacuo. The crude product was purified by column chromatography (silica gel, EA:Hex, 1:6) to give 1.55 g of trifluoro-methanesulfonic acid 4-formyl-3-hydroxy-phenyl ester (57%).

$^1$H-NMR (CDCl$_3$): 11.28 (s, 1H), 9.93 (s, 1H), 7.67 (d, 1H), 6.95 (m, 2H).

b) Trifluoro-methanesulfonic acid 3-allyloxy-4-formyl-phenyl ester

Potassium carbonate (1.6 g, 11.5 mmol) and allyl bromide (1 ml, 11.5 mmol) were added to a solution of trifluoro-methanesulfonic acid 4-formyl-3-hydroxy-phenyl ester (1.55 g, 5.7 mmol) in acetone (50 ml). The reaction mixture was stirred at 55 C for 2 h, filtered and evaporated in vacuo. The residue was chromatographed (silica gel, EA:Hex, 1:20) to give 1.3 g (73%) of trifluoro-methanesulfonic acid 3-allyloxy-4-formyl-phenyl ester.

$^1$H-NMR (CDCl$_3$): 10.47 (s, 1H), 7.93 (d, 1H), 6.95 (d, 1H), 6.90 (s, 1H), 6.05 (m, 1H), 5.47 (d, 1H), 5.40 (d, 1H), 4.69 (d, 2H).

c) Trifluoro-methanesulfonic acid 3-allyloxy-4-vinyl-phenyl ester

Methyltriphenylphosphonium bromide (1.95 g, 5.45 mmol) was added to a suspension of sodium hydride (60% in oil) (0.25 g, 6.3 mmol) in THF (35 ml) at 0 C. and it was stirred for 30 min at room temperature. To the above solution was added solution of trifluoro-methanesulfonic acid 3-allyloxy-4-formyl-phenyl ester (1.3 g, 4.2 mmol) in THF (15 ml), and the reaction mixture was stirred for 2 h at room temperature. The reaction mixture was diluted with hexane and extracted with water. Organic phase was washed with brine and evaporated. Silica gel column chromatography (EA:Hex, 1:20) afforded trifluoro-methanesulfonic acid 3-allyloxy-4-vinyl-phenyl ester (0.68 g, 53%).

$^1$H-NMR (CDCl$_3$): 7.51 (d, 1H), 7.02 (dd, 1H), 6.85 (dd, 1H), 6.77 (d, 1H), 6.05 (m, 1H), 5.76 (dd, 1H), 5.43 (m, 1H), 5.32 (m, 2H), 4.58 (dt, 2H).

d) Trifluoro-methanesulfonic acid 2H-chromen-7-yl ester

To a solution of trifluoro-methanesulfonic acid 3-allyloxy-4-vinyl-phenyl ester (0.68 g, 2.2 mmol) in dichloromethane (5 ml) was added Ru-catalyst (Grubb's catalyst) (36 mg, 2 mol %), and the reaction mixture was stirred for 2 h at room temperature. After that period the reaction was complete (GC) and the reaction mixture was used in the next step without any work-up. Analytical sample was obtained after removal of the solvent by silica gel column chromatography (EA:Hex, 1:20).

$^1$H-NMR (CDCl$_3$): 6.97 (d, 1H), 6.76 (dd 1H), 6.68 (d, 1H), 6.39 (dt, 1H), 5.81 (dt, 1H), 4.98 (dd, 2H).

e) (±) cis-5-Trifluoromethanesulfonyloxy-1,1a,2,7b-tetrahydro-cyclopropa[c]chromene-1-carboxylic acid ethyl ester Rh(OAc)$_2$ (19 mg, 2 mol %) was added to the above solution (10d) and the solution of EDA (0.44 ml, 4.4 mmol) in 1 ml of dichloromethane was added with a syringe pump over 5 h at room temperature. When the reaction was complete (GC) dichloromethane was evaporated, the residue was dissolved in ethyl acetate and washed with saturated ammonium chloride solution and brine. Organic phase was evaporated and crude mixture of cis- and trans-isomers (1:1.3) was separated by column chromatography (silica gel, EA:Hex, 1:6) to give 0.4 g (50%) of ±cis-5-trifluoromethanesulfonyloxy-1,1a,2,7b-tetrahydro-cyclopropa[c]chromene-1-carboxylic acid ethyl ester.

¹H-NMR (CDCl₃): 7.29 (d, 1H), 6.82 (dd, 1H), 6.73 (d, 1H), 4.51 (dd, 1H), 4.29 (dd, 1H), 3.98 (m, 2H), 2.45 (t, 1H), 2.19 (t, 1H), 2.05 (m, 1H), 1.03 (t, 3H).

f) ±cis-5-Cyano-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (154 mg, 0.42 mmol), Pd(OAc)₂ (9 mg, 10 mol %) and PPh₃ (44 mg, 40 mol %) were mixed in DMF (4 ml) and gentle stream of nitrogen passed through reaction mixture for 10 min. Zn(CN)₂ (74 mg, 0.63 mmol) was added, vial was sealed and the reaction mixture was stirred at 120 C. overnight. The reaction mixture was diluted with ethyl acetate and extracted with saturated ammonium chloride. Organic phase was evaporated and residue chromatographed (silica gel, EA:Hex 1:5) to give 53 mg (52%) of ±cis-5-cyano-1,1a,2,7b-tetrahydro-cyclopropa[c]chromene-1-carboxylic acid ethyl ester.

¹H-NMR (CDCl₃): 7.33 (d, 1H), 7.19 (dd, 1H), 7.05 (d, 1H), 4.50 (dd, 1H), 4.25 (dd, 1H), 3.99 (q, 2H), 2.46 (t, 1H), 2.25 (t, 1H), 2.11 (m, 1H), 1.06 (t, 3H).

g) ±cis-5-Cyano-1,1a,2,7b-tetrahydro-cyclopropa[c]chromene-1-carboxylic acid

±cis-5-Cyano-1,1a,2,7b-tetrahydro-cyclopropa[c]chromene-1-carboxylic acid ethyl ester (53 mg, 0.22 mmol) and NaOH (35 mg, 0.88 mmol) were dissolved in mixture methanol water (1:1) (5 ml). Reaction mixture was stirred at 60 C for 30 min. Methanol was evaporated in vacuo and 20 ml of water was added. Resulting solution was extracted with ether. Water phase was concentrated, acidified with 1M HCl to pH~2 and extracted with ether. The organic phase was washed with brine and evaporated to give 42 mg (90%) of ±cis-5-cyano-1,1a,2,7b-tetrahydro-cyclopropa[c]chromene-1-carboxylic acid.

¹H-NMR (CDCl₃): 7.33 (d, 1H), 7.19 (dd, 1H), 7.06 (d, 1H), 4.51 (dd, 1H), 4.31 (dd, 1H), 2.53 (app. t, 1H), 2.27 (app. t, 1H), 2.16 (m, 1H).

Example 23 a) ±cis-5-Trimethylsilanylethynyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (152 mg, 0.41 mmol), DPPP (38 mg, 20 mol %), Pd(dba)₂ (24 mg, 10 mol %), CuI (3 mg, 4 mol %) were mixed in 3 ml of triethylamine and gentle stream of nitrogen passed through reaction mixture for 10 min. Trimethylsilyl-acetylene (0.088 ml, 0.62 mmol) was added, vial was sealed and the reaction mixture was stirred at 120 C overnight. The reaction mixture was diluted with ethyl acetate, washed with water, brine and evaporated. The residue was purified by silica gel column chromatography (EA:Hex, 1:15) to give 0.1 g (77%) of ±cis-5-trimethylsilanylethynyl-1,1a,2,7b-tetrahydro-cyclopropa[c]chromene-1-carboxylic acid ethyl ester.

¹H-NMR (CDCl₃): 7.15 (d, 1H), 7.01 (dd, 1H), 6.88 (d, 1H), 4.47 (dd, 1H), 4.16 (dd, 1H), 3.96 (q, 2H), 2.38 (t, 1H), 2.13 (t, 1H), 2.01 (m, 1H), 1.04 (t, 3H), 0.22 (s, 9H).

b) ±cis-5-Ethynyl-1,1a,2,7b-tetrahydro-cyclopropa[c]chromene-1-carboxylic acid

±cis-5-Trimethylsilanylethynyl-1,1a,2,7b-tetrahydro-cyclopropa[c]chromene-1-carboxylic acid ethyl ester (0.1 g, 0.32 mmol) and sodium hydroxide (0.076 g, 1.9 mmol) were dissolved in mixture of methanol:water (1:1) (5 ml). The reaction mixture was heated at 60 C for 5 h, then it was acidified with 1M HCl to pH~2 and extracted with ether. The organic phase was washed with brine and evaporated to give 66 mg (97%) of) ±cis-5-ethynyl-1,1a,2,7b-tetrahydro-cyclopropa[c]chromene-1-carboxylic acid.

¹H-NMR (CDCl₃): 7.17 (d, 1H), 7.03 (dd, 1H), 6.91 (d, 1H), 4.45 (dd, 1H), 4.23 (dd, 1H), 3.02 (s, 1H), 2.46 (t, 1H), 2.13 (t, 1H), 2.07 (m, 1H).

Example 24

±cis-1-(5-Acetyl-1,1a,2,7b-tetrahydro-cyclopropa[c]chromen-1-yl)-3-(5-cyano-pyridin-2-yl)-urea a) ±cis-5-Acetyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (117 mg, 0.32 mmol), DPPP (7.3 mg, 50 mol %), Pd(OAc)₂ (2 mg, 25 mol %) and triethyl amine (0.09 ml, 0.64 mmol) were mixed in DMF (3 ml) and gentle stream of nitrogen passed through reaction mixture for 10 min. Butyl vinyl ether (0.21 ml, 1.6 mmol) was added, vial was sealed and the reaction mixture was stirred at 100 C for 2 h. 5% HCl (5 ml) was added and the reaction mixture was stirred at room temperature for 30 min. Resulting mixture was extracted with ethyl acetate. The organic phase was washed with saturated ammonium chloride and evaporated. The residue was purified by silica gel column chromatography (EA:Hex, 1:5) to give 76 mg (91%) of ±cis-5-acetyl-1,1a,2,7b-tetrahydro-cyclopropa[c]chromene 1-carboxylic acid ethyl ester.

¹H-NMR (CDCl₃): 7.52 (dd, 1H), 7.36 (d, 1H), 7.34 (d, 1H), 4.51 (dd, 1H), 4.21 (dd, 1H), 3.98 (q, 2H), 2.53 (s, 3H), 2.47 (t, 1H), 2.23 (t, 1H), 2.08 (m, 1H), 1.05 (t, 3H).

b) ±cis-5-Acetyl-1,1a,2,7b-tetrahydro-cyclopropa[c]chromene-1-carboxylic acid

The title compound was synthesized analogously to example 22 g from ±cis-5-acetyl-1,1a,2,7b-tetrahydro-cyclopropa[c]chromene-1-carboxylic acid ethyl ester (76 mg, 29 mmol).Yield 66 mg (97%).

¹H-NMR (CDCl₃): 7.52 (dd, 1H), 7.37 (d, 1H), 7.34 (d, 1H), 4.52 (dd, 1H), 4.26 (dd, 1H), 2.55 (s, 3H), 2.53 (t, 1H), 2.25 (t, 1H), 2.13 (m, 1H).

Example 25

±cis-5-Methoxy-1,1a,2,7b-tetrahydro-cyclopropa[c]chromene-1-carboxylic acid

The title compound was synthesized analogously to example 22 from 2-hydroxy-4-methoxybenzaldehyde.

Example 26 a) N-Acetyl-1,2-dihydroquinoline

Quinoline (19.37 g, 150 mmol) was dissolved in anhydrous diethyl ether (500 ml) and cooled to 0° C. under inert atmosphere. DIBAL, 1.5 M in toluene (100 ml, 150 mmol) was added dropwise over 2 hrs and the reaction mixture was stirred at 0° C. for 30 min. Acetic anhydride (500 ml) was added dropwise over 30 min and the reaction mixture was stirred at 0° C. for 30 min. H$_2$O was added cautiously. The reaction mixture was extracted with diethyl ether and concentrated to give N-acetyl-1,2-dihydroquinoline (11.5 g, 44%).

b) ±cis-(N-acetyl-1,1a,2,7b-tetrahydro-cyclopropa[c] quinoline)-1-carboxylic acid ethyl ester ±cis-(N-acetyl-1,1a,2,7b-tetrahydro-cyclopropa[c]quinoline)-1-carboxylic acid ethyl ester was prepared according to the procedure described in example 15a, from N-acetyl-1,2-dihydroquinoline (10 g, 58 mmol) The product was purified by column chromatography on silica (EtOAc/hexane 5%→50%) to give ±cis-(N-acetyl-1,1a,2,7b-tetrahydro-cyclopropa[c]quinoline)-1-carboxylic acid ethyl ester (2.0 g, 13%).

c) ±cis-(N-Acetyl-1,1a,2,7b-tetrahydro-cyclopropa [c]quinoline)-1-carboxylic acid ±cis-(N-Acetyl-1,1a,2,7b-tetrahydro-cyclopropa[c]quinoline)-1-carboxylic acid (425 mg, 24%) was prepared according to the procedure described in example 15b, from cis-(N-acetyl-1,1a,2,7b-tetrahydro-cyclopropa[c]quinoline)-1-carboxylic acid ethyl ester (2.0 mg, 7.7 mmol).

Example 27 a) 2,4-Difluoro-2-propynyloxybenzene

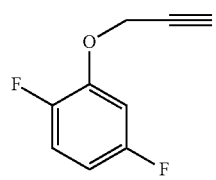

Commercially available 2,5-difluorophenol (20 g, 0.15 mol), K$_2$CO$_3$ (53 g, 0.38 mol) and commercially available 3-bromopropyne (45 g, 0.38 mol) were dissolved in acetone (300 ml), refluxed over night, cooled and filtrated. The solvent was removed and the crude product, dissolved in ether and washed with water and brine. The organic phase was evaporated and the crude product was re-dissolved in a small amount of ether and filtrated through a column of basic Al$_2$O$_3$. Evaporation and drying gave 20 g (80%) of 2,4-difluoro-2-prop-ynyloxy-benzene b) 5,8-Difluoro-2H-chromene

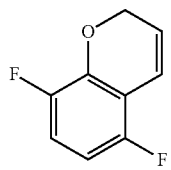

2,4-Difluoro-2-propynyloxybenzene (20 g, 0.12 mol) was dissolved in N,N-diethyl aniline (100 ml) and heated under argon atmosphere at 225 deg. Celcius with an oil-bath for 6-8 h. Ether (150 ml) was added and the aniline was removed by extraction using 2 M HCl$_{(aq)}$. Purification by chromatography (silica gel, n-hexane) gave 5,8-difluoro-2H-chromene 5.8 g (29%)

c) +/−cis-4,7-Difluoro-1,1a,2,7b-tetrahydro-cyclopropa[c]chromene-1-carboxylic acid ethyl ester

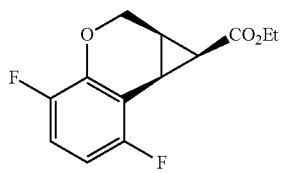

5,8-Difluoro-2H-chromene (5 g, 0.03 mol), (Rh(II)Ac$_2$)$_2$ (0.39 g, 0.00089 mol) was dissolved in 1,2-dichloroethane (60 ml) or ethanol-free chloroform. Ethyl diazoacetate (9.4 ml, 0089 mol) in the same solvent was added dropwise over a period of approximately 5 h under N$_2$ atmosphere. The solvent was then removed under vacuum and the mixture was taken upp in ethyl acetate, washed with NaHCO$_3$(aq), water and brine and the solvent removed. The product (33% cis, 66% trans) was purified by chromatography (0→10% ethyl acetate in n-hexane) to give 2.2 g of the title compound (30%).

d) cis-4,7-Difluoro-1,1a,2,7b-tetrahydro-cyclopropa [c]chromene-1-carboxylic acid

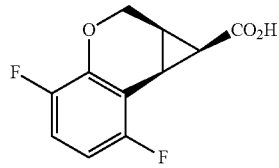

Cis-4,7-Difluoro-1,1a,2,7b-tetrahydro-cyclopropa[c] chromene-1-carboxylic acid ethyl ester (2 g, 0.008 mol) was heated in 1M LiOH in methanol-water (25%) at 80 deg. for 2 h. The volume was reduced to half and acidified. Extraction with ether followed by chromatography (silica gel, ether) gave pure title compound (35%)

Example 28

Additional Intermediates a) 6-Fluorochroman-4-ol

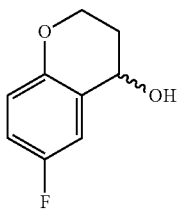

6-Fluorochroman-4-one (10 g, 61 mmol) was dissolved in ethanol (100 ml). NaBH$_4$ (excess) was added and cooled on icebath. The mixture was then left in room temperature for 2 h, followed by reflux for 4 h. Purification by chromatography (silica gel, ether-hexane, 1:5) gave 8. g (80%) pure 6-fluoro-chroman-4-ol.

b) 6-Fluoro-2H-chromene

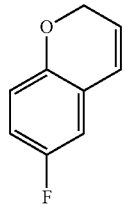

6-Fluorochroman-4-ol (8 g, 48 mmol) and toluene-4-sulphonic acid (1 g) were dissolved in toluene and refluxed over-night with subsequent water removal. The mixture was then cooled and washed with NaHCO$_3$ (aq) and purified by chromatography (silica gel, n-hexane) to give 4.2 g (52%) of pure 6-fluoro-2H-chromene.

c) +/−cis-6-Fluoro-1,1a,2,7b-tetrahydro-cyclopropa[c]chromene-1-carboxylic acid ethyl ester

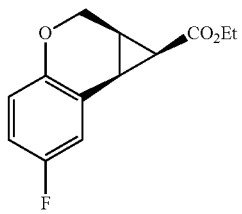

This Compound was prepared analogously to cis-4,7-Difluoro-1,1a,2,7b-tetrahydro-cyclopropa[c]chromene-1-carboxylic acid ethyl ester but using 6-fluoro-2H-chromene to give 1.9 (29%) of the title compound.

d) Cis-6-Fluoro-1,1a,2,7b-tetrahydro-cyclopropa[c]chromene-1-carboxylic acid

This compound was prepared analogously to cis-4,7-difluoro-1,1a,2,7b-tetrahydro-

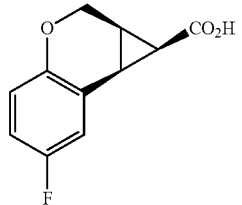

cyclopropa[c]chromene-1-carboxylic acid but using cis-6-fluoro-1,1a,2,7b-tetrahydro-cyclopropa[c]chromene-1-carboxylic acid ethyl ester (1.9 g, 8 mmol) to give 350 mg (21%) of pure cis-6-fluoro-1,1a,2,7b-tetrahydro-cyclopropa[c]chromene-1-carboxylic acid e) 1-Bromo-4-fluoro-2-prop-2-ynyloxy-benzene

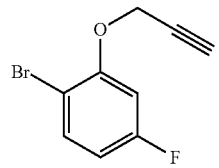

This compound was prepared analogously to 2,4-difluoro-2-prop-ynyloxy-benzene but using 2-bromo-5-fluorphenol (15 g, 78 mmol) to give 1-bromo-4-fluoro-2-prop-2-ynyloxy-benzene 15.6 g (87%)

f) 2-Bromo-4-fluoro-1-prop-2-ynyloxy-benzene

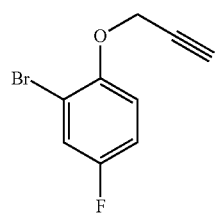

This compound was prepared analogously to 2,4-difluoro-2-prop-ynyloxy-benzene but using 2-bromo-4-fluoro-phenol (15 g, 78 mmol) to give 2-bromo-4-fluoro-1-prop-2-ynyloxy-benzene 15. g (84%).

g) 1,3-difluoro-5-prop-2-ynyloxy-benzene

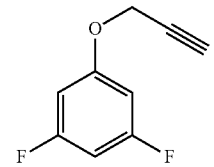

This compound was prepared analogously to 2,4-difluoro-2-propynyloxybenzene but using 3,5-difluoro-phenol (14 g, 107 mmol) to give 1,3-difluoro-5-prop-2-ynyloxy-benzene 12 g (67%).

h) 8-Bromo-6-fluoro-2H-chromene

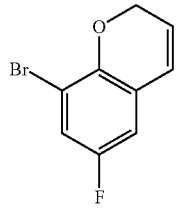

This compound was prepared analogously to 5,8-difluoro-2H-chromene but using (15 g, 65 mmol) of 2-bromo-4-fluoro-1-prop-2-ynyloxybenzene to give the title compound (7 g, 46%)

i) 8-Bromo-5-fluoro-2H-chromene

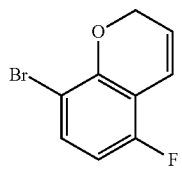

This compound was prepared analogously to 5,8-difluoro-2H-chromene but using (15 g, 65 mmol) of 1-bromo-4-fluoro-2-prop-2-ynyloxybenzene to give the title compound (3.7 g, 25 j) 5,7-Difluoro-2H-chromene

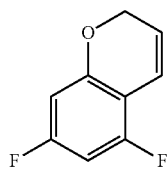

This compound was prepared analogously to 5,8-difluoro-2H-chromene but using (18 g, 107 mmol) of 1,3-difluoro-5-prop-2-ynyloxybenzene and PEG-200 as solvent to give the title compound (4 g, 23%).

k) +/−cis-4-Bromo-6-fluoro-1,1a,2,7b-tetrahydro-cyclopropa[c]chromene-1-carboxylic acid ethyl ester

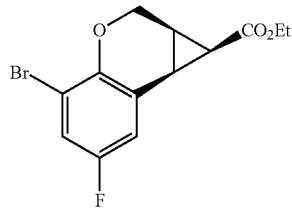

This compound was prepared analogously to +/−cis-4,7-difluoro-1,1a,2,7b-tetrahydro-cyclopropa[c]chromene-1-carboxylic acid ethyl ester but using 5 g (22 mmol) of 8-bromo 6-fluoro-2H-chromene to give 1.9 g (30%) of cis-6-fluoro-1,1a,2,7b-tetrahydro-cyclopropa[c]chromene-1-carboxylic acid ethyl ester.

l) +/−cis-4-Bromo-7-fluoro-1,1a,2,7b-tetrahydro-cyclopropa[c]chromene-1-carboxylic acid ethyl ester

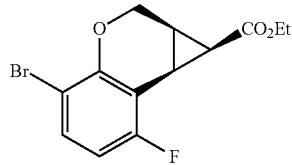

This compound was prepared analogously to +/−cis-4,7-difluoro-1,1a,2,7b-tetrahydro-cyclopropa[c]chromene-1-carboxylic acid ethyl ester but using 3.5 g (15.3 mmol) of 8-bromo-5-fluoro-2H-chromene to give 1.6 g (33%) of +/−cis-4-bromo-7-fluoro-1,1a,2,7b-tetrahydro-cyclopropa[c]chromene-1-carboxylic acid ethyl ester.

m) +/−cis-5,7-Difluoro-1,1a,2,7b-tetrahydro-cyclopropa[c]chromene-1-carboxylic acid ethyl ester

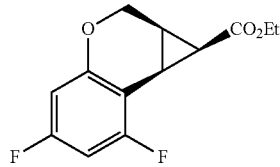

This compound was prepared analogously to +/−cis-4,7-difluoro-1,1a,2,7b-tetrahydro-cyclopropa[c]chromene-1-carboxylic acid ethyl ester but using 2 g (12 mmol) of 5,7-difluoro-2H-chromene to give 0.9 g (29%) of +/−cis-5,7-difluoro-1,1a,2,7b-tetrahydro-cyclopropa[c]chromene-1-carboxylic acid ethyl ester.

Example 29 a) Resolution of the racemic cis-7-fluoro-4-chloro-1,1a,2,7b-tetrahydro-cyclopropa[c]chromene-1-carboxylic acid 0.32 g (1.32 mmol) of racemic cis-7-fluoro-4-chloro-, 1a,2,7b-tetrahydro-cyclopropa[c]chromene-1-carboxylic acid was dissolved in hot acetonitrile (50 ml) and (1R,2R)-2-benzyloxycyclopentylamine (0.25 g, 1.32 mmol) was added. The resulting solution was left for crystallization. After few hours the mother liquor was decanted and crystals were washed with acetonitrile. The second crystallization from acetonitrile gave 92 mg of pure diastereomeric salt. The salt was treated with 1M HCl and resulting mixture was extracted with ethyl acetate. The organic phase was washed with water, brine and evaporated to give 0.05 g of enantiomeric cis-7-fluoro-4-chloro-1,1a,2,7b-tetrahydro-cyclopropa[c]chromene-1-carboxylic acid.

Example 30

+/−cis-N-(5-cyano-2-pyridinyl)-N'-(4,7-dichloro-1,1a,2,7b-tetrahydrocyclopropa[c]chromen-1-yl)urea a) 1,4-dichloro-2-(2-propynyloxy)benzene

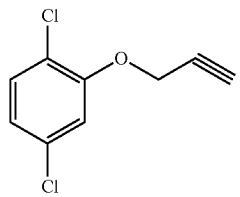

2,5-Dichlorophenol (8 g, 49 mmol) was mixed with potassium carbonate (13.6 g, 98 mmol) and 80% solution of propargyl bromide in toluene (11 ml, 98 mmol) in acetone (100 ml) and stirred overnight at room temperature. The precipitate was removed by filtration and washed with acetone. The acetone solution obtained was concentrated by rotary evaporation and kept under vacuum for 5 h. The product was obtained as yellow oil with quantitative yield. It was used for further transformations without additional purification.

b) 5,8-dichloro-2H-chromene

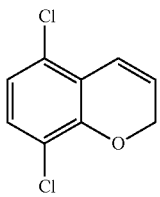

1,4-Dichloro-2-(2-propynyloxy)benzene was degassed and heated at stirring under argon for 4 h at 224° C. The reaction mixture was then distilled in Kugelrohr apparatus (150-175° C./4.1×10$^{-2}$ mbar) to give 3.58 g of desired product as white solid. Yield 36% from starting dichlorophenol.

c) +/−cis-ethyl 4,7-dichloro-1,1a,2,7b-tetrahydrocyclopropa[c]chromene-1-carboxylate

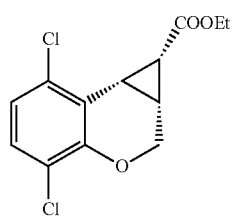

5,8-Dichloro-2H-chromene (3.15 g, 16 mmol), (Rh(II)Ac$_2$)$_2$ (30 mg, 0.1 mol %) was dissolved in degassed dry methylene chloride (3 ml). Ethyl diazoacetate (3 ml, 2 eq.) in the same solvent was added by a syringe at the flow rate 0.4 ml/h over a period of approximately 5 h under N$_2$ atmosphere. The reaction mixture was then washed with NH$_4$Cl (aq), water and brine and the solvent removed. The product (45% cis, 55% trans) was purified by chromatography on silica (200 g, ethyl acetate/n-hexane 1:15) to give 0.9 g of the pure cis product (racemate). Yield 20%. M$^+$=287.
$^1$H-NMR (CDCl$_3$): 7.15 (d, 1H, J=8.5 Hz), 6.91 (d, 1H, J=8.8 Hz), 4.59 (dd, 1H, J$_1$=12.02, J$_2$=7.03), 4.48 (dd, 1H, J$_1$=12.02, J$_2$=4.10), 4.07-3.94 (m, 3H), 2.62 (t, 1H, J=8.8 Hz), 2.27 (t, 1H, J=8.36 Hz), 2.20-2.12 (m, 1H), 1.1 (t, 3H).

d) +/−cis-4,7-dichloro-1,1a,2,7b-tetrahydrocyclopropa[c]chromene-1-carboxylic acid

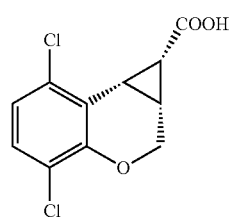

+/−cis-Ethyl 4,7-dichloro-1,1a,2,7b-tetrahydrocyclopropa[c]chromene-1-carboxylate was mixed with methanol (3 ml) and water solution of NaOH (1.5 eq., 3 ml) and heated at stirring for 1.5 h at 60° C. The extraction of basic reaction mixture into hexane showed that no starting material present. The reaction mixture was acidified with excess of 3M HCl solution (pH=1). The precipitate formed was collected by suction and washed with water. White solid obtained was dried under high vacuum (yield 80%).

Example 59A a) 5-chloro-2-fluorophenol

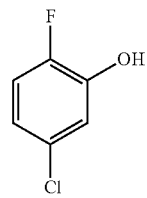

5-Chloro-2-fluoroaniline (10 g, 68 mmol) was dissolved in 6M sulfuric acid and cooled in ice/brine bath to −5° C. The solution of NaNO$_2$ (5.2 g, 76 mmol) in minimum amount of water was added dropwise to the stirred suspension at the temperature not higher then −2° C. After the addition clear yellow solution formed was allowed to stir for additional 30 min at cooling. CuSO$_4$ was dissolved water (80 ml) and mixed with sulfuric acid (32 ml). The diazonium salt solution was added dropwise to the preheated (160° C.) cuprous sulfate solution and the product was removed from the reaction flask by steam distillation. The reaction took about 2 h to be complete. The water/phnol solution was extracted into ether, washed with brine and dried over Na$_2$SO$_4$. Concentration gave 4 g of crude phenol (40%).

b) 4-chloro-1-fluoro-2-(2-propynyloxy)benzene

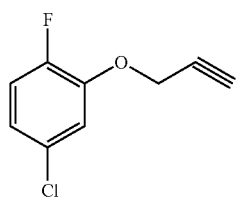

4-Chloro-1-fluoro-2-(2-propynyloxy)benzene was synthesized analogously to Example 33a from (4 g, 27 mmol) 4-chloro-1-fluorophenol to give 4.6 g of product (purified by column chromatography on silica, ethyl acetate/n-hexane 1:15) as yellow oil. Yield 90%.

c) 5-chloro-8-fluoro-2H-chromene

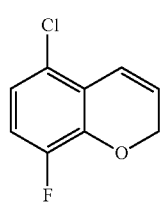

5-Chloro-8-fluoro-2H-chromene was synthesized analogously to Example 33b) from 4-chloro-1-fluoro-2-(2-propynyloxy)benzene (4.6 g, 25 mmol) to give 1 g of product (purified by column chromatography on alumina, ethyl acetate/n-hexane 1:15) as colourless oil. Yield 22%.

d) ethyl +/−cis-7-chloro-4-fluoro-1,1a,2,7b-tetrahydrocyclopropa[c]chromene-1-carboxylate

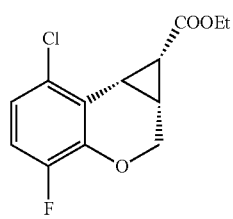

Ethyl +/−cis-7-chloro-4-fluoro-1,1a,2,7b-tetrahydrocyclopropa[c]chromene-1-carboxylate was synthesized analogously to Example 33c from 5-chloro-8-fluoro-2H-chromene (1 g, 5.4 mmol) to give 360 mg of +/−cis product (purified by column chromatography on silica, ethyl acetate/n-hexane 1:20) as white solid. Yield 25%.

e) +/−cis-7-chloro-4-fluoro-1,1a,2,7b-tetrahydrocyclopropa[c]chromene-1-carboxylic acid

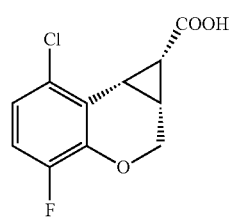

+/−cis-7-Chloro-4-fluoro-1,1a,2,7b-tetrahydrocyclopropa[c]chromene-1-carboxylic acid was synthesized analogously to Example 33d from ethyl +/−cis-7-chloro-4-fluoro-1,1a,2,7b-tetrahydrocyclopropa[c]chromene-1-carboxylate (360 mg, 1.3 mmol) to give 259 mg of +/−1-cis acid (80%).

Example 31

N-[(1S,1aR,7bR) or (1R,1aS,7bS)-1,1a,2,7b-tetrahydrocyclopropa[c]-[1]benzothiopyran-1-yl]-N'-(5-cyano-2-pyridinyl)urea a) 3,4-dihydro-2H-1-benzothiopyran-4-ol

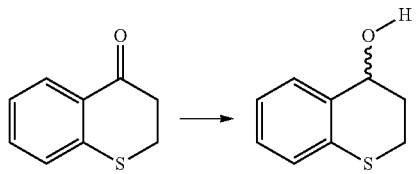

A solution of thiochroman-4-one (9 g) in ether (27 ml) was added slowly to a mixture of lithium aluminium hydride (0.53 g) in ether (54 ml). After the end of the addition, the mixture was refluxed for 2 hours. The reaction mixture was cooled and ice was added, followed by water and by a solution of 20% $H_2SO_4$. The water phase was washed twice with ether. The ether phase was washed twice with NaOH 2N, and once with water, dried over $MgSO_4$ and evaporated. The clear oil (8.9 g) crystallised after few hours. Rdt=97% b) 2H-1-benzothiopyran and 4H-1-benzothiopyran

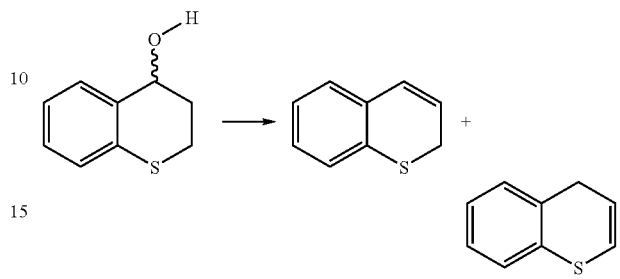

4-Thiochromanol (8.9 g) and potassium acid sulfate (0.89 g) were placed in a flask and evacuated to 1 mm. The flask was put in a bath heated at 90° C. until the alcohol melted. The magnetic stirrer was started and the bath slowly brought to 120° C. Dehydration was rapid and a mixture of the product and water distilled and was collected in a ice-cooled receiver. The product was taken up in ether and dried. The crude product (7 g, Rdt=88%) wasn't purified. The NMR showed the presence of 10% of the 4H-1-benzothiopyran.

c) Ethyl ester 1,1a,2,7b-tetrahydro-cyclopropa[c][1]benzothiopyran-1-carboxylic acid, (1S,1aR,7bR) or (1R,1aS,7bS)

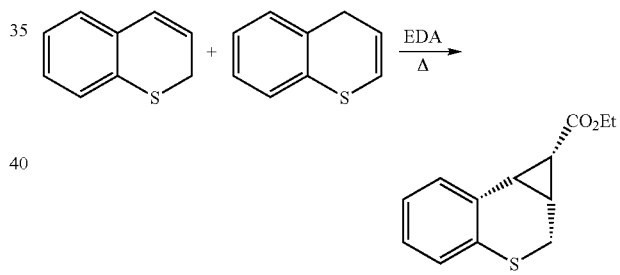

Ethyl diazoacetate was added slowly to 500 mg of thiochromene at 140 C. The reaction was followed by Gas chromatography and stopped when all starting material was consumed (about 7 hours). The residue was purified by flash chromatography (5% ether in hexane). The cis isomer (46.5 mg, Rdt=6%) was identified by NMR spectroscopy.

d) 1,1a,2,7b, tetrahydro-cyclopropa[c][1]benzothiopyran-1-carboxylic acid, (1S, 1aR,7bR) or (1R,1aS, 7bS)

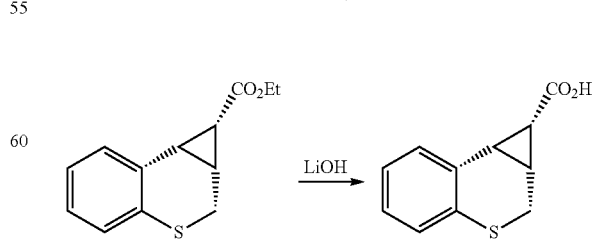

A mixture of the cis isomer (46.5 mg), LiOH (4 eq., 19 mg) in 5 ml of methanol/25% $H_2O$ was refluxed for 1 hour. After evaporation of the solvent under vacuum, the residue was dissolved in water and washed with ether. The water phase was acidified with concentrated HCl, and extracted twice with dichloromethane. After drying, the organic phase was evaporated and gave the desired acid (30 mg). Rdt=73%.

Example 32

(1S,1aR,7bS)-4,7-difluoro-1,1a,2,7b-tetrahydrocyclopropa[c]chromene-1-carboxylic acid a) (2Z)-3-(3,6-difluoro-2-methoxyphenyl)-2-propen-1-ol

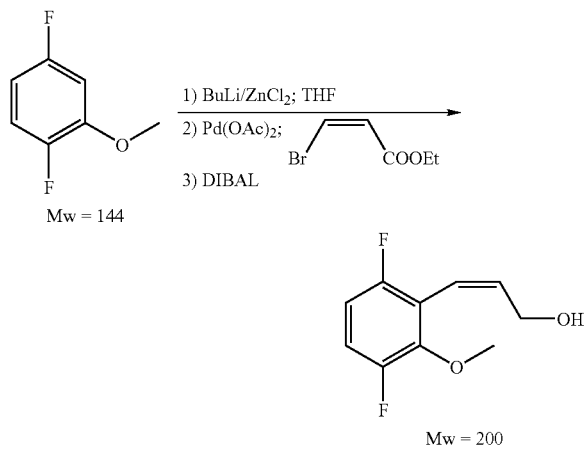

solution of BuLi (2.5M) in hexane (9.6 ml; 0.024 mol) was added to a stirred solution of 2,5-difluoroanisol (2.88 g, 0.02 mol) in dry THF (30 ml) at −70 C, followed after 2 h by solution of zinc chloride (3.6 g; 0.026 mol) in dry THF (50 ml). The reaction temperature was allowed to raise to room temperature and then stirring was maintained at room temperature for 30 min. Pd(OAc)$_2$ (8 mg; 0.2 mol %) was added, followed by ethyl cis-3-bromoacrylate (3.58 g; 0.02 mol). The reaction mixture was placed in preheated oil bath and heated under reflux for 1 h. The resulting reaction mixture was chilled to −78 C and 60 ml (0.06 mol) of DIBAL (1M solution in hexanes) was added dropwise. The stirring was continued at −78 C for 2 h and 1 h at room temperature. The reaction was quenched with water and all solids were dissolved by addition of HCl. The organic phase was diluted with ether, separated, washed with 5N HCl, brine and evaporated in vacuo. The residue was Kugelrohr distilled (1.5×10$^{-2}$ mbar, 150 C) to give 3.7 g (92%) of crude (2Z)-3-(3,6-difluoro-2-methoxyphenyl)-2-propen-1-ol, which contains~6% of other regioisomers. The crude product was used in the next step without further purification.

$^1$H-NMR (CDCl$_3$): 7.00 (m, 1H); 6.77 (m, 1H); 6.31 (app. d, 1H); 6.12 (app. dt, 1H); 4.08 (br. t, 2H); 3.89 (d, 3H); 1.80 (br. t, 1H).

b) (2Z)-3-(3,6-difluoro-2-methoxyphenyl)prop-2enyl diazoacetate

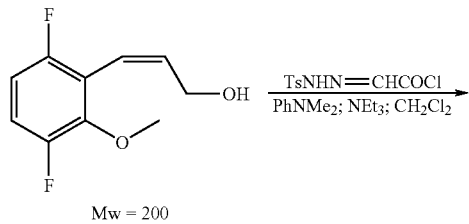

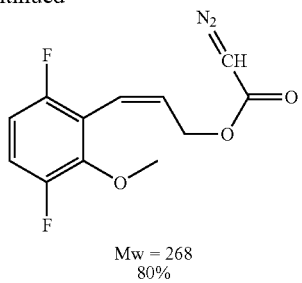

The p-toluenesulfonylhydrozone of glyoxylic acid chloride (5.16 g; 0.02 mol) was added to a solution of (2Z)-3-(3,6-difluoro-2-methoxyphenyl)-2-propen-1-ol (3.6 g; 0.018 mol) in dry CH$_2$Cl$_2$ (50 ml) at −5 C, and N,N-dimethylaniline (2.5 ml; 0.02 mol) was added slowly. After stirring for 30 min at −5 C, Et$_3$N (12 ml; 0.09 mol) was added slowly. The resulting mixture was stirred for 15 min at −5 C and then for 30 min at room temperature, whereupon water (~50 ml) was added. The organic phase was separated washed with water, brine and concentrated in vacuo. Flash chromatography (silica, EA:Hex; 1:15) gave 3.86 g (80%) of product as a yellow solid.

$^1$H-NMR (CDCl$_3$): 7.00 (m, 1H); 6.76 (m, 1H); 6.41 (app. d, J=12.2 Hz; 1H); 6.00 (app. dt, J=12.2; 6.10 Hz; 1H); 4.71 (br. s, 1H); 4.67 (dt, 2H); 3.89 (d, 3H).

c) (1S,5R,6S)-6-(3,6-difluoro-2-methoxyphenyl)-3-oxabicyclo[3.1.0]hexan-2-one

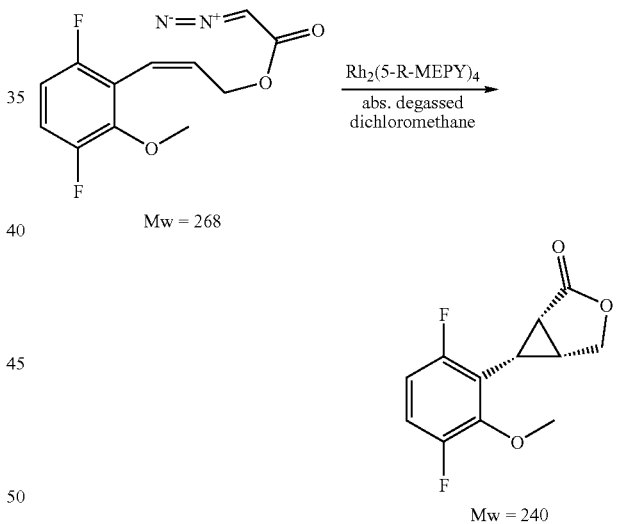

(2Z)-3-(3,6-difluoro-2-methoxyphenyl)prop-2enyl diazoacetate (3.45 g, 0.013 mol) was dissolved in 100 ml of dried degassed dichloromethane and added dropwise to the solution of chiral Doyle catalyst (Aldrich, also available from Johnsson Matthey, 10 mg, 0.1 mol %) in 50 ml of dichloromethane under argon at ambient temperature over a period of ~6 h. The initial blue color had turned to olive by the end of the addition. The reaction mixture was concentrated in vacuo and the crude product was purified by flash chromatography (silica, EA:Hex, 1:5→1:1) to give 2.72 g (88%) of (1S,5R,6S)-6-(3,6-difluoro-2-methoxyphenyl)-3-oxabicyclo[3.1.0]hexan-2-one as colorless solid. Enantiomeric purity could be checked on this stage using Chiracel OD column, 10% IPA in hexane—94% ee.

$^1$H-NMR (CDCl$_3$): 7.00 (m, 1H); 6.72 (m, 1H); 4.33 (dd, 1H); 4.10 (d, 1H); 4.02 (d, 3H); 2.66 (m, 2H); 2.37 (t, 1H).

d) (1S,1aR,7bS)-1-(bromomethyl)-4,7-difluoro-1a, 7b-dihydrocyclopropa[c]chromene-2(1H)-one

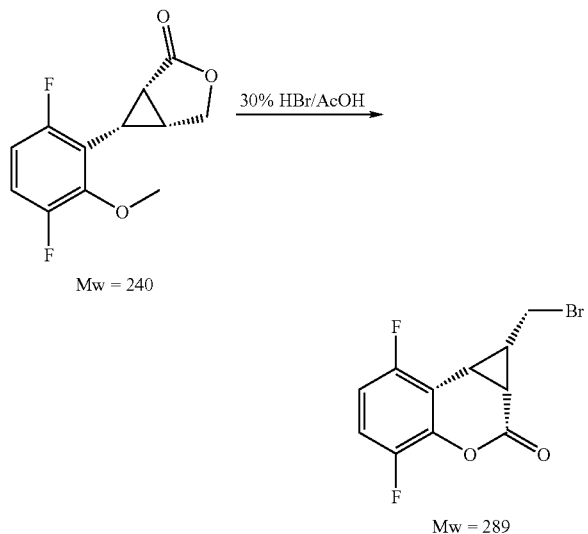

(1S,5R,6S)-6-(3,6-difluoro-2-methoxyphenyl)-3-oxabicyclo[3.1.0]hexan-2-one (130 mg, 0.55 mmol) was mixed with 1.2 ml of 30% HBr/AcOH (6 mmol) and heated in a sealed vessel at stirring for about 4 h at 90° C. The reaction mixture was then cooled down, mixed with water and extracted into diethyl ether (3×20 ml). Ether extract was washed with sat. sodium bicarbonate solution and brine. Dried over magnesium sulfate. Concentration gave 160 mg of white solid material. 98% yield.

$^1$H-NMR (CDCl$_3$): 7.08 (m, 1H); 6.88 (m, 1H); 3.44 (dd, 1H); 3.06 (t, 1H); 2.96 (dd, 1H); 2.64 (dd, 1H); 2.46 (m, 1H).

e) (1S,1aR,7bS)-4,7-difluoro-1,1a,2,7b-tetrahydrocyclopropa[c]chromene-1-carboxylic acid

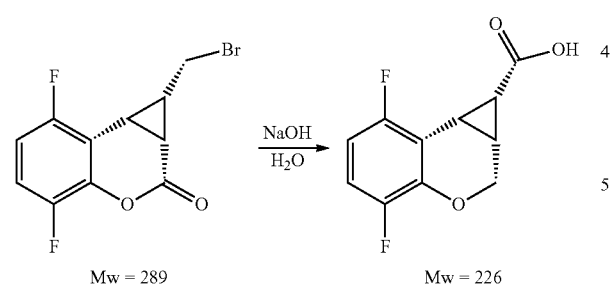

(1S,1aR,7bS)-1-(bromomethyl)-4,7-difluoro-1a,7b-dihydrocyclopropa[c]chromen-2(1H)-one (360 mg, 1.2 mmol) was mixed with the solution of NaOH (0.1 g, 2.5 mmol) in 5 ml of water and heated at stirring for 1 h at 90° C. After completion the reaction mixture was cooled down and extracted into diethyl ether (2×20 ml). Water phase was acidified with conc. HCl. The precipitate formed was collected by filtration to give 180 mg of pure product. Mother liquor was extracted into ether and washed with brine, dried over magnesium sulfate. Concentration gave additional 70 mg of product (containing up to 15% of impurities). Overall yield about 92%.

$^1$H-NMR (CDCl$_3$): 6.86 (m, 1H); 6.54 (m, 1H); 4.48 (m, 2H); 2.62 (t, 1H); 2.20 (t, 1H); 2.11 (m, 1H).

Example 33 a) cis ethyl ester 1a, 6b-dihydro-1H-benzo[b]cyclopropa[d]thiophene-1-carboxylic acid, (1S,1aS,6bR) or (1R,1aR,6bS)

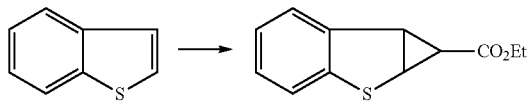

Ethyl diazoacetate is added slowly to 10 g of thiophene at 140° C. The reaction was checked by gas chromatography and stopped after 7 hours. The residue is purified by flash chromatography (5% ether in hexane). The cis isomer (917 mg, Rdt=6%) was identified by NMR spectroscopy.

REFERENCE

Badger G. M. et al, *J. Chem. Soc.*, 1958, 1179-1184.
Badger G. M. et al, *J. Chem. Soc.*, 1958, 4777-4779.

b) cis 1a, 6b-dihydro-1H-benzo[b]cyclopropa[d]thiophene-1-carboxylic acid, (1S,1aS,6bR) or (1R,1aR,6bS)

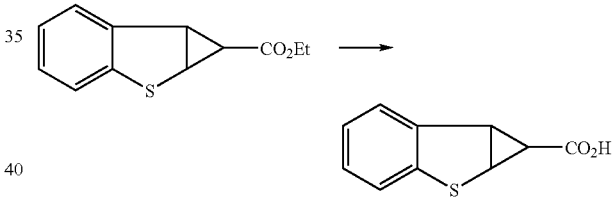

A mixture of the cis isomer (443 mg), LiOH (193 mg) in 15 ml of methanol/25% H$_2$O is refluxed for 1 hour. After evaporation of the solvent under vacuum, the residue is dissolved in water and washed with ether. The water phase is acidified with concentrated HCl, and extracted twice with dichloromethane. After drying, the organic phase is evaporated and gave the desired acid (313.6 mg). Rdt=81%.

Example 34

(1S,5R,6S)-6-(3,6-difluoro-2-methoxyphenyl)-2-methoxy-3-oxabicyclo[3.1.0]hexane

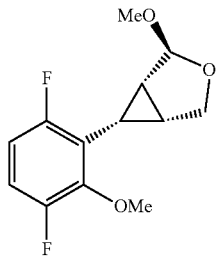

a) Iodo-3-oxabicyclo[3.1.0]hexan-2-one

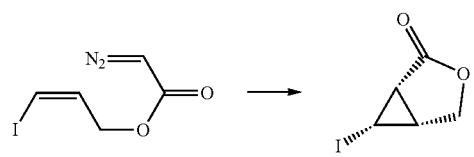

The title compound is synthesised in the depicted stereochemistry as described in Doyle J Amer Chem Soc 117 (21) 5763-5775 (1993)

b) Iodo-2-methoxy-3-oxabicyclo[3.1.0]hexane

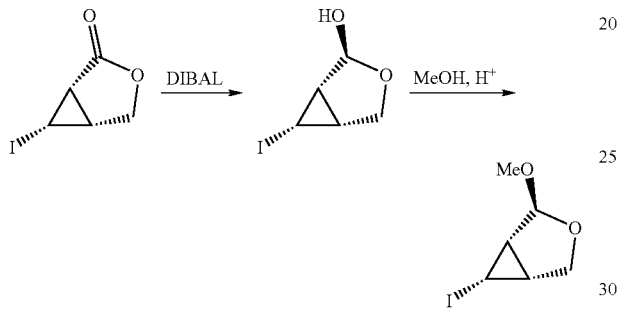

The title compound is synthesised in the depicted stereochemistry as described in Martin et al Tett Lett 39 1521-1524 (1998).

c) (1S,5R,6S)-6-(3,6-difluoro-2-methoxyphenyl)-2-methoxy-3-oxabicyclo[3.1.0]hexane

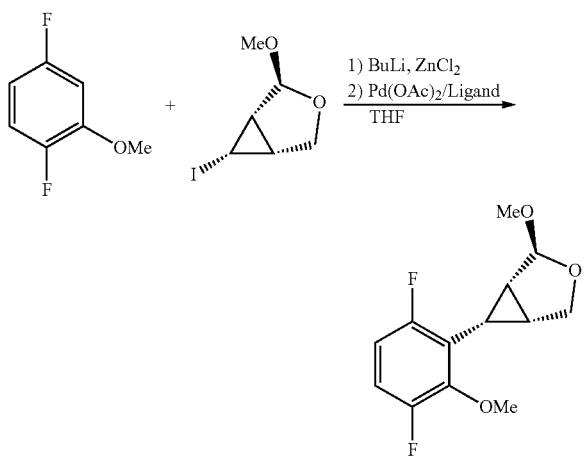

2,4-difluoroanisol (90 mg, 0.62 mmol) was dissolved in anhydrous, degassed, THF (7 ml) and cooled to −78° C. under $N_2$. nBuLi, 2.5 M in hexane, (0.30 ml, 0.77 mmol) was added and the reaction mixture was stirred at −78° C. for 2 hrs. $ZnCl_2$ (150 mg, 1.1 mmol), as a solution in anhydrous THF (7 ml), was added and the reaction mixture was allowed to warm to ambient temperature for 2 hrs. Iodo-2-methoxy-3-oxabicyclohexane (150 mg, 0.63 mmol), Pd (OAc)$_2$ (1.5 mg, 6.2 μmol), and ligand Tris(2,4-di-tert-butylphenyl)phosphite (40 mg, 62 μmol) were mixed in anhydrous THF (7 ml) and added to the reaction mixture. The reaction mixture was heated at reflux for 3 days and quenched with $H_2O$. Diethyl ether was added and the layers were separated, the organic layer was washed with $H_2O$ and aq. sat. NaCl, dried over $MgSO_4$, filtered and concentrated to give the title compound, otherwise denoted 2,4-di-fluoro-5-(cyclopropylacetal)anisol. Column chromatography on silica (EtOAc/Hexane 1:3) gave (4) 50 mg, 31%.

$^1$H NMR (CDCl$_3$) 7 (ppm): 6.88-6.94 (m, 1H, ArH), 6.68-6.73 (m, 1H, ArH), 4.82 (s, 1H, CHOCH$_3$), 3.97-3.98 (m, 1H, CHOCH) 3.94 (s, 3H, OCH$_3$), 3.79-3.81 (m, 1H, CHOCH) 3.30 (s, 3H, OCH$_3$), 2.13-2.19 (m, 2H, 2×CH-cyclopropyl), 1.89 (tr, J=7.81 Hz, 1H, CH cyclopropyl).

Example 35 cis-4,7-Difluoro-1,1a,2,7b-tetrahydro-cyclopropa[c]chromene-1-carboxylic acid

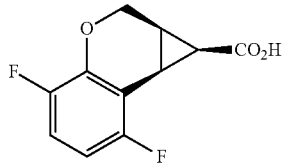

BBr$_3$ 1M solution in CH$_2$Cl$_2$ (5.8 ml; 5.8 mmol 2.1 eq) was added to starting lactone, (1S,5R,6S)-6-(3,6-difluoro-2-methoxyphenyl)-3-oxabicyclo[3.1.0]hexan-2-one from example 42c) (0.66 g; 2.75 mmol) at 0° C. The reaction mixture was stirred at 0° C. for 1 h. Acetonitrile (5.8 ml) was added and stirring was continued for 3 h at 0° C. The reaction mixture was quenched by addition of water and the organic phase was separated. Water phase was extracted with CH$_2$Cl$_2$ and combined organic phases were evaporated. NaOH (0.33 g; 8.25 mmol; 3 eq) in water (~5 ml) was added to the resulted residue and stirred at 80° C. for 45 min. The reaction mixture was extracted with ether to remove none acidic impurities. The residual ether in water phase was evaporated in vacuo and conc. HCl was added to pH of ~3. After ~1 h the solid was filtered off yielding 0.497 g (80%) of crude final acid as brownish solid. The crude acid was dissolved in 6 ml of EtOH/H$_2$O (40/60 v/v) and treated with activated carbon. The hot solution was filtered and left for crystallization. Yield 0.4 g (64%).

$^1$H-NMR (CDCl$_3$): 10.32 (br s, ~1H), 7.68 (d, 2H), 7.37 (s, 1H), 7.32 (d, 2H), 6.96 (s, 1H), 6.87 (m, 1H), 6.62 (dt, 1H), 4.44 (dd, 1H), 4.33 (dd, 1H), 3.53 (m, 1H), 2.56 (m, ~1H), 1.96 (m, 1H). LC-MS: M$^+$434.

Example 36 a) 1,1a,66a-tetrahydrocyclopropa[a]indene-1-carboxylic acid ethyl ester

Indene is diluted in 100 ml dichloroethane. Around 10 mg of CuI and around 10 mg Pd(OAc)$_2$ is added. 25 ml of the resultant mixture is dropwise added to 25 ml ethyldiazoacetate and refluxed for 30 minutes. The solution is filtered through Al$_2$O$_3$ which is eluted with a EtOAC/hexane gradient. The eluate is evaporated vigorously at 100°, 2 mmHg to yield the title compound (36 g).

b) 1,1a,66a-tetrahydrocyclopropa[a]indene-1-amine

The product of step a) is boiled with around 50 g NaOH in 200 ml 10:1 MeOH:H$_2$O for 2 hours. The mixture is diluted with water, washed with dichloroethane, evaporated with HOAc, extracted with dichloroethane, washed with water, dried with sulphate, filtered and evaporated to yield 25 g of the acid, 95% pure. DPPA 275.2 δ=1.128 10 ml, 46.5 mmol TEA 7.1 ml 1.1 ee and 7.3 g of the acid (mass 174.12, 0.9 ee) is mixed in 200 ml toluene and refluxed for around 2 hours. The product is evaporated and dissolved in dioxane 200 ml. 25 ml HCl(aq) and 25 ml water is added and the mixture agitated for 60 minutes at room temperature. The solution is partioned with acid/base in water/dichloroethane. The organic phase is dried, filtered and evaporated. The product is chromatographed through a silica 60 column to yield 660 mg of 85% pure cis amine, mol wt 145.11.

Example 37

±cis-1-(5-Cyano-pyridin-2-yl)-3-(1,1a,6,6a-tetrahydro-cyclopropa[a]inden-1-yl)urea a) ±cis-1,1a,6,6a-Tetrahydro-cyclopropa[a]indene-1-carboxylic acid ethyl ester To a mixture of indene (11.6 g, 100 mmol) and Cu$_2$Br$_2$ (0.10 g, 0.35 mmol) in 1,2-

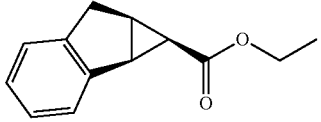

dichloroethane (200 mL) at 80° C., was added dropwise (3 h) a solution of ethyl diazoacetate (17.1 g, 150 mmol) in 1,2-dichloroethane (35 mL). After 15 min at 80° C., the reaction mixture was washed with H$_2$O (200 mL). The H$_2$O phase was washed with CH$_2$Cl$_2$ (50 mL) and the solvent of the combined organic phases was removed under reduced pressure. The crude product was column chromatographed (silica gel, 5→10% EtOAc in Hexane), to give 3.63 g (18%) of ±cis-1,1a,6,6a-tetrahydrocyclopropa[a]indene-1-carboxylic acid ethyl ester and 6.68 g (33%) of ±trans-1,1a,6,6a-tetrahydro-cyclopropa[a]indene-1-carboxylic acid ethyl ester as a byproduct.

$^1$H-NMR(CDCl$_3$): 7.30-7.05 (m, 4H), 3.81 (q, 2H), 3.36 (d, 1H), 3.18 (dd, 1H), 2.92 (m, 1H), 2.24 (m, 1H), 1.99 (dd, 1H), 0.92 (t, 3H).

b)±cis-1,1a,6,6a-Tetrahydrocyclopropa[a]inden-1-carboxylic acid

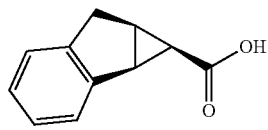

±cis-1,1a,6,6a-Tetrahydro-cyclopropa[a]indene-1-carboxylic acid was synthesized from ±cis-1,1a,6,6a-tetrahydrocyclopropa[a]indene-1-carboxylic acid ethyl ester (3.53 g, 15.5 mmol), LiOH (539 mg, 22.5 mmol), H$_2$O (10 mL) and MeOH (20 mL) which were heated to reflux for 2 h, concentrated and acidified to precipitate 1.62 g (62%) of ±cis-1,1a,6,6a-tetrahydro-cyclopropa[a]indene-1-carboxylic acid as a white solid. The product was not crystallized.

$^1$H-NMR (CDCl$_3$): 10.95 (br s, 1H), 7.35-7.02 (m, 4H), 3.29 (d, 1H), 3.14 (dd, 1H), 2.96 (m, 1H), 2.27 (m, 1H), 1.91 (dd, 1H).

The reaction mixture was concentrated under reduced pressure, benzene (20 mL) was added and the reaction mixture was washed with 1N HCl (30 mL), H$_2$O (30 mL) and brine (30 mL). The solvent of the organic phases was removed under reduced pressure. The crude product was column chromatographed (silica gel, 4→5% MeOH in CH$_2$Cl$_2$), to give 25 mg (5%) of ±cis-1-(5-cyano-pyridin-2-yl)-3-(1,1a,6,6a-tetrahydro-cyclopropa[a]inden-1-yl)-urea.

$^1$H-NMR (DMSO-d$_6$): 9.58 (s, 1H), 8.18 (d, 1H), 7.96 (dd, 1H), 7.40-7.25 (m, 3H), 7.17-7.05 (m, 3H), 3.27-3.13 (m, 2H), 2.80-2.73 (m, 2H), 2.05 (dd, 1H).

Example 38

±cis-1-(5-Cyano-pyridin-2-yl)-3-(1a,2,3,7b-tetrahydro-cyclopropa[a]naphthalen-1-yl)-urea a) 1a,2,3,7b-Tetrahydro-1H-cyclopropa[a]naphthalene-1-carboxylic acid ethyl ester

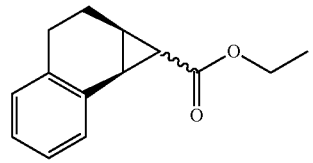

1a,2,3,7b-Tetrahydro-1H-cyclopropa[a]naphthalene-1-carboxylic acid ethyl ester was synthesized analogously to Example 37 from 1,2-dihydronaphthalene (3.91 g, 30 mmol), to give 688 mg (11%) of 1a,2,3,7b-tetrahydro-1H-cyclopropa[a]naphthalene-1-carboxylic acid ethyl ester (a 56/39 mixture of cis and trans isomers).

$^1$H-NMR (CDCl$_3$): 7.35-6.95 (m, 4H), 4.30-3.85 (m, 2H), 2.90-1.00 (m, 10H).

b) 1a,2,3,7b-Tetrahydro-1H-cyclopropa[a]naphthalene-1-carboxylic acid

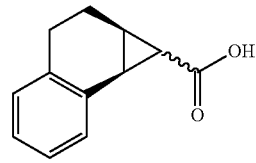

1a,2,3,7b-Tetrahydro-1H-cyclopropa[a]naphthalene-1-carboxylic acid was synthesized analogously to Example 37b from 1a,2,3,7b-tetrahydro-1H-cyclopropa[a]naphthalene-1-carboxylic acid ethyl ester (688 mg, 3.18 mmol, a 56/39 mixture of cis and trans isomers), to give 540 mg (90%) of 1a,2,3,7b-tetrahydro-1H-cyclopropa[a]naphthalene-1-carboxylic acid (a 56/39 mixture of cis and trans isomers). The product was not crystallized.

$^1$H-NMR (CDCl$_3$): 11.36 (br s, 1H), 7.30-6.95 (m, 4H), 2.80-1.65 (m, 7H).

Example 68 a) 1,1a,2,3,4,8b-Hexahydro-benzo[a]cyclopropa[c]cycloheptene-1-carboxylic acid ethyl ester

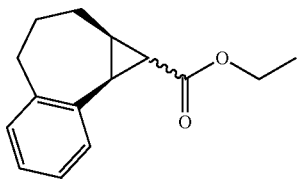

1,1a,2,3,4,8b-Hexahydro-benzo[a]cyclopropa[c]cycloheptene-1-carboxylic acid ethyl ester was synthesized analogously to Example 37a from 6,7-dihydro-5H-benzocycloheptene (4.40 g, 30.5 mmol), to give 3.43 g (49%) of 1,1a,2,3,4,8b-hexahydro-benzo[a]cyclopropa[c]cycloheptene-1-carboxylic acid ethyl ester (a 1/10 mixture of cis and trans isomers).
$^1$H-NMR (CDCl$_3$): 7.40-6.90 (m, 4H), 4.30-4.00 (m, 2H), 3.30-0.50 (m, 12H).

b) 1,1a,2,3,4,8b-Hexahydro-benzo[a]cyclopropa[c]cycloheptene-1-carboxylic acid

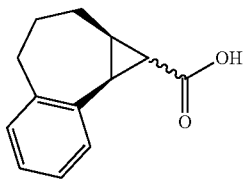

1,1a,2,3,4,8b-Hexahydro-benzo[a]cyclopropa[c]cycloheptene-1-carboxylic acid was synthesized analogously to Example 37 from 1,1a,2,3,4,8b-hexahydro-benzo[a]cyclopropa[c]cycloheptene-1-carboxylic acid ethyl ester (3.43 g, 14.9 mmol, a 1/10 mixture of cis and trans isomers), to give 2.81 g (93%) of 1,1a,2,3,4,8b-hexahydro-benzo[a]cyclopropa[c]cycloheptene-1-carboxylic acid (a 1/10 mixture of cis and trans isomers). The product was not crystallized.
$^1$H-NMR (CDCl$_3$): 10.76 (br s, 1H), 7.40-7.00 (m, 4H), 3.30-0.50 (m, 9H).

Example 40 a) 6-methoxy-1,2,3,4-tetrahydronaphthalen-1-ol

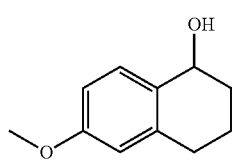

6-Methoxytetralone (10 g, 0.057 mol) was mixed with 150 ml of dry ethanol and sodium borohydride (1.2 eq) was added by portions to the stirred mixture. The reaction mixture was left to stir at ambient temperature for 15 h. The reaction mixture was then concentrated by rotary evaporation, mixed with 100 ml of water and heated for 1 h at 45° C. The resulting mixture was extracted into diethyl ether (3×80 ml). Combined organic extract was dried over Na$_2$SO$_4$ and concentrated by rotary evaporation to give 10.39 g of yellow oil which was used in the next step without additional purification.

b) 7-methoxy-1,2-dihydronaphthalene

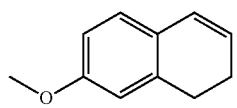

Crude 6-methoxy-1,2,3,4-tetrahydronaphthalen-1-ol (10.3 g, 0.058 mol) was dissolved in 100 ml of toluene and heated in an oil bath (115° C.). P-tolylsulphonic acid (20 mg) was added to the reaction mixture and it was refluxed for about 1 h. The reaction was monitored by GC. The reaction mixture was then cooled and washed with sat. NaHCO$_3$ solution, water and brine and organic layer was dried over Na$_2$SO$_4$. Concentration gave 8.879 of light brown oil. Yield 96%.

c) Ethyl 5-methoxy-1a,2,3,7b-tetrahydro-1H-cyclopropa[a]naphthalene-1-carboxylate

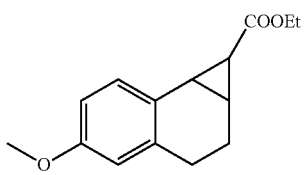

7-Methoxy-1,2-dihydronaphthalene (8.8 g, 0.055 mol) was mixed with 10 ml of degassed absolute methylene chloride and 20 mg of rhodium acetate (appr. 0.1 mol %). The reaction mixture was bubbled with nitrogen and ethyl diazoacetate (2 eq, 50% solution in degassed abs. methylene chloride) was added slowly through the syringe (flow rate about 1 ml/hour) to the stirred solution at ambient temperature. Gas evolution started upon the addition. The reaction was monitored by GC. Additional amount of catalyst was added during the reaction (about 20 mg). GC-ratio of cis/trans isomers was 21:48.

After the reaction was complete according to GC data the reaction mixture was washed with saturated NH$_4$Cl solution and brine. The methylene chloride solution was dried over Na$_2$SO$_4$. Concentration gave 13 g of crude product as yellow oil. Purified by column chromatography on silica (200 g, ethyl acetate/hexane 1:20). Only trans isomer was obtained in pure form. The required cis form could not be purified by the technique used. Fractions which were more enriched with required product were combined (200 mg, cis/trans ratio 70:30 according to GC) and used for further transformations.

d) 5-Methoxy-1a,2,3,7b-tetrahydro-1H-cyclopropa[a]naphthalene-1-carboxylic acid

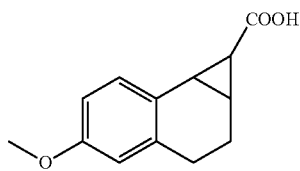

Ethyl 5-methoxy-1a,2,3,7b-tetrahydro-1H-cyclopropa[a]naphthalene-1-carboxylate (0.2 g, 0.8 mmol) was dissolved in 2 ml of methanol and the solution of sodium hydroxide (0.2 g, 50 mmol) in 2 ml of water was added to the reaction mixture and stirred at ambient temperature overnight. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over $Na_2SO_4$ and concentrated by rotary evaporation to give 0.15 g of mixture of cis/trans acids as white solid.

Example 41 a) 7-methoxy-1,2,3,4-tetrahydro-1-naphthalenol

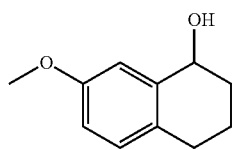

7-Methoxy-3,4-dihydro-1 (2H-naphthalenol was synthesized analogously to Example 69a from 7-methoxy-1,2,3,4-tetrahydro-1-naphthalenone (5 g, 28 mmol), to give about 5 g of crude product (quantitative yield), which was used in the next step without additional purification.

b) 6-methoxy-1,2-dihydronaphthalene

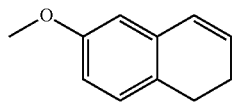

6-Methoxy-1,2-dihydronaphthalene was synthesized analogously to Example 40b from 7-methoxy-1,2,3,4-tetrahydro-1-naphthalenol to give 4.4 g of product as brown yellow oil (96% yield from 7-methoxy-1,2,3,4-tetrahydro-1-naphthalenone).

c) Ethyl 6-methoxy-1a,2,3,7b-tetrahydro-1H-cyclopropa[a]naphthalene-1-carboxylate

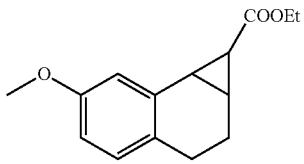

Ethyl 6-methoxy-1a,2,3,7b-tetrahydro-1H-cyclopropa[a]naphthalene-1-carboxylate was synthesized analogously to Example 38 from 6-methoxy-1,2-dihydronaphthalene (4.4 g, 28 mmol) at addition rate 0.7 ml/h to give 9.68 g of crude product as orange-brown oil. Purified by column chromatography on silica (200 g, ethylacetate/hexane 1:10). Three fractions were collected: fraction enriched with cis isomer (75% by GC)—0.16 g, mixed fraction—1.76 g, and fraction contained pure trans isomer—1 g. Total yield 45%.

d) 6-methoxy-1a,2,3,7b-tetrahydro-1H-cyclopropa[a]naphthalene-1-carboxylic acid

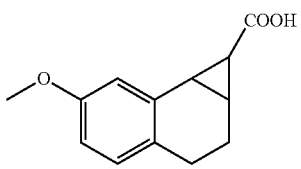

6-Methoxy-1a,2,3,7b-tetrahydro-1H-cyclopropa[a]naphthalene-1-carboxylic acid was synthesized analogously to Example 69d) from ethyl 6-methoxy-1a,2,3,7b-tetrahydro-1H-cyclopropa[a]naphthalene-1-carboxylate (0.16 g, 0.65 mmol) to give 0.1 g of product as white crystals. Yield 71%.

Example 42 a) 7,8-dihydro-2-naphthalenol

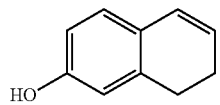

7-Methoxy-1,2-dihydronaphthalene (6.4 g, 40 mmol) was dissolved in abs. DMF and bubbled with argon sodium ethylthiolate (2.5 eq) was added and the reaction mixture was heated at stirring at 160° C. for about 4 h. Reaction was monitored by GC. Reaction mixture was diluted with water, acidified with 3M HCl and extracted into ethylacetate. Organic extract was washed with water and brine, dried over $Na_2SO_4$ and concentrated by rotary evaporation. Purification by column chromatography on silica (200 g, ethylacetate/hexane) gave 5.36 g of desired phenol. Yield 92%.

b) 7,8-dihydro-2-naphthalenyl trifluoromethanesulfonate

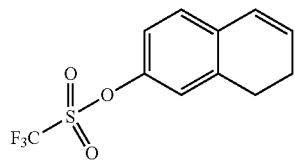

7,8-Dihydro-2-naphthalenol (5.3 g, 37 mmol) was mixed with triethylamine (6.2 ml, 44 mmol) in abs. methylenechloride and cooled under nitrogen in the ice/brine bath. Triflic anhydride (7.4 ml, 44 mmol) was added to the stirred solution through syringe during 10 min. The temperature was allowed to rise slowly up to room temperature. The reaction mixture was then washed with water and brine and dried over $Na_2SO_4$.

The crude product was purified by column chromatography on silica. 9 g of brown liquid was obtained. Yield 88%.

c) Ethyl 5-{[(trifluoromethyl)sulfonyl]oxy}-1a,2,3, 7b-tetrahydro-1H-cyclopropa[a]naphthalene-1-carboxylate

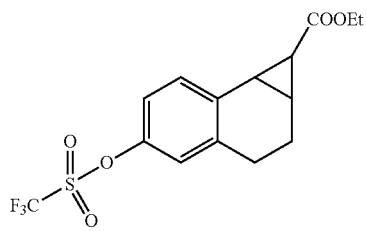

Ethyl 5-{[(trifluoromethyl)sulfonyl]oxy}-1a,2,3,7b-tetrahydro-1H-cyclopropa[a]naphthalene-1-carboxylate was synthesized analogously to example 40 from 7,8-dihydro-2-naphthalenyl trifluoromethanesulfonate (9 g, 32 mmol) at addition rate 1 ml/h to give 13 g of crude product as orange-brown oil. Purified by column chromatography on silica (200 g, ethylacetate/hexane 1:15). Fraction enriched with cis isomer (80% by GC)—0.64 g was collected and used for further transformations.

d) Ethyl 5-cyano-1a,2,3,7b-tetrahydro-1H-cyclopropa[a]naphthalene-1-carboxylate

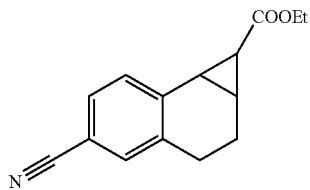

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with Zn(CN)$_2$ (0.82 mmol) and Pd(Ph$_3$P)$_4$ (56 mg, 10 mol %) in DMF (4 ml), bubbled with argon for 5 min and heated at stirring in a closed vial for 14 h at 100° C. Reaction was monitored by GC. The reaction mixture was concentrated by rotary evaporation, mixed with saturated NH$_4$Cl and extracted into ethylacetate (3×15 ml). Organic extract was washed with water and brine, dried under Na$_2$SO$_4$. Concentration gave 0.12 g of product as an oil (yield 90%).

d) 5-cyano-1a,2,3,7b-tetrahydro-1H-cyclopropa[a]naphthalene-1-carboxylic acid

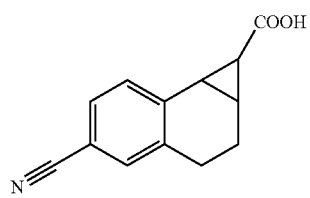

5-Cyano-1a,2,3,7b-tetrahydro-1H-cyclopropa[a]naphthalene-1-carboxylic acid was synthesized analogously to Example 69d from ethyl 5-cyano-1a,2,3,7b-tetrahydro-1H-cyclopropa[a]naphthalene-1-carboxylate (0.12 g, 0.5 mmol) to give 0.1 g of product as white crystals. Yield 94%.

$^1$H-NMR (DMSO-d$_6$): 9.70 (br s, 1H), 8.32 (br s, 1H), 8.03 (dd, 1H), 7.46-7.63 (m, 4H), 7.32 (br s, 1H), 3.18-3.10 (m, 2H), 2.76-2.65 (m, 1H), 2.62-2.51 (m, 1H), 2.34 (t, 1H), 2.01-1.80 (br m, 2H), 1.78-1.69 (br m, 1H).

Example 42A a) Ethyl 5-[(trimethylsilyl)ethynyl]-1a,2,3,7b-tetrahydro-1H-cyclopropa[a]naphthalene-1-carboxylate

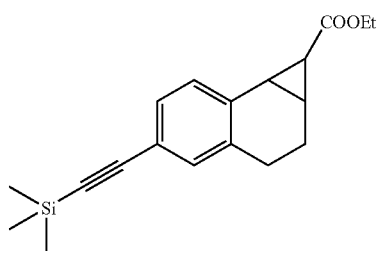

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with trimethylsylilacetylene (0.2 ml, 1.37 mmol), DPP (35 mg, 10 mol %), Pd(dba)$_2$ (30 mg, 10 mol %) and CuI (3 mg) in Et$_3$N (2.5 ml), bubbled with argon for 5 min and heated at stirring in a closed vial for 14 h at 95° C. Reaction was monitored by GC. The reaction mixture was concentrated by rotary evaporation, mixed with saturated NH$_4$Cl and extracted into ethylacetate (3×15 ml). Organic extract was washed with water and brine, dried under Na$_2$SO$_4$. Concentration gave 0.15 g of product as an oil (yield 87%).

b) 5-Ethynyl-1a,2,3,7b-tetrahydro-1H-cyclopropa[a]naphthalene-1-carboxylic acid

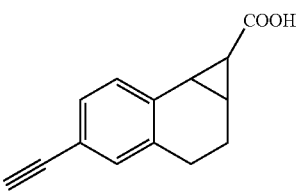

Ethyl 5-[(trimethylsilyl)ethynyl]-1a,2,3,7b-tetrahydro-1H-cyclopropa[a]naphthalene-1-carboxylate (0.2 g, 0.64 mmol) was dissolved in 4 ml of methanol and the solution of sodium hydroxide (0.05 g, 1.2 mmol) in 2 ml of water was added to the reaction mixture and stirred at heating at 65° C. for 6 h. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over Na$_2$SO$_4$ and concentrated by rotary evaporation to give 0.12 g of mixture of cis/trans:acids (85:15) as white solid. Yield 88%.

Example 43 a) 5,8-difluoro-4-methyl-3,4-dihydro-1(2H)-naphthalenone

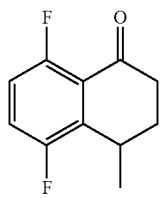

1,4-Difluorobenzene (22 ml, 210 mmol) was mixed with γ-valerolactone (4 ml, 42 mmol) and AlCl₃ (28 g, 210 mmol) was added by portions to the stirred reaction mixture. The reaction mixture was then refluxed at stirring for 16 h (oil bath 110° C.). The reaction mixture was cooled down (ice/brine bath) and ice/conc. HCl was added and stirred until homogeneous mixture was obtained. The reaction mixture was then extracted into methylene chloride, washed with water (4×10 ml) and sodium bicarbonate solution (3×100 ml). The organic extract was dried over Na₂SO₄. Concentration by rotary evaporation gave 6.7 g of product as yellow powder. Yield 81%.

b) 5,8-difluoro-4-methyl-1,2,3,4-tetrahydro-1-naphthalenol

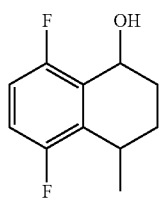

5,8-Difluoro-4-methyl-1,2,3,4-tetrahydro-1-naphthalenol was synthesized analogously to Example 69a from 5,8-difluoro-4-methyl-3,4-dihydro-1(2H)-naphthalenone to give 1.8 g of crude product, which was used in the next step without additional purification.

c) 5,8-difluoro-1-methyl-1,2-dihydronaphthalene

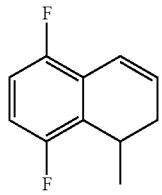

5,8-Difluoro-1-methyl-1,2-dihydronaphthalene was synthesized analogously to Example 40b from 5,8-difluoro-4-methyl-1,2,3,4-tetrahydro-1-naphthalenol (1.8 g, 9.1 mmol) to give 1.5 g of product as brown yellow oil (90% yield from 5,8-difluoro-4-methyl-1,2,3,4-tetrahydro-1-naphthalenone).

d) Ethyl 4,7-difluoro-3-methyl-1a,2,3,7b-tetrahydro-1H-cyclopropa[a]naphthalene-1-carboxylate

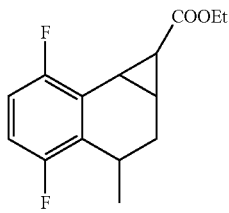

Ethyl 4,7-difluoro-3-methyl-1a,2,3,7b-tetrahydro-1H-cyclopropa[a]naphthalene-1-carboxylate was synthesized analogously to Example 40c from 5,8-difluoro-1-methyl-1,2-dihydronaphthalene (3.5 g, 19 mmol) at addition rate 0.5 ml/h to give crude product as yellow-brown oil. Purified by column chromatography on silica (200 g, ethylacetate/hexane 1:15) to give 5.2 g of the mixture of diastereomeric esters together with dimers of EDA as colourless oil (GC ratio: anti-45%; 40%/trans:cis/, syn-11%; 2.3%/trans:cis).

e) +/−anti-cis-4,7-difluoro-3-methyl-1a,2,3,7b-tetrahydro-1H-cyclopropa[a]naphthalene-1-carboxylic acid

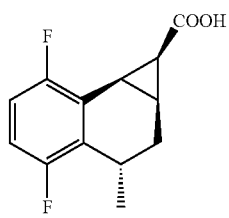

Ethyl 4,7-difluoro-1a,2,3,7b-tetrahydro-1H-cyclopropa[a]naphthalene-1-carboxylate (5.25 g, 20 mmol, ~50:50 mixture of cis and trans isomers) was dissolved in 2.5 ml of methanol and the solution of sodium hydroxide (0.4 g, 10 mmol) in 2.5 ml of water was added to the reaction mixture and stirred at ambient temperature overnight. The reaction mixture was extracted into hexane (3×30 ml). The combined extracts were washed with water and brine, dried over Na₂SO₄ and concentrated by rotary evaporation to give 1.12 g of cis esters as colourless oil (mixture of ethyl and methyl esters—94% according to GC). The mixture obtained was dissolved in 1.5 ml of methanol and the solution of sodium hydroxide (0.2 g, 5 mmol) in 1.5 ml of water was added to the reaction mixture and stirred at 95° C. for 40 min. The reaction mixture was acidified with excess of 3M HCl solution (pH=1), and extracted into ethylacetate (3×15 ml). The combined extracts were washed with water and brine, dried over Na₂SO₄ and concentrated by rotary evaporation to give 0.93 g anti-+/−cis acid as slightly orange crystals. Yield 20% (appr. quantitative if calculated for starting cis isomer).

Example 44 a) 4,7-difluoro-3-methyl-1-indanone

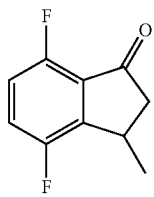

4,7-Difluoro-3-methyl-1-indanone was synthesized analogously to Example 43a from butyrolactone (4 ml, 52 mmol) to give 7.19 g of yellow powder (85:15 mixture of corresponding indanone and tertralone according to GC). The product was purified by column chromatography on silica (200 g, ethylacetate/hexane) to give 3.7 g (40% yield) of pure product together with mixed fraction and fraction containing pure tetralone.

b) 4,7-difluoro-3-methyl-1-indanol

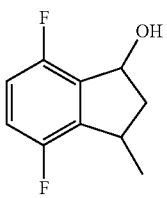

4,7-Difluoro-3-methyl-1-indanol was synthesized analogously to Example 40 from 4,7-difluoro-3-methyl-1-indanone (3.7 g, 20 mmol), to give about 3.75 g of crude product (quantitative yield), which was used in the next step without additional purification.

c) 4,7-Difluoro-1-methyl-1H-indene

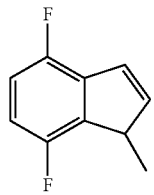

4,7-Difluoro-1-methyl-1H-indene was synthesized analogously to Example 37 from 4,7-difluoro-3-methyl-1-indanol (3.75 g, 9.1 mmol) to give 2.36 g of product as beige liquid (70% yield).

d) Ethyl 2,5-difluoro-6-methyl-1,1a,6,6a-tetrahydrocyclopropa[a]indene-1-carboxylate

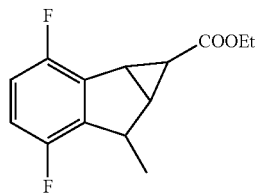

Ethyl 2,5-difluoro-6-methyl-1,1a,6,6a-tetrahydrocyclopropa[a]indene-1-carboxylate was synthesized analogously to Example 40c from 4,7-difluoro-1-methyl-1H-indene (1.32 g, 7.9 mmol) at addition rate 0.4 ml/h to give crude product as yellow-brown oil. Purified by column chromatography on silica (100 g, ethylacetate/hexane 1:15) to give 0.61 g of the mixture of diastereomeric esters cis- and trans-esters as colourless oil (cis/trans ratio: 84:16 according to NMR). Yield 30%.

e) anti-+/−cis-2,5-difluoro-6-methyl-1,1a,6,6a-tetrahydrocyclopropa[a]indene-1-carboxylic acid

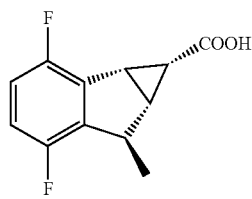

anti-+/−cis-2,5-Difluoro-6-methyl-1,1a,6,6a-tetrahydrocyclopropa[a]indene-1-carboxylic acid was synthesized analogously to the above from ethyl 2,5-difluoro-6-methyl-1,1a,6,6a-tetrahydrocyclopropa[a]indene-1-carboxylate (0.61 g, 2.4 mmol) by stepwise hydrolysis first with 20 mol. % of NaOH and then with the excess of NaOH at heating to give 380 mg of product as white crystals. Yield 70% (appr. quantitative if calculated for starting cis isomer).

Example 45 a) 5,8-difluoro-3,4-dihydro-1(2H)-naphthalenone

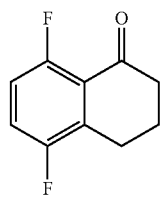

5,8-Difluoro-3,4-dihydro-1 (2H-naphthalenone was synthesized together with 4,7-difluoro-3-methyl-1-indanone according to procedure described in Example 44a. Separated by column chromatography on silica. 0.77 g of pure product was obtained yield 8%.

b) 5,8-difluoro-1,2,3,4-tetrahydro-1-naphthalenol

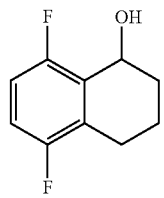

5,8-Difluoro-1,2,3,4-tetrahydro-1-naphthalenol was synthesized analogously to Example 40a from 5,8-difluoro-3,4-dihydro-1(2H)-naphthalenone (0.77 g, 4.2 mmol), to give crude product (quantitative yield), which was used in the next step without additional purification.

c) 5,8-difluoro-1,2-dihydronaphthalene

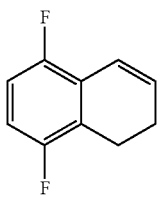

5,8-Difluoro-1,2-dihydronaphthalene was synthesized analogously to Example 40b from 5,8-difluoro-1,2,3,4-tetrahydro-1-naphthalenol to give 0.67 g of crude product as brownish liquid (90% yield from 5,8-difluoro-3,4-dihydro-1 (2H)-naphthalenone).

Additional amount of product was also obtained from the mixture of 5,8-difluoro-3,4-dihydro-1(2H)-naphthalenone and 4,7-difluoro-3-methyl-1-indanone by reduction followed by dehydration. The mixture of corresponding indene and naphthalene is easy to separate by column chromatography on silica (ethyl acetate/hexane 1:20).

d) ethyl 4,7-difluoro-1a,2,3,7b-tetrahydro-1H-cyclopropa[a]naphthalene-1-carboxylate

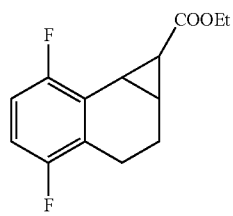

Ethyl 4,7-difluoro-1a,2,3,7b-tetrahydro-1H-cyclopropa[a]naphthalene-1-carboxylate was synthesized analogously to Example 40c from 5,8-difluoro-1,2-dihydronapthalene (0.7 g, 4.2 mmol) at addition rate 0.4 ml/h to give crude product as yellow-brown oil. Purified by column chromatography on silica (100 g, ethylacetate/hexane 1:15) to give 0.45 g of the mixture of cis- and trans-esters as colourless oil (cis/trans ratio: 33:67 according to GC).4,7-difluoro-1a,2,3,7b-tetrahydro-1H-cyclopropa[a]naphthalene-1-carboxylic acid e) 4,7-Difluoro-1a,2,3,7b-tetrahydro-1H-cyclopropa[a]naphthalene-1-carboxylic acid

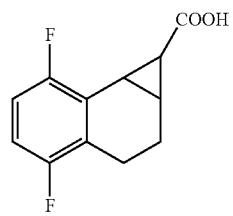

4,7-Difluoro-1a,2,3,7b-tetrahydro-1H-cyclopropa[a]naphthalene-1-carboxylic acid was synthesized analogously to Example 43e from ethyl 4,7-difluoro-1a,2,3,7b-tetrahydro-1H-cyclopropa[a]naphthalene-1-carboxylate (0.45 g, 1.8 mmol) by stepwise hydrolysis first with excess of NaOH at r.t. and then with the excess of NaOH at heating (60° C., 1.5 h) to give 80 mg of product as white crystals (cis/trans ratio 78:22 according to HPLC).

Example 46 a) 6-Bromoindene

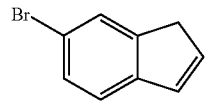

This compound was prepared analogously to Examples 40a & 40b from 5-bromo-1-indanone (4.0 g, 18.8 mmol) to give 2.4 g (65%) of 6-bromoindene.

b) (±)-cis-Ethyl 4-bromo-1,1a,6,6a-tetrahydrocyclopropa[a]indene-1-carboxylate

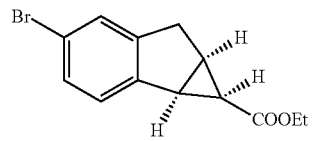

This compound was prepared analogously to Example 40c from 6-bromoindene (1.95 g, 10 mmol). Purification on silica gel starting with hexanes followed by hexanes with 2% diethyl ether and finally hexanes with 5% diethyl ether afforded 670 mg (24%) of the cis-ester.

c) (±)-cis-4-Bromo-1,1a,6,6a-tetrahydrocyclopropa[a]indene-1-carboxylic acid

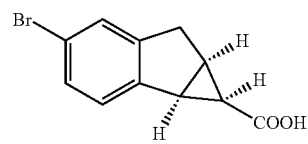

This acid was synthesized analogously to Example 40d starting with 330 mg (1.77 mmol) of the compound from Example 75b to give 232 mg (79%) of (±)-cis-4-Bromo-1,1a,6,6a-tetrahydrocyclopropa[a]indene-1-carboxylic acid.

Example 47 a) (±)-cis-Ethyl 4-cyano-1,1a,6,6a-tetrahydrocyclopropa[a]indene-1-carboxylate

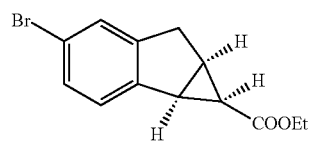

This compound was prepared analogously to Example 42d from (±)-cis-ethyl 4-bromo-1,1a,6,6a-tetrahydrocyclopropa[a]indene-1-carboxylate (200 mg, 0.7 mmol) to give, after purification on silica gel using hexanes with 10% ethyl acetate as the eluent, 73 mg (46%) of (±)-cis-ethyl 4-cyano-1,1a,6,6a-tetrahydrocyclopropa[a]indene-1-carboxylate.

b) (±)-cis-4-Cyano-1,1a,6,6a-tetrahydrocyclopropa[a]indene-1-carboxylic acid

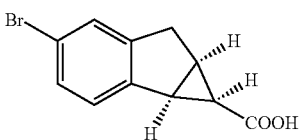

This acid was synthesized analogously to Example 40d starting with 73 mg (0.32 mmol) of the compound from Example 47a to give 59 mg (95%) of (±)-cis-4-cyano-1,1a,6,6a-tetrahydrocyclopropa[a]indene-1-carboxylic acid.

Example 48 a) 4,7-Difluoro-1-indanone

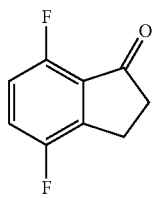

2,5-Difluorocinnamic acid (5.0 g, 27.2 mmol) was dissolved in 25 ml of ethanol and a catalytic amount of 10% Pd on carbon was added. The reaction mixture was hydrogenated at normal pressure for a period of 3 hrs. Filtration through celite and evaporation of the solvent afforded crude 3-(2,5-difluorophenyl)-propionic acid. This acid was dissolved in 75 ml of toluene and 5 ml of thionyl chloride was added. The reaction mixture was heated at +110° C. for a period of 2 hrs. Evaporation of the solvent afforded crude 3-(2,5-difluorophenyl)-propionyl chloride, which was dissolved in 25 ml of carbon disulfide and added drop wise to a suspension of 4 g of aluminium chloride in 100 ml of carbon disulfide. The reaction mixture was refluxed for 2 hrs and gave after work up and re-crystallization from ethanol 975 mg (22%) of 4,7-difluoro-1-indanone.

b) 4,7-Difluoroindene

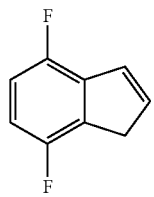

This compound was prepared analogously to Examples 40a & 40b from 4,7-difluoro-1-indanone (975 mg, 5.8 mmol) to give 475 mg (54%) of 4,7-difluoroindene.

c) (±)-cis-Ethyl 2,5-difluoro-1,1a,6,6a-tetrahydrocyclopropa[a]indene-1-carboxylate

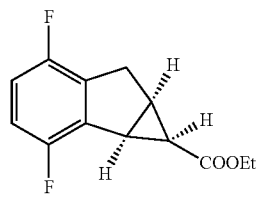

This compound was prepared analogously to Example 40c from 4,7-difluoroindene (475 mg, 3.13 mmol). Purification on silica gel starting with hexanes followed by hexanes with 2% diethyl ether and finally hexanes with 5% diethyl ether afforded 205 mg of the cis-ester contaminated with 22% of the trans-ester.

d) (±)-cis-2,5-Difluoro-1,1a,6,6a-tetrahydrocyclopropa[a]indene-1-carboxylic acid

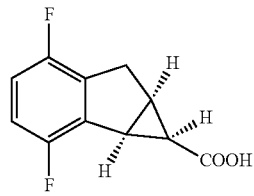

This acid was synthesized analogously to Example 40d starting with 205 mg cis-ester from Example 77c to give 120 mg of (±)-cis-2,5-difluoro-1,1a,6,6a-tetrahydrocyclopropa[a]indene-1-carboxylic acid containing a minor fraction of the corresponding trans-acid.

Example 49

4-[[6-[[[[(1S,1aS,7bS)-4,7-difluoro-1,1a,2,7b-tetrahydrocyclopropa[c][1]benzopyran-1-yl]amino]carbonyl]amino]-3-pyridinyl]oxy]-N-(4-morpholinyl)-benzamide a) N-(4-morpholinyl)-4-(phenylmethoxy)-benzamide

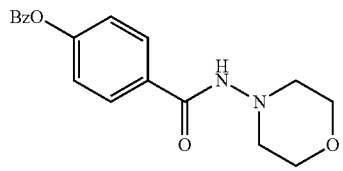

A mixture of 4-benzyloxybenzoic acid (0.5 g, 2.19 mmol), 4-aminomorpholine (0.2 mL, 2.13 mmol), Et$_3$N (0.316 mL), 1-(3-dimethylaminopropyl)-3-ethylcarbodiimide hydrochloride (0.671 g, 3.5 mmol) and 1-hydroxybenzotriazole hydrate (0.5 g, 3.7 mmol) in N,N-dimethylformamide (17 mL) was stirred at room temperature for 2 days. The reaction was concentrated and diluted in dichloromethane. The organic phase was washed twice with water, dried with MgSO$_4$ and concentrated. The residue was purified on column chromatography (silica gel, 5% MeOH in CH$_2$Cl$_2$) and N-(4-morpholinyl)-4-(phenylmethoxy)-benzamide (0.615 g, yield: 90%) was identified by NMR spectroscopy.

$^1$H-NMR (CD$_3$OD): 7.99 (s, 1H), 7.78 (d, J=8.6 Hz, 2H), 7.45 (m, 2H), 7.39 (m, 2H), 7.33 (m, 1H), 7.07 (d, J=8.6 Hz, 2H), 5.16 (s, 2H), 3.82 (m, 4H), 2.91 (m, 4H).

1b) 4-hydroxy-N-(4-morpholinyl)-benzamide

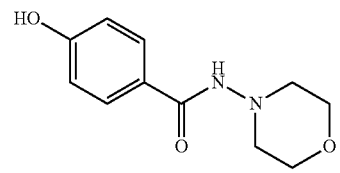

4-hydroxy-N-(4-morpholinyl)-benzamide (0.288 g, 66%) was synthesized analogously to Example 11b from N-(4-morpholinyl)-4-(phenylmethoxy)-benzamide (0.615 g).

¹H-NMR (CD₃OD): 7.67 (d, J=8.6 Hz, 2H), 6.81 (d, J=8.6 Hz, 2H), 3.80 (m, 4H), 2.8 (m, 4H).

1c) N-(4-morpholinyl)-4-[(6-nitro-3-pyridinyl)oxy]-benzamide

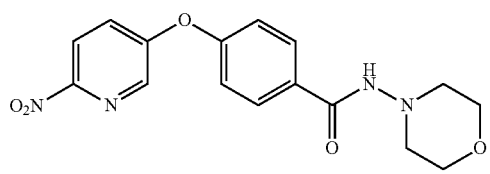

The mixture nitropyridine and bromopyridine (0.328 g) was synthesized analogously to Example 11c from 4-hydroxy-N-(4-morpholinyl)-benzamide (0.288 g).

1d) 4-[(6-amino-3-pyridinyl)oxy]-N-(4-morpholinyl)-benzamide

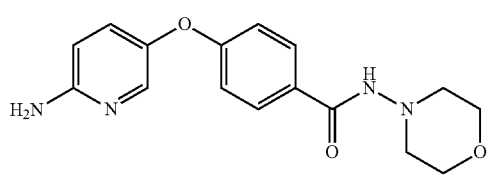

4-[(6-amino-3-pyridinyl)oxy]-N-(4-morpholinyl)-benzamide (0.234 g, 57%) was synthesized analogously to Example 11d from the mixture nitropyridine and bromopyridine (0.328 g).

¹H-NMR (CD₃OD): 7.77 (d, J=8.2, 2H), 7.73 (d, J=2.73 Hz, 1H), 7.28 (m, 1H), 6.95 (d, J=8.2 Hz, 2H), 6.65 (d, J=8.6 Hz, 1H), 3.80 (m, 4H), 2.89 (m, 4H).

1e) 4-[[6-[[[[(1S,1aS,7bS)-4,7-difluoro-1,1a,27b-tetrahydrocyclopropa[c][1]benzopyran-1-yl]amino]carbonyl]amino]-3-pyridinyl]oxy]-N-(4-morpholinyl)-benzamide

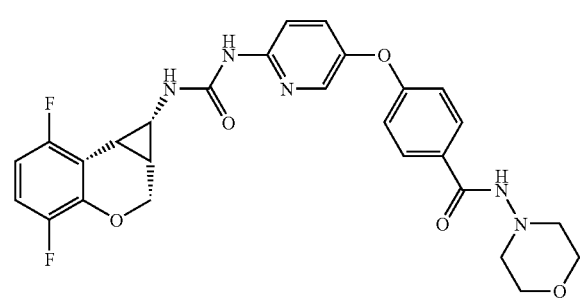

4-[[6-[[[[(1S,1aS,7bS)-4,7-difluoro-1,1a,2,7b-tetrahydrocyclopropa[c][1]benzopyran-1-yl]amino]carbonyl]amino]-3-pyridinyl]oxy]-N-(4-morpholinyl)-benzamide (0.015 g, 21%) was synthesized analogously to Example 11e from 4-[(6-amino-3-pyridinyl)oxy]-N-(4-morpholiny)-benzamide (0.041 g).

¹H-NMR (CD₃OD): 7.82 (d, J=8.6 Hz, 2H), 7.63 (d, J=2.73 Hz, 1H), 7.40 (m, 1H), 6.98 (d, J=8.6 Hz, 3H), 6.84 (m, 1H), 6.63 (m, 1H), 4.42 (d, J=11.3 Hz, 1H), 4.29 (dd, J=11.7, 2.73 Hz, 1H), 3.80 (m, 4H), 3.62 (t, J=7.2 Hz, 1H), 2.91 (m, 4H), 2.6 (t, J=8.4 Hz, 1H), 2.03 (m, 1H).

(LC-MS, API-ES⁺: 538.2; Calc. 537.5)

Example 50

1-(4,7-Difluoro-1,1a,2,7b-tetrahydro-cyclopropa[c]chromen-1-yl)-3-[5-(4-methanesulfinyl-phenoxy)-pydridin-2-yl]-urea a) 4-Methanesulfinyl-phenol

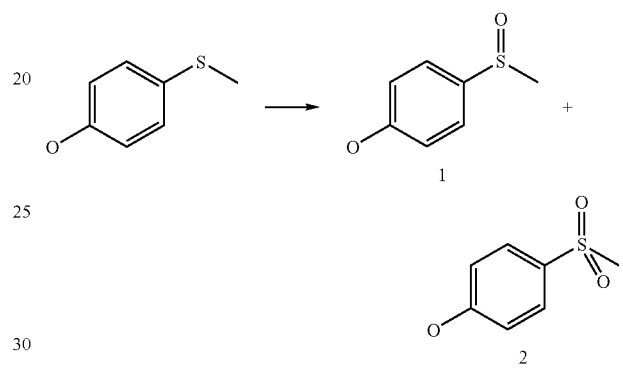

H₂WO₄ (0.029 g, 0.114 mmol) was stirred in H₂O (10 ml). 50% NaOH (0.040 ml) was first added (pH>12) and then ACOH (0.040 ml) to reach pH 5. 4-methylsulfanyl-phenol (4 g, 0.029 mol) was added and the reaction mixture was heated to 65° C. 30% H₂O₂ in H₂O (3 ml) was added in portions over 10 minutes. The reaction mixture was allowed to stir at room temperature for 1 h. 50% NaHSO₃ was added to quench the reaction. Methylene chloride was added and the compound was washed with brine and purified by chromatography (0→10% EtOH in methylene chloride) to give 1.9 g of 4-methanesulfinyl-phenol (1) (42%) and 1.5 g of 4-methanesulfonyl-phenol (2) (30%).

b) 5-(4-Methanesulfinyl-phenoxy)-2-nitro-pyridine

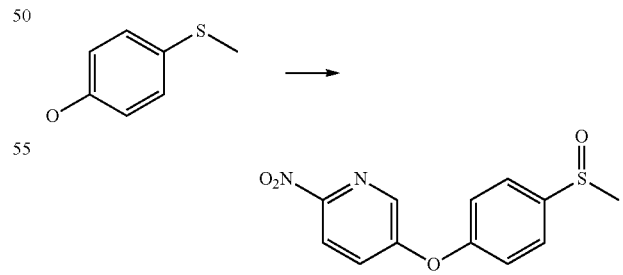

To a solution of 4-methanesulfinyl-phenol (1.52 g, 9.7 mmol) in DMF (30 ml) cesium carbonate (4.2 g, 12.9 mmol) was added, followed by addition of 5-bromo-2-nitro pyridine (1.75 g, 8.6 mmol) and the mixture was stirred at 50° C. over night. The suspension was filtered and evaporated+co-evaporated with toluene. The compound was purified by chromatography (0→10% EtOH in Methylene chloride) to give 1.5 g (56%) of 5-(4-Methanesulfinyl-phenoxy)-2-nitro-pyridine.

c) 5-(4-Methanesulfinyl-phenoxy)-pyridin-2-ylamine

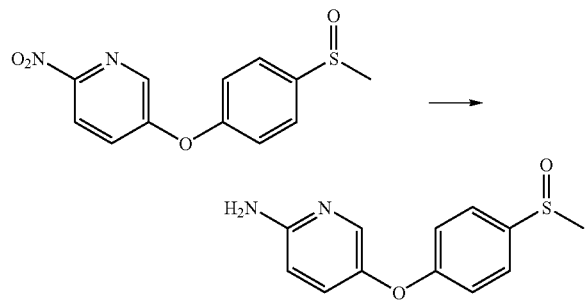

5-(4-Methanesulfinyl-phenoxy)-2-nitro-pyridine (1.27 g, 4.56 mmol) was dissolved in EtOH (30 ml) and EtOAc (8 ml). Pd/C (10%) (400 mg) was added and the nitro group was reduced to the amine by hydrogenation at atmospheric pressure for 3 h. The catalyst was filtered off and the filtrate was evaporated to give 0.6 g of 5-(4-Methanesulfinyl-phenoxy)-pyridin-2-ylamine.

d) 1-(4,7-Difluoro-1,1a,2,7b-tetrahydro-cyclopropa[c]chromen-1-yl)-3-[5-(4-methanesulfinyl-phenoxy)-pyridin-2-yl]-urea

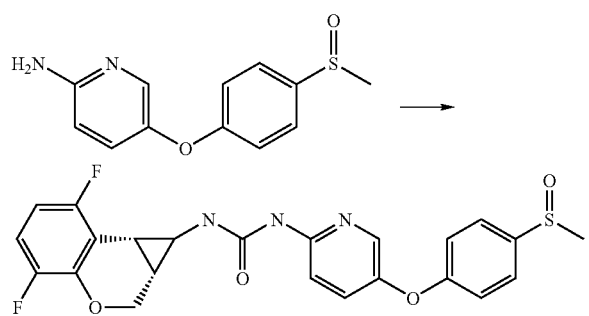

5-(4-Methanesulfinyl-phenoxy)-pyridin-2-ylamine (0.049 g, 0.197 mmol) was dissolved in toluene (2 ml). (1S,1aR,7bS)-4,7-difluoro-1,1a,2,7b-tetrahydrocyclopropa[c]chromene-1-carboxylic acid, prepared as shown in WO02/705163 (0.041 g, 0.179 mmol), DPPA (0.04 ml, 0.189 mmol) and TEA (0.025 ml, 0.180 mmol) were added. The reaction mixture was heated to 110° C. and was allowed to stir at the same temperature over night. The reaction mixture was worked up by extractions between methylene chloride and 5% citric acid followed by sat. aq. NaHCO₃. Silica gel column chromatography (5% MeOH in chloroform) gave 25 mg (30%) 1-(4,7-Difluoro-1,1a,2,7b-tetrahydro-cyclopropa[c]chromen-1-yl)-3-[5-(4-methanesulfinyl-phenoxy)-pyridin-2-yl]-urea.

$^1$H-NMR (CDCl$_3$): 9.30 (br s, 1H), 7.65 (m, 2H), 7.30 (m, 2H), 7.05 (m, 2H), 6.80-6.70 (m, 2H), 6.60 (d tr, 1H), 4.47 (dd, 1H), 4.32 (dd, 1H), 3.80 (q, 1H), 2.75 (s, 3H), 2.60 (tr, 1H), 1.99 (m, 1H).

Biological Results

Extensive guidance on the assay of test compounds at the enzyme level and in cell culture, including the isolation and/or selection of mutant HIV strains and mutant RT are found in DAIDS Virology Manual for HIV Laboratories complied by Division of AIDS, NIAID USA 1997. Resistance studies, including rational for various drug escape mutants is described in the HIV Resistance Collaborative Group Data Analysis Plan for Resistance Studies, revised 31 Aug. 1999.

Compounds of the invention are assayed for HIV activity, for example using multiple determinations with XTT in MT-4 cells (Weislow et al, J Nat Cancer Inst 1989, vol 81 no 8, 577 et seq), preferably including determinations in the presence of 40-50% human serum to indicate the contribution of protein binding. In short the XTT assay uses human T cell line MT4 cells grown in RPMI 1640 medium supplemented with 10% fetal calf serum (or 40-50% human serum as appropriate), penicillin and streptomycin seeded into 96 well microplates ($2 \cdot 10^4$ cells/well) infected with 10-20 TCID$_{50}$ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a CO$_2$ enriched atmosphere and the viability of cells is determined at day five or six with XTT vital dye. Results are typically presented as ED$_{50}$ μM.

Compounds are preferably potent against wild type virus and mutant HIV virus, especially virus comprising drug escape mutations. Drug escape mutations are those which arise in patients due to the selective pressure of a prior art antiviral and which confer enhanced resistance to that antiviral. The above cited Data Analysis Plan outlines relevant drug escape mutants for each of the antiviral classes currently on the market. Drug escape clones are readily isolated from HIV patients who are failing on a particular antiviral therapy. Alternatively the preparation of RT mutations on a known genetic background is shown in WO97/27319, WO99/61658 and WO00/73511 which also show the use of such mutants in sensitivity profiling. K103 N is a particularly relevant drug escape mutant in the context of NNRTI therapy and compounds of the invention preferably have a low ED$_{50}$ against this mutant and even more preferably the double mutant L100I, K103 especially in assays mimicking the presence of human serum.

Convenient reverse transcriptase assays use reverse transcriptase bearing key drug escape mutations prepared broadly as described in Unge et al Eur. J. Biochem. 269, 1670-1677 (2002).

For example a K103N mutant is prepared using this methodology and the primers

```
CATCCCGCAGGGTTAAAAAGAACAAATCAGTAACAGTACTGGATG
```

```
CATCCAGTACTGTTACTGATTTGTTCTTTTTTACCCTGCGGGATG
```

The L100I/K103 N mutant is prepared by mutation of L100 in the K103N enzyme:

```
CCACATCCCGCAGGGATTAAAAAGAACAAATCAGTAAC
```

```
GTTACTGATTTGTTCTTTTTAATCCCTGCGGGATGTGG
```

Mutations are done in the HIVRT DH10 clone cDNA cloned into the pET11d expression vector. The mutations are generated by amplification of the mutated DNA with the help of the enzyme Pfu. Cloning was then performed in E. coli TOP10 cells and expression of mutated enzyme was performed in E. coli BL21 (DE3) cells after induction with IPTG.

The HIV-1 reverse transcriptase assay utilized a SPA (scintillation proximity assay) system relying on fluomicrospheres coated with the receptor molecule streptavidine (Flashplates, PerkinElmer Life Science) which is capable of binding radio-labelled ligands in the reaction solution. In the assay, a biotinylated primer (5'-GTC ATA GCT GTT TCC TG-3') is pre-annealed with a DNA heterogeneous template (synthesized by GENSE) giving a sequence of 5'-CG UCU GGC AUU GCG AGC GGA UAA CM UUU CAC ACA GGA MC AGC UAU GAC-3' in an RNase free environment. HIV-1 reverse transcriptase (such as L100I+K103N) catalyzed RNA-dependent DNA activity was measured in the presence of 50 mM Tris-HCl pH=8.0, 80 mM KCl, 10 mM $MgCl_2$, 10 mM Dithiothreitol, 5 mg/ml BSA and 0.05% Nonidet P40 where the incorporation of tritium-labeled dGTP (Amersham, 35 Ci/mmol) and 11 uM of dNTP (dATP, dCTP and dTTP) was monitored at room temperature. The dGTP concentration was used at a Km value of 0.25 uM, 10 nM of RNA template was used and mutant RT (such as L100I+K103N) was used at 180 ng/ml in 100 ul reaction volume for 120 min reaction.

Compounds of the invention were assayed for HIV activity against the problematic L100I, K103N mutant in an invitro assay as outlined below. For reference, the closest prior art compound, cis-1-(4,7-difluoro-1,1a,2,7b-tetrahydro-cyclopropa[c]chromen-1-yl)-3-(5-phenoxy-pyridin-2-yl)-urea, example 20 of WO 02/070516 as depicted above, was assayed in the same system.

| Example | Substituent to phenyl (or pyridyl) | $IC_{50}$ nM |
|---|---|---|
| 1 | sulphonamido | 29 |
| 2 | N-methylcarboxamido | 26 |
| 3 | N-methylsulfonamido | 60 |
| 4 | amino | 70 |
| 5 | methylsulphonyl | 40 |
| 8 | N-methylcarboxamide (on pyridyl) | 70 |
| 9 | amide | 28 |
| 10 | carboxamide (on pyridyl) | 80 |
| 11 | hydrazinocarbonyl | 10 |
| 12 | cyclopropylamide | 27 |
| 13 | acetamide | 40 |
| 14 | triazolyl | 60 |
| Prior art | nil | 600 |

It is thus readily apparent that addition of the substituent on the right hand wing, according to the invention dramatically improves activity against the problematic double escape mutant L100I & K103N.

The invention claimed is:
1. A compound of the formula Z:

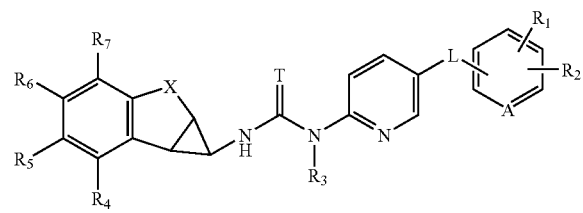

where;
A is CH or N;
$R_1$ is a substituent to a carbon atom in the ring containing A selected from —S(=O)$_p$Ra,
where Ra is —$C_1$-$C_4$ alkyl, —ORx, —NRxRx, —NHNRxRx, —NHNHC(=O)ORx, —NRxOH;
—C(=O)—Rb,
where Rb is —$C_1$-$C_4$-alkyl, ORx, —NRxRx, —NHNRxRx,
—NH$C_1$-$C_3$-alkyl-C(=O)ORx;
—NRxRc,
where Rc is H, $C_1$-$C_4$ alkyl, —NRxRx; —C(=O)Rd, —CN, S(=O)$_p$Rx
where Rd is $C_1$-$C_4$-alkyl, —ORx, —NRxRx,
—$C_1$-$C_3$-alkyl-O—$C_1$-$C_3$alkylC(=O)ORx;
—$C_1$-$C_3$-alkyl-COORx;
—$C_1$-$C_3$alkyl-ORx;
—(O—$C_1$-$C_3$alkyl)$_q$-O-Rx;
a 5 or 6 membered aromatic ring have 1-3 hetero atoms;
p and q are independently selected from 1 or 2;
Rx is independently selected from H, $C_1$-$C_4$ alkyl or acetyl; or a pair of Rx can together with the adjacent N atom form a pyrrolidine, piperidine, piperazine or morpholine ring;
$R_2$ is a substituent to a carbon atom in the ring containing A and is H, halo, cyano, $C_1$-$C_4$-alkyl, halo$C_1$-$C_4$-alkyl;
L is —O—, —S(=O)$_r$— or —$CH_2$—, where r is 0, 1 or 2;
$R_3$ is H, $C_1$-$C_3$ alkyl;
$R_4$-$R_7$ are independently selected from H, $C_1$-$C_6$ alkyl, $C_2$-$C_6$ alkenyl, $C_2$-$C_6$ alkynyl, halo$C_1$-$C_6$ alkyl, $C_1$-$C_6$ alkanoyl, halo$C_1$-$C_6$ alkanoyl, $C_1$-$C_6$ alkoxy, halo$C_1$-$C_6$ alkoxy, $C_1$-$C_6$ alkyloxy$C_1$-$C_6$ alkyl, halo$C_1$-$C_6$ alkyloxy$C_1$-$C_6$ alkyl, hydroxy$C_1$-$C_6$ alkyl, amino$C_1$-$C_6$ alkyl, carboxy$C_1$-$C_6$ alkyl, cyano$C_1$-$C_6$ alkyl, amino, carboxy, carbamoyl, cyano, halo, hydroxy, keto;
X is —($CR_8R_8'$)$_n$-D-($CR_8R_8'$)$_m$—;
T is O or S;
D is a bond, —$NR_9$—, —O—, —S—, —S(=O)— or —S(=O)$_2$—;
n and m are independently 0, 1 or 2, provided that they are not both 0 when D is a bond;
$R_8$ and $R_8'$ are independently H, $C_1$-$C_3$ alkyl, halo$C_1$-$C_3$alkyl, hydroxy, or $R_8$ and $R_8'$ together with their adjacent C atom is —C(=O)—
$R_9$ is independently H, $C_1$-$C_3$ alkyl;
and pharmaceutically acceptable salts and prodrugs thereof;
with the proviso that $R_1$ as —C(=O)Rb is not morpholinoketo-.

2. A compound according to claim 1, wherein T is O.
3. A compound according to claim 1, wherein $R_3$ is H.
4. A compound according to claim 1, wherein the cyclopropyl moiety has an enantiomeric excess of the conformation depicted in the partial formulae:

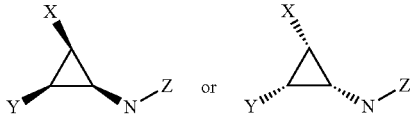

where X is as defined, Y is the bond to the (substituted) phenyl ring depicted in formula I and Z is the bond to the (thio)urea-pyridyl moiety depicted in formula Z.

5. A compound according to claim 1 wherein the compound of formula Z comprises an enantiomeric excess of the isomer showing negative optical activity.
6. A compound according to claim 1, wherein D is —O—.
7. A compound according to claim 6, wherein n is 0 and m is 1.
8. A compound according to claim 1, wherein R4 is hydrogen, fluoro or hydroxy.

9. A compound according to claim 1, wherein R5 is hydrogen, fluoro, C1-3 alkylcarbonyl or C1-3alkyloxy.

10. A compound according to claim 1, wherein R6 is hydrogen, halo, C1-C3alkyloxy, C1-3alkylcarbonyl, cyano or ethynyl.

11. A compound according to claim 10, wherein R6 is hydrogen, methoxy or fluoro.

12. A compound according to claim 1, wherein R7 is hydrogen, cyano, halo, C1-3alkyloxy, or C1-3alkylcarbonyl.

13. A compound according to claim 12, wherein R7 is cyano, fluoro or acetyl.

14. A compound according to claim 1, wherein R5 and R6 are H and R4 and R7 are fluoro.

15. A compound according to claim 1, wherein R4 is fluoro, R5 and R6 are H, and R7 is cyano or acetyl.

16. A compound according to claim 1, wherein L is —O—.

17. A compound according to claim 1, wherein R1 is —S(=O)$_2$NRxRx, S(=O)2C1-C4 alkyl, or S(=O)C1-C4 alkyl.

18. A compound according to claim 17, wherein R1 is —S(=O)2NH2, —S(=O)2NMe2 or —S(=O)2NH-cyclopropyl.

19. A compound according to claim 17, wherein R1 is —S(=O)2Me or —S(=O)Me.

20. A compound according to claim 1, wherein R1 is —C(=O)ORx, —C(=O)NRxRx, —C(=O)NHNRxRx or —C(=O)NHCH2COORx.

21. A compound according to claim 20, wherein R1 is —C(=O)OH, —C(=O)OMe, —C(=O)NH2, —C(=O)NHMe, —C(=O)NHNH2, —C(=O)NHCH2COOH.

22. A compound according to claim 20, wherein R1 is —C(=O)NRx'-N-morpholine, —C(=O)NRx'-N-piperidine, —C(=O)NRx'-N-pyrrolidine or —C(=O)NRx'-N-piperazine, where Rx is methyl, acetyl or preferably H.

23. A compound according to claim 1, wherein R1 is —NRxRx, —N(C=O)C1-C4-alkyl or —NHC(=O)CH2OC1-C3-alkyl-COORx.

24. A compound according to claim 23, wherein R1 is —NH2, —NHC(=O)Me or NHC(=O)CH2OCH2C(=O)OH.

25. A compound according to claim 1, wherein R1 is —C1-C3-alkyl-COORx; —C1-C3alkyl-ORx, —(O—C1-C3alkyl)q-O-Rx or a 5 membered ring having 1-3 hetero atoms.

26. A compound according to claim 25, wherein R1 is carboxyethyl or a methyl ester thereof, 2-methoxyethoxyethoxy or triazolyl.

27. A compound according to claim 1, wherein R1 is para to the ether linkage.

28. A compound according to claim 1, wherein the ring containing A is phenyl or pyrid-3-yl.

29. A compound according to claim 1, wherein R2 is hydrogen or fluoro.

30. A compound according to claim 1 where R2 is meta to the ether linkage.

31. A compound according to claim 1 denoted N-[(1S,1aR,7bR)-4,7-difluoro-1,1a,2,7b-tetrahydrocyclopropa[c]chromen-1-yl]-N'-[5-(4-(sulfonamido)phenoxy)-2-pyridinyl]urea

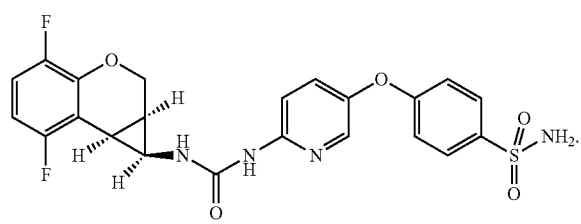

32. A pharmaceutical composition comprising a compound as defined in any preceding claim and a pharmaceutically acceptable vehicle or diluent therefor.

33. A composition according to claim 32, further comprising 1 to 3 additional HIV antivirals.

34. A composition according to claim 32, further comprising a cytochrome P450 modulator, such as ritonavir.

35. A method for the prophylaxis or treatment of HIV-1 infections comprising administering to an individual in need thereof an effective amount of the compound according to claim 1.

36. The method according to claim 35, wherein the HIV-1 infection is a drug escape mutant.

37. The method according to claim 36, wherein the drug escape mutant comprises the L100I and K103N mutations.

38. The method according to claim 35, wherein said compound is N-[(1s,1aR,7bR)-4,7-difluoro-1,1a,2,7b-tetrahydrocyclopropa[c]chromen-1-yl]-N'-[5-(4-(sulfonamido)phenoxy)-2-pyridinyl]urea

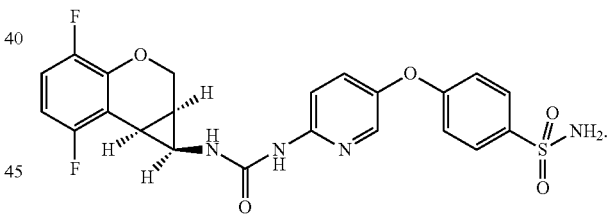

39. The method according to claim 35, wherein the administration is vaginal.

* * * * *